US007078043B2

(12) United States Patent  
Holder et al.

(10) Patent No.: US 7,078,043 B2  
(45) Date of Patent: Jul. 18, 2006

(54) MALARIA VACCINE

(75) Inventors: Anthony Holder, London (GB); Berry Birdsall, London (GB); James Feeney, London (GB); William Morgan, London (GB); Shabih Syed, London (GB); Chairat Uthaipibull, Bangkok (TH)

(73) Assignee: Medical Research Council, London (GB)

( * ) Notice: Subject to any disclaimer, the term of this patent is extended or adjusted under 35 U.S.C. 154(b) by 211 days.

(21) Appl. No.: 09/978,756

(22) Filed: Oct. 16, 2001

(65) Prior Publication Data

US 2002/0160017 A1    Oct. 31, 2002

Related U.S. Application Data

(63) Continuation of application No. PCT/GB00/01558, filed on Apr. 20, 2000, which is a continuation-in-part of application No. 09/311,817, filed on May 13, 1999, now abandoned.

(30) Foreign Application Priority Data

Apr. 20, 1999  (GB) ................................. 9909072.2  
May 25, 1999  (CA) .................................... 2271451

(51) Int. Cl.
 A61K 39/015 (2006.01)
 A61K 39/00 (2006.01)
 A61K 39/002 (2006.01)
 C12N 15/09 (2006.01)
 C12N 15/30 (2006.01)

(52) U.S. Cl. .............................. 424/268.1; 424/185.1; 424/191.1; 424/272.1; 435/69.1; 435/69.3

(58) Field of Classification Search ............. 424/130.1, 424/185.1, 190.1, 191.1, 268.1, 272.1, 93.1, 424/93.2; 435/69.1, 69.3; 514/2, 44; 530/300, 530/350, 395  
See application file for complete search history.

(56) References Cited

U.S. PATENT DOCUMENTS 5,853,724 A    12/1998  Garrity et al. ............ 424/184.1  
6,420,523 B1 *  7/2002  Chang et al. ................ 530/350

OTHER PUBLICATIONS

Rénia et al., Infection and Immunity, 65(11) :4419-4423 (1997).*  
Daly et al., Infection and Immunity, 61(6) :2462-2467 (1993).*  
Abseher, et al., "Essential Space Defined by NMR Structure Ensembles and Molecular Dynamics Simulation Show Significant Overlap", *Protein: Structure, Function and Genetics*, 31:370-382 (1998).

Barbato, et al., "Backbone Dynamics of Calmodulin Studied by $^{15}$N Relaxation Using Inverse Detected Two-Dimensional NMR Spectroscopy: The Central Helix Is Flexible", *Biochemistry*, 31:5269-5278 (1992).  
Bersch, et al., "Solution Structure of the Epidermal Growth Factor (EPG)-like Module of Human Complement Protease Clr, an Atypical Member of the EGF Family", *Biochemistry*, 37:1204-1214 (1998).  
Blackman, et al., "Secondary processing of the *Plasmodium falciparum* merozoite surface protein-1 (MSP1) by a calcium-dependent membrane-bound serine protease: shedding of MSP1$_{33}$ as a noncovalently associated complex with other fragments of the MSP1", *Mol. Biochem. Parasitol*, 50:307-316 (1992).  
Blackman, et al., "A Single Fragment of a Malaria Merozoite Surface Protein Remains on the Parasite During Red Cell Invasion and Is the Target of Invasion-inhibiting Antibodies", *J. Exp. Med*, 172:379-382 (1990).  
Blackman, et al., "A conserved parasite serine processes the *Plasmodium falciparum* merozoite surface protein-1", *Mol. Biochem. Parasitol*, 62:103-114 (1993).  
Blackman, et al., "Antibodies Inhibit the Protease-mediated Processing of a Malaria Merozoite Surface Protein", *J. Exp. Med.*, 180:389-393 (1994).  
Blackman, et al., "Proteolytic processing of the *Plasmodium falciparum* merozoite surface protein-1 produces a membrane-bound fragment containing two epidermal growth factor-like domains", *Mol. Biochem. Parasitol*, 49:29-34 (1991).  
Brandstetter, et al., "X-ray structure of clotting factor IXa: Active site and module structure related to Xase activity and hemophilia B", *Proc. Nat. Acad. Sci. USA*, 92:9796-9800 (1995).

(Continued)

*Primary Examiner*—James Housel  
*Assistant Examiner*—Zachariah Lucas  
(74) *Attorney, Agent, or Firm*—Edwards Angell Palmer & Dodge, LLP; Kathleen M. Williams

(57) ABSTRACT

A non-naturally occurring variant of a C-terminal fragment of a *Plasmodium* merozoite surface protein-1 (MSP-1) wherein said variant has (i) a reduced affinity, compared with a naturally occurring *Plasmodium* MSP-1$_{19}$, for at least one first antibody capable of blocking the binding of a second antibody, which second antibody inhibits the proteolytic cleavage of *Plasmodium* MSP-1$_{42}$ and (ii) substantially the same affinity for at least one third antibody compared with said naturally occurring *Plasmodium* MSP-1$_{19}$, which third antibody inhibits the proteolytic cleavage of *Plasmodium* MSP-1$_{42}$ is provided for use in an anti-malarial vaccine.

15 Claims, 17 Drawing Sheets

OTHER PUBLICATIONS

Figure 2:
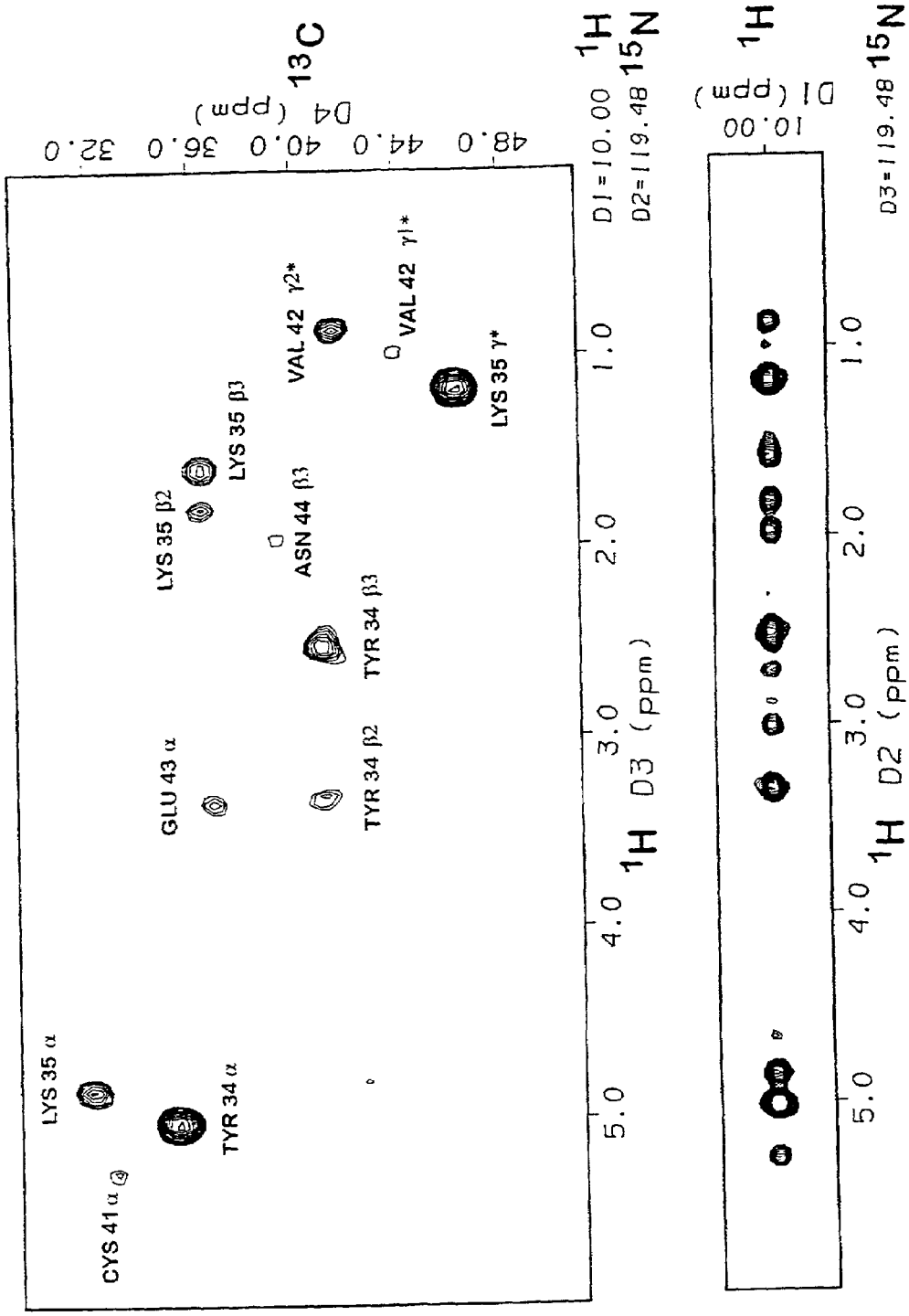

Burghaus, P.A. and Holder A.A., "Expression of the 19-kilodalton carboxy-terminal fragment of the *Plasmodium falciparum* merozoite surface protein-1 in *Escherichia coli* as a correctly folded protein", *Mol. Biochem. Parasitol*, 64:165-169 (1994).

Campbell, I.D. and Downing, A.K., "NMR of modular proteins", *Nat. Struct. Biol.*, 5 Suppl: 496-499 (1998).

Clare, J.J. and Romanos, M.A., "Expression of Cloned Genes in the Yeats *Saccharomyces cerevisiae* and *Pichia pastoris*", *Methods in Molec. Cell Biol.* 5:319-329 (1995).

Clore, G.M. and Gronenborn, A.M., "Determining the structures of large proteins and protein complexes by NMR", *Trends in Biotechnology*, 16:22-34 (1998).

Daly, et al., "Comparison of the carboxyl-terminal, cysteine-rich domain of the merozoite surface protein-1 from several strains of *Plasmodium yoelii*", *Mol. Biochem. Parasitol*, 52:279-282 (1992).

Del Portillo, et al., "Primary structure of the merozoite surface antigen 1 of *Plasmodium vivax* reveals sequences conserved between different *Plasmodium* species", *Proc. Natl. Acad. Sci. USA*, 88:4030-4034 (1991).

Diggs, et al., "The Major Merozoite Surface Protein as a Malaria Vaccine Target", *Parasitol Today*, 9:300-302 (1993).

Doreleijers, et al., "Quality Assessment of NMR Structures: a Statistical Survey", *J. Mol. Biol.*, 281:149-164 (1998).

Downing, et al., "Solution Structure of a Pair of Calcium-Binding Epidermal Growth Factor-like Domains: Implications for the Marfan Syndrome and Other Genetic Disorders", *Cell*, 85(4):597-605 (1996).

Egan, et al., "Characterization of Human T- and B-Cell Epitopes in the C Terminus of *Plasmodium falciparum* Merozoite Surface Protein 1: Evidence for Poor T-cell Recognition of Polypeptides with Numerous Disulfide Bonds", *Infect. Immun.*, 65:3024-3031 (1997).

Gibson, et al., "Structure and expression of the gene from Pv200, a major blood-stage surface antigen of *Plasmodium vivax*", *Mol. Biochem. Parasitol.*, 50:325-334 (1992).

Guevara, et al., "Antibodies that Inhibit Malaria Merozoite Surface Protein-1 Processing and Erythrocyte Invasion Are Blocked by Naturally Acquired Human Antibodies", *J. Exp. Med.*, 186:1689-1699 (1997).

Holder, et al., "Primary structure of the precursor to the three major surface antigens of *Plasmodium falciparum* merozoites", *Nature*, 317:270-273 (1985).

Holder, et al., "A Malaria Merozoite Surface Protein (MSP-1)—Structure, Processing and Function", *Mem. Inst. Oswaldo Cruz*, 87 Suppl. III:37-42 (1992).

Kay, et al., "Backbone Dynamics of Protein As Studied by $^{15}N$ Inverse Detected Heteronuclear NMR Spectroscopy: Application to Staphylococcal Nuclease", *Biochemistry*, 28:8972-8979 (1989).

Kraulis, P.J., "Molscripts—a program to produce both detailed and schematic plots of protein structures", *J. Appl. Cryst.*, 24:946-950 (1991).

Laroche, et al., "High-Level Secretion and Very Efficient Isotopic Labeling of Tick Anticoagulant Peptide (TAP) Expressed in the Methylotrophic Yeast *Pichia pastoris.*" *Bio/Technology*, 12:1119-1124 (1994).

Laskowski, et al., "AQUA and PROCHECK-NMR: Programs for checking the quality of protein structures solved by NMR", *J. Biomol. NMR*, 8:477-486 (1996).

McBride, et al., "Fragments of the polymorphic $M_r$ 185,000 glycoprotein from the surface of isolated *Plasmodium falciparum* form and antigenic complex", *Mol. Biochem. Parasitol.*, 23:71-84 (1987).

McDonald, I.K. and Thornton, J.M., "Satisfying Hydrogen Bonding Potential in Proteins", *J. Mol. Biol.*, 238:777-793 (1994).

Mrema, et al., "*Plasmodium falcipatrum*: Isolation and Purification of Spontaneously Released Merozoites by Nylon Membrane Sieves", *Exp. Parasitol.*, 54:285-295 (1982).

Nicholls, et al., "Protein Folding and Association: Insights From the Interfacial and Thermodynamic Properties of Hydrocarbons", *Proteins*, 11:281-296 (1991).

Nilges, et al., "Sampling Properties of Simulated Annealing and Distance Geometry", *J.C. Hoch, ed., NY, Plenum Press*, 451-455 (1991).

Pirson, P.J. and Perkins, M.E., "Characterization with Monoclonal Antibodies of a Surface Antigen of *Plasmodium falciparum* Merozoites", *J. Immunol.*, 134:1946-1951 (1985).

Polshakov, et al., "Determination of Stereospecific Assignments, Torsion-Angle Constraints, and Rotamer Populations in Proteins Using the Program AngleSearch", *J. Magn. Reson. Series B*, 108:31-43 (1995).

Polshakov, et al., "High-resolution Solution Structure of Human pNR-2/pS2: A Single Trefoil Motif Protein", *J. Mol. Biol.*, 267:418-432 (1997).

Perrin, S. and Gilliland, G., "Site-specific mutagenesis using asymmetric polymerase chain reaction and a single mutant primer", *Nucl. Acids Res.*, 18:7433-7438 (1990).

Qari, et al., "Predicted and observed alleles of *Plasmodium falciparum* merozoite surface protein-1 (MSP-1), a potential malaria vaccine antigen", *Mol. Biochem. Parasitol.*, 92:241-252 (1998).

Richardson, J.S., "The Anatomy and Taxonomy of Protein Structure", *Adv. Prot. Chem.*, 34:167-339 (1981).

Rychaert, et al., "Numerical Integration of the Cartesian Equations of Motion of a System with Constraints: Molecular Dynamics of n-Alkanes", *J. Comput. Phys.*, 23:327-341 (1977).

Stouote, et al., "The Current Status of Malaria Vaccines", *BIODRUGS*, 10:123-136 (1998).

\* cited by examiner

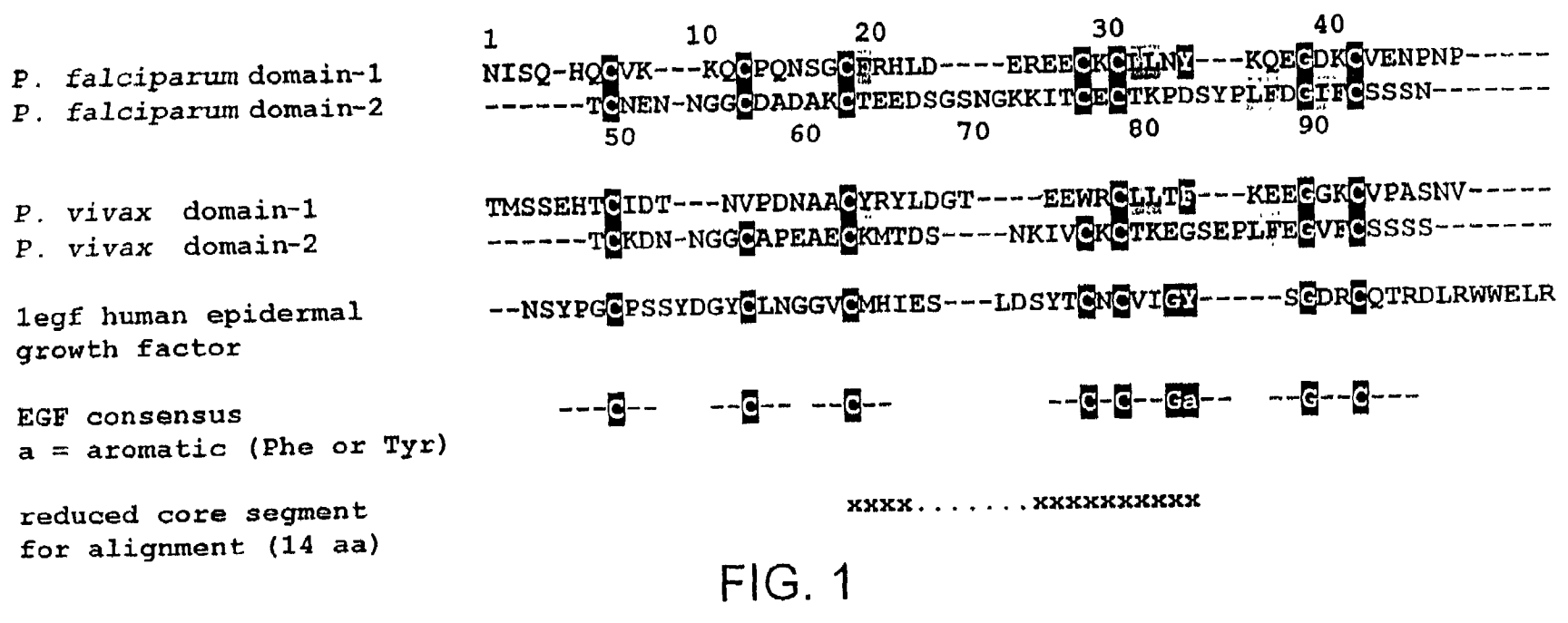

```
                                1         10             20              30            40
                                NISQ-HQCVK----KQCPQNSGCTRHLD----EREECKCLLNY----KQECDKCVENPNP----
P. falciparum domain-1          ----TCNEN-NGGCDADAKCTEEDSGSNGKKIT

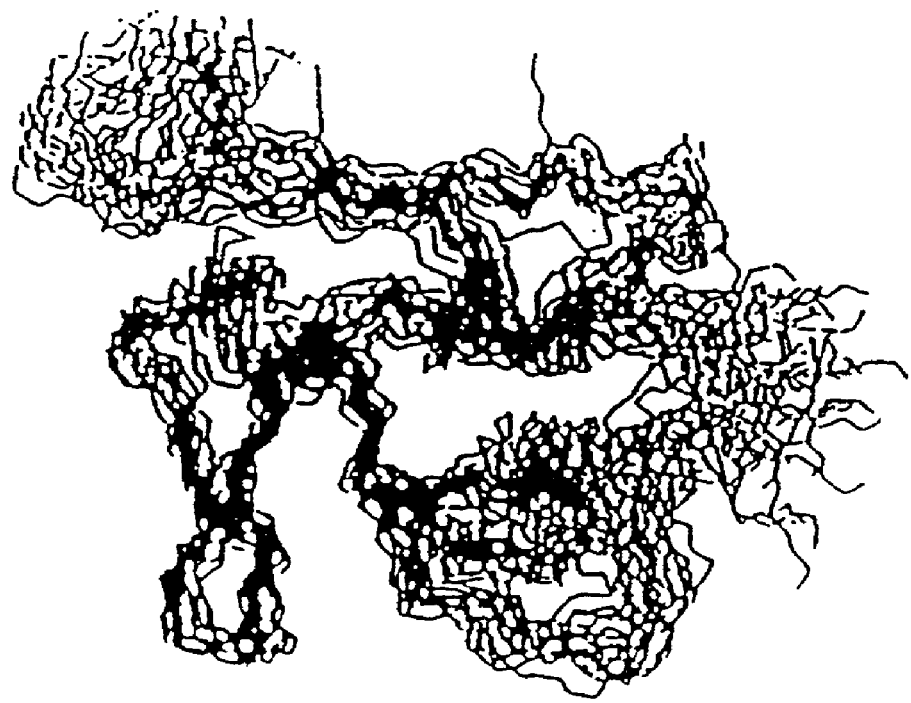
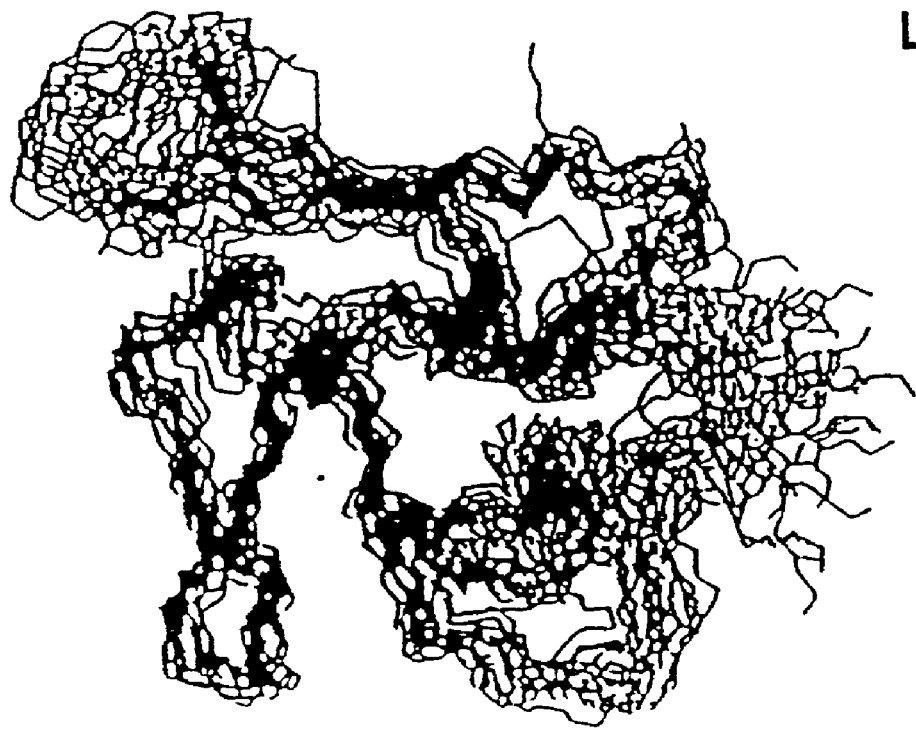
FIG. 3

FIG. 8

BIAcore analysis of mAb binding to MSP-1$_{19}$ mutant proteins

FIG. 10

BIAcore analysis of mAb binding to MSP-1₁₉ containing multiple modifications

- ☐ GST
- ▨ 12.8
- ☐ 12.10
- ▨ 5B1
- ■ 1E1
- ▨ 2.2
- ■ 7.5
- ☐ 111.4
- ■ 2F10

% Resonance Units

Protein

WT    27+31+43    27+31+34+43    15+27+31+43

FIG. 11

= Codon Usage Table for Komagataella (Pichia) pastoris
= for use with CODOP program
= Fields: [amino acid] [triplet] [frequency per thousand] [number]
= codon preferences weights:
=
=    30    preferred uniquely
=    20    preferred alternative
=    10    second best alternative
=    15    two equally preferred codons
=     1    unclassified
=     0    forbidden codons
=
= codon selection list
=
Phe   TTC
Leu   TTG > CTG
= Ile   ATC = ATT    and not  ATA
Met   ATG
= Val   GTT > GTC    and not  GTA
= Ser   TCT = TCC
Pro   CCA > CCT    and not  CCG
= Thr   ACT = ACC
= Ala   GCT > GCC    and not  GCG
= Tyr   TAC          and not  TAT
= *     UAA
His   CAC > CAT
= Gln   CAA > CAG
= Asn          AAC
Lys          AAG
= Asp          GAC > GAT
Glu   GAA = GAG
= Cys   TGT > TGC
Trp   TGG
= Arg   AGA          and not  CGC, CGA, CGG
Gly   GGT > GGA    and not  GGG

| | | | | | | | |
|---|---|---|---|---|---|---|---|
| Phe UUU 1.0( | 1) | Ser UCU 15.0( | 15) | Tyr UAU 0.0( | 0) | Cys UGU 20.0( | 20) |
| Phe UUC 30.0( | 30) | Ser UCC 15.0( | 15) | Tyr UAC 30.0( | 30) | Cys UGC 10.0( | 10) |
| Leu UUA 1.0( | 1) | Ser UCA 1.0( | 1) | Ter UAA 30.0( | 30) | Ter UGA 0.0( | 0) |
| Leu UUG 20.0( | 20) | Ser UCG 1.0( | 1) | Ter UAG 0.0( | 0) | Trp UGG 30.0( | 30) |
| | | | | | | | |
| Leu CUU 1.0( | 1) | Pro CCU 10.0( | 10) | His CAU 10.0( | 10) | Arg CGU 1.0( | 1) |
| Leu CUC 1.0( | 1) | Pro CCC 1.0( | 1) | His CAC 20.0( | 20) | Arg CGC 0.0( | 0) |
| Leu CUA 1.0( | 1) | Pro CCA 20.0( | 20) | Gln CAA 20.0( | 20) | Arg CGA 0.0( | 0) |
| Leu CUG 10.0( | 10) | Pro CCG 0.0( | 0) | Gln CAG 10.0( | 10) | Arg CGG 0.0( | 0) |
| | | | | | | | |
| Ile AUU 15.0( | 15) | Thr ACU 15.0( | 15) | Asn AAU 1.0( | 1) | Ser AGU 1.0( | 1) |
| Ile AUC 15.0( | 15) | Thr ACC 15.0( | 15) | Asn AAC 30.0( | 30) | Ser AGC 1.0( | 1) |
| Ile AUA 0.0( | 0) | Thr ACA 1.0( | 1) | Lys AAA 1.0( | 1) | Arg AGA 30.0( | 30) |
| Met AUG 30.0( | 30) | Thr ACG 1.0( | 1) | Lys AAG 30.0( | 30) | Arg AGG 1.0( | 1) |
| | | | | | | | |
| Val GUU 20.0( | 20) | Ala GCU 20.0( | 20) | Asp GAU 10.0( | 10) | Gly GGU 20.0( | 20) |
| Val GUC 10.0( | 10) | Ala GCC 10.0( | 10) | Asp GAC 20.0( | 20) | Gly GGC 1.0( | 1) |
| Val GUA 0.0( | 0) | Ala GCA 1.0( | 1) | Glu GAA 15.0( | 15) | Gly GGA 10.0( | 10) |
| Val GUG 1.0( | 1) | Ala GCG 0.0( | 0) | Glu GAG 15.0( | 15) | Gly GGG 0.0( | 0) |

FIG. 14

A:
gctgttactccatctgttatcgataacattctgtctaagattgagaacgaatacgaggtcttgtacttgaagcctctggc
cggtgtctacagatccctgaagaagcaactcgaaaacaacgtcctggattccatacaagttcaactgactttcaacgttaact
ccagattcaacagagagaaaacttcaagaacgttcctggagtctgacttgacttgattccatacaaggattgacttcttctaac
tacgttgttaaggaccatatcaacttcctgaacaggagagtgagacaagttcctgtcctcttacaactacattaagga
ctccattgtatactgatatcaacttcgctaacgactgtcctggttactacaagatctgtctgagaagtacaagtctgact
tggattccatcaagaagtacatcaatgataagtacctggtcgttcattcattggaagccaaggtcttgcaataacattgaaact
ttgtacaagactgtttaacgataagatcaagaattgaactacctcaagaccattcaggataagctgctgatttcaagaagaaca
acaactcgttggtatcgctgatttgtccactgattacaacaaccacaacaatctgttgactaagttcctgtctaccggtatg
gttttcgagaacttgctaagactgtccacaaaacccggatgttccagacatctggacgagagagaaccaaacgtgatgtctgt
tgaactacaagcaggaagtgataagtgttgagaacccaaacctcaagtgatcagacatctgaatctgtgaatgaagtaagtgcgacgct
gacgctaagtgcaccgaagaagactctggttctaacggaagaagattacttgcgaatgtactaagccagactcttaccc
tttgtttcgatgaatcttctgttcttcctaactaa

B:
TACCACCATCATCATCCACATTGAAGGTAGACAcaacattgcccaacaccaatgcgttaagaagcaatgtccacaaaactccgg
Atgttccgacatctggacgagagagaagaatgtaagtgtctgtgaactacaagcaggaagtgataagtgtgttgagaaccaa
Aactccatgtaacgagacaacggtgatgcgacgctgacgctaagtgcaccgaagaagactctgttcttaacggaagaagattc
acttgcgaatgtactaagccagactcttaccctttgtttcgatgaa
tcttctgttcttccte
taac...TGTTA

C:
YHHHHHHIEGRHNIAQHQCVKKQCPQNSGCFRHLDENEGCRCLLNYKQEGDKCVENFHTCNENNGGCDAD
AKCTEEDSGSNGKKITCECTKPDSYPLFDGIFCSSSN.

D:
gctgttactccatctgttatcgataacattctgtctaagattgagaacgaatacgaggtcttgtacttgaagcctctggc
cggtgtctacagatccctgaagaagcaactcgaaaacaacgtcctggattccatacaagttcaactgactttcaacgttaact
ccagattcaacagagagaaaacttcaagaacgttcctggagtctgacttgacttgattccatacaaggattgacttcttctaac
tacgttgttaaggaccatatcaacttcgctaacgactgtcctggttactacaagatctgtctgagaagtacaagtctgact
tggattccatcaagaagtacatcaatgataagtacctggtcgttcattcattggaagccaaggtcttgcaataacattgaaact
ttgtacaagactgtttaacgataagatcaagaattgaactacctcaagaccattcaggataagctgctgatttcaagaagaaca
gttaacgtcaggtgtatcgctgatttgtccactgattacaacaaccacaacaatctgttgactaagttcctgtctaccggtatg
gtcttcgagaacttgctaagactgtccacaaaacctggatgttccagacatctggacgagagagaaccaaacgtgatgt

E:
AVTPSVIDNILSKIENEYEVLYLKPLAGVYRSLKKQLENNVMTFNVNVKDILNSRFNKRENFKNVLESDLI
PYKDLTSSNYVVKDPYKFLNKEKRDKFLSSYNYIKDSIDTDINFANDVLGYYKILSEKYKSDLDSIKKYIN
DKQGENEKYLPFLNNIETLYKTVNDKIDLEVIHLEAKVLQYTYEKSNVEVKIKELNYLKTIQDKLADFKKN
NNFVGIADLSTDYNHNNLLTKFLSTGMVFFENLAKTVLSNLLDGNLQGML.

FIG. 15

EXPRESSION OF SYNTHETIC MSP1-19 GENE IN P. PASTORIS

|  z1  |  | z2.11 |  | z2.12 |  | NOVEX prestained markers | msp1-19 | NOVEX MK12 markers |
| a | b | a | b | a | b | | | |

1  2  3  4  5  6  7  8  9  10

FIG. 17

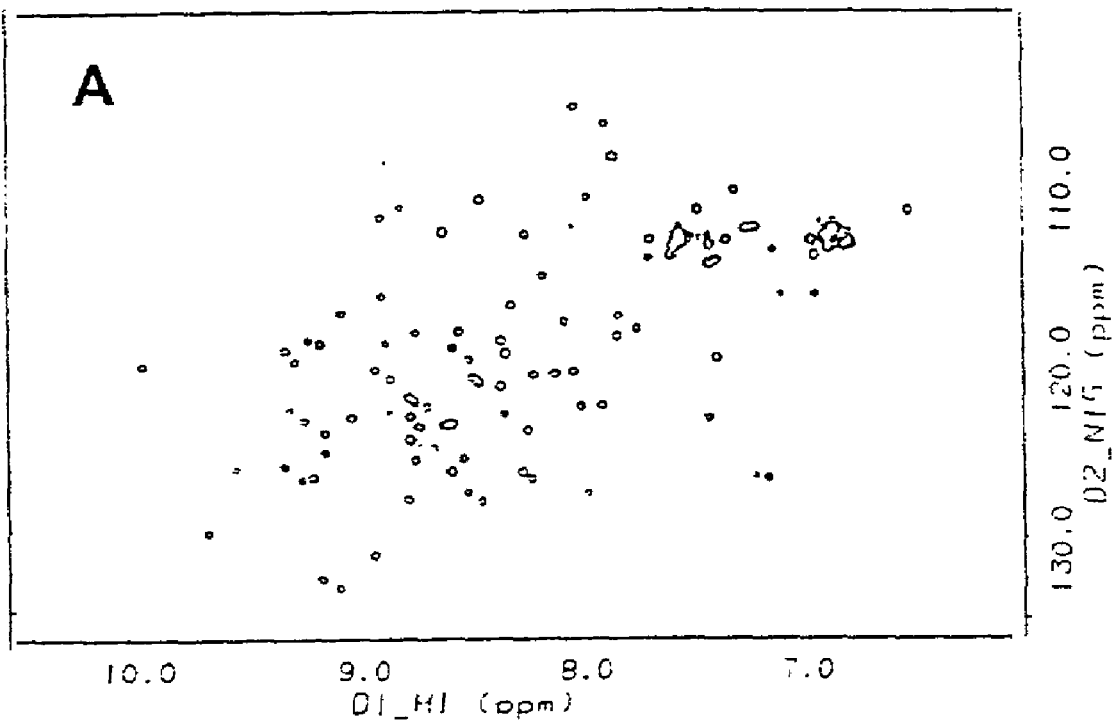
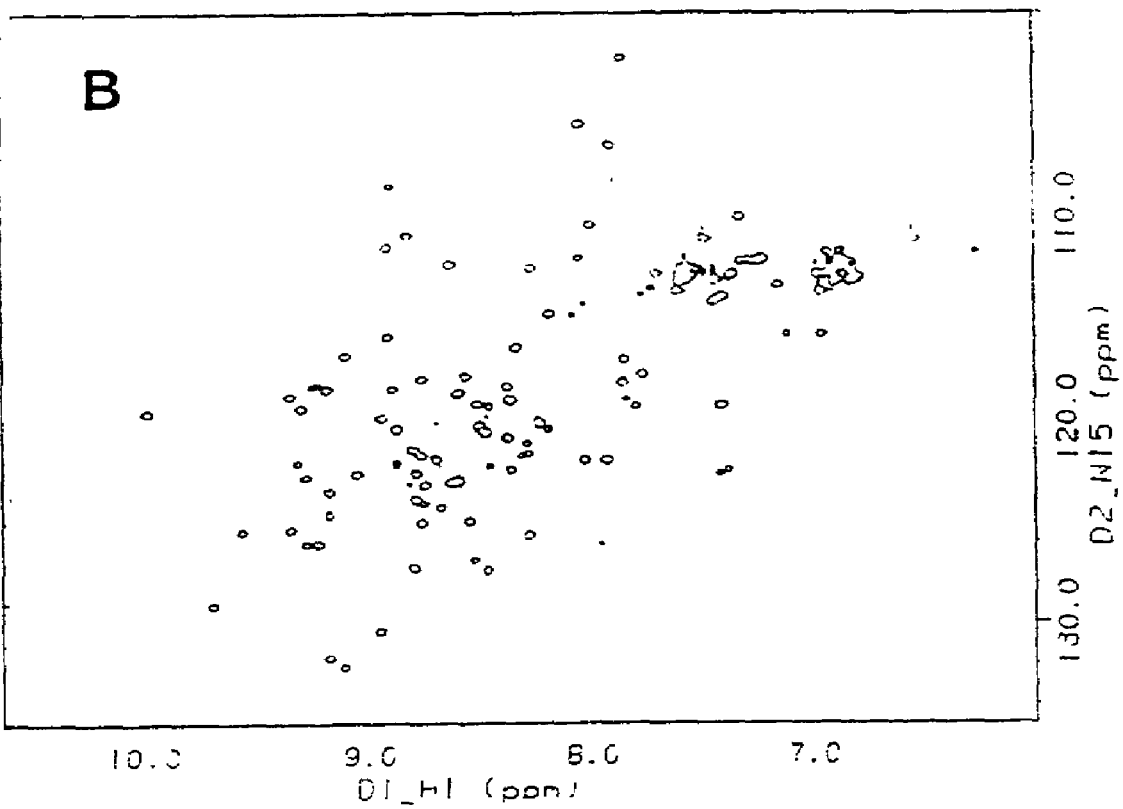
FIG. 18

MALARIA VACCINE

PRIORITY

This application is a continuation of application serial number PCT/GB00/01558, filed Apr. 20, 2000, which claims priority to application numbers GB9909072.2, filed Apr. 20, 1999, which is a continuation-in-part U.S. Ser. No. 09/311,817, filed May 13, 1999, now abandoned and CA2, 271,451, filed May 25, 1999, all of which are incorporated herein by reference in their entirety.

FIELD OF THE INVENTION

The present invention relates to modified *Plasmodium* MSP-1 protein variants and their use in producing a vaccine against malaria. It also relates to a method for the rational design of suitable variants.

BACKGROUND TO THE INVENTION

Malaria is a devastating disease that causes widespread morbidity and mortality in areas where it is transmitted by anopheline mosquitoes. In areas of high transmission young children and non-immune visitors are most at risk from this disease, which is caused by protozoa of the genus *Plasmodium*. In areas of lower or unstable transmission, epidemics of the disease can result and afflict individuals of all ages. The most dangerous form of malaria, responsible for much of the morbidity and most of the mortality, is caused by the species *Plasmodium falciparum*. It has been estimated that 2 billion people are at risk from malaria, with 200–300 million clinical cases and 1–2 million deaths each year.

The parasite has a complex life cycle in its human and mosquito hosts. In humans the stage of the life cycle which is responsible for the clinical symptoms of the disease occurs in the bloodstream. During this phase the parasite is largely hidden within host red blood cells. Here the parasite grows and multiplies. For example, within a red blood cell each *P. falciparum* parasite divides several times to produce approximately 20 new ones during a 48 hour cycle. At this point the red blood cell is burst open and the parasites (called merozoites at this stage) are released into the bloodstream. The merozoites must enter new red blood cells in order to survive and for the cycle of replication in the blood to continue. If the parasites do not manage to enter red blood cells they cannot survive for very long and are rapidly destroyed. Symptoms of malaria such as fever are associated with this cyclic merozoite release and re-invasion of red blood cells.

There is an urgent need for a vaccine against malaria. There is no effective vaccine currently available. In addition, mosquito control by the spraying of residual insecticides is either becoming ineffective or considered to be unacceptable, and there is a very worrying spread of drug resistance within parasites. The rapid spread of drug resistance is worrying because compounds such as the cheap and once-effective chloroquine are no longer useful in many parts of the world, and there are few if any new drugs available that are both cheap and effective. Vaccines against microorganisms can be very cost effective and efficient ways to protect populations against infectious diseases.

Because of the complexity of the parasite's life cycle there are a number of points in its development within humans that could be the target of a protective immune response. It is known that with increasing age and exposure individuals do become immune to malaria, suggesting that protective responses do develop with time. Broadly speaking there are three types of vaccine strategy: to target the pre-erythrocytic stages, the asexual blood stage and the sexual stage. The pre-erythrocytic stages are the sporozoites that are injected by an infected mosquito when it takes a blood meal and the initial development of the parasite in the liver. The asexual blood stage is the infection and release of merozoites from red blood cells that occurs in a cyclic manner, and the stage responsible for the manifestation of the clinical symptoms. The sexual stage takes place in the mosquito's gut after it has ingested gametocytes in a blood meal and this initiates the infection of the insect to complete the cycle; a vaccine against the sexual stages would not protect the individual but could reduce transmission and therefore the incidence of malaria in a given human population.

During the asexual cycle in the blood the parasite is directly exposed to the host's immune system, and in particular to antibodies circulating within the bloodstream, only transiently: when merozoites are released by rupture of one cell and before they penetrate another. If there are specific antibodies that can bind to the surface of the parasite then it is possible that these antibodies will interfere with the ability of the parasite to invade a new red blood cell. In fact it has been shown that several monoclonal antibodies that recognise single epitopes on parasite surface proteins, are capable of neutralising the parasite and preventing the cycle of reproduction within red blood cells.

One of the best characterised proteins on the surface of the merozoite is called merozoite surface protein 1 (MSP-1). MSP-1 is a large protein that varies in size and amino acid sequence in different parasite lines. It is synthesised as a precursor molecule of ~200 kDa by the intracellular parasite and located on the parasite's surface. During release of merozoites from red blood cells and the re-invasion of new erythrocytes the protein undergoes at least two proteolytic modifications. In the first modification as a result of a process called primary processing, the precursor is cleaved to four fragments of ~83, 30, 38 and 42 kDa that remain together as a complex on the merozoite surface. This complex also contains two other proteins of 22 kDa and 36 kDa derived from different genes. The complex is maintained by non-covalent interactions between the different subunits and is held on the merozoite surface by a glycosyl phosphatidyl inositol anchor, attached to the C-terminus of the 42 kDa fragment and inserted into the plasma membrane of the merozoite. At the time of merozoite invasion of an erythrocyte the C-terminal 42 kDa fragment is cleaved by a second proteolytic cleavage in a process called secondary processing. The result of secondary processing is that the entire complex is shed from the surface of the merozoite except for a C-terminal sub-fragment that consists of just under one hundred amino acids and which is carried into the newly invaded erythrocyte on the surface of the merozoite.

Based on sequence similarities, the structure of this small C-terminal fragment (called MSP-1$_{19}$) was suggested to consist of two epidermal growth factor (EGF)-like domains (see sequence in FIG. 1) (Blackman et al., 1991). An EGF-like motif consists of a 45-50 amino acid sequence with a characteristic disulphide bonding pattern and such domains occur frequently in extracellular modular proteins of animals. In the MSP-1 C-terminal fragment each of the motifs contains six Cys residues proposed to form three disulphide bonds and each motif has a partial match to the EGF consensus (see FIG. 1). However, because the degree of similarity is limited and since the pattern of its disulphide bonding is not known, the designation of the MSP-1 C-terminal fragment as comprised of EGF-like structures has been regarded as tentative. Other relatively divergent potential EGF-like sequences occur in *Plasmodium* proteins, but previous structure determinations have been confined to those from metazoan organisms (Campbell et al., 1998).

A number of studies have implicated MSP-1 as the target of a protective immune response. Although the goal of this work is to develop a malaria vaccine for use in humans, out of necessity most of this experimental work has been done either in model animal systems or in vitro. These include studies of the effect of specific antibodies on parasite invasion of erythrocytes in vitro, passive immunisation studies in rodent malaria models in laboratory mice and direct immunisation in both rodent and primate malaria models using either native protein (derived from the parasite) or recombinant protein expressed from parts of the MSP-1 gene in heterologous organisms. Sero-epidemiological studies have also showed a correlation between human antibody responses to parts of the MSP-1 molecule and protection against clinical disease. Much, but not all, of the work has focused on the immune response to the C-terminal MSP-$1_{19}$. For example some monoclonal antibodies that recognise MSP-$1_{19}$ prevent red blood cell invasion in in vitro cultures (Blackman et al., 1990). Interestingly, these antibodies that inhibit invasion also inhibit the secondary processing of the 42 kDa fragment, suggesting the mechanism by which they work is by steric hinderance of the protease responsible for secondary processing (Blackman et al., 1994). Since secondary processing goes to completion during successful invasion, if it cannot occur then invasion is interrupted.

All of the work described above would suggest that MSP-1 and in particular polypeptides based on the C-terminal sequence that forms the 42 kDa or the MSP-$1_{19}$ region, should be very good candidates for malaria vaccine development. However, several studies have shown that the epitopes or binding sites for antibodies on MSP-$1_{19}$ require a correct polypeptide tertiary structure, and that this is destroyed by treatments that reduce the disulphide bonds that are postulated to be present between the cysteine residues present in MSP-$1_{19}$. This limitation appears to have been overcome by the expression of recombinant protein in ways that allow antibodies that recognise the native parasite MSP-1 to bind. Other investigators have suggested that other parts of MSP-1 also have potential for inclusion in a vaccine, however the MSP-1 C-terminal fragment is currently the lead candidate for development of a vaccine against the blood stages of the malaria parasite (Diggs et al., 1993; Stoute et al., 1998).

As stated above, every ~48 hours *P. falciparum* merozoites are released from the infected erythrocyte to re-invade new red blood cells and during this time they are exposed to the host's immune system. Therefore, the question arises as to how the parasite has evolved to avoid the potentially lethal effects of, for example, neutralising antibodies. In other infectious micro-organisms it is clear that there is a constant battle between the immune system and the micro-organism, and that sophisticated mechanisms have been evolved by micro-organisms to evade the immune response. For example antigenic variation and antigenic diversity are two mechanisms that involve presenting the immune system with "a moving target" such that even though an immune response to one variant of the micro-organism may kill that variant, new variants are produced that are at least partially or fully resistant to the immune response. In the case of malaria merozoites and in particular MSP-1 an alternative mechanism has been proposed whereby the binding of some antibodies ("blocking antibodies") can prevent the binding of neutralising antibodies and thereby allow the parasite to successfully invade a red blood cell even in the presence of neutralising antibodies (Guevara Patiño et al., 1997). These blocking antibodies may be of two types, those against epitopes that are formed from amino acids that are distant in the linear primary sequence from the epitopes that are the target of neutralising antibodies, and those that are against epitopes that overlap with the epitopes of the neutralising antibodies. This represents a novel mechanism by which a parasite can evade an effective immune response, and unlike mechanisms based on antigenic polymorphism or diversity, it is not dependent upon amino acid sequence diversity.

Some monoclonal antibodies (mAbs) that bind to MSP-$1_{19}$ inhibit the proteolytic cleavage and erythrocyte invasion, suggesting that cleavage is a prerequisite for invasion (Blackman et al., 1994). Other mAbs that bind to the MSP-1 C-terminal fragment do not inhibit processing or invasion but block the binding of the inhibitory neutralizing antibodies. Other antibodies that bind to MSP-$1_{19}$ neither inhibit nor block the binding of inhibitory antibodies. In the presence of blocking antibodies, inhibitory antibodies are ineffective and invasion proceeds. The balance between inhibitory and blocking antibodies induced by immunisation may be a critical factor in determining whether or not the immune response is effective in preventing invasion (Guevara Patiño et al., 1997).

SUMMARY OF THE INVENTION

An object of the present invention is therefore to provide an effective vaccine against the malaria parasite based on variants of the *Plasmodium* MSP-1 protein. In designing such a vaccine, the following criteria should be met:
1. The amino acid sequence of the polypeptide to be used in the vaccine should contain epitopes that are the targets of, and can induce, neutralising antibodies.
2. The polypeptide should ideally not include amino acid sequences that only form epitopes for blocking antibodies.
3. If the polypeptide contains epitopes for both neutralising and blocking antibodies then it should be modified to remove the blocking antibody epitopes without affecting the neutralising epitopes.

To assist in the design of candidate vaccine polypeptides fulfilling these three criteria, it is important to determine the three-dimensional structure of the MSP-1 C-terminal fragment since this will help in mapping sites of antibody interactions with this fragment. We have therefore determined the solution structure of the MSP-1 C-terminal, including the pattern of disulphide bonding, using NMR techniques.

We have made amino acid substitutions in the sequence of MSP-$1_{19}$ that prevent the binding of individual blocking monoclonal antibodies, without affecting the binding of neutralising antibodies. By determining the 3-dimensional structure of MSP-$1_{19}$ we have identified where these antibody binding sites are located in the tertiary structure and this has allowed other amino acid substitutions to be made that have similar properties. We have shown that several substitutions, each affecting the binding of one or more blocking antibodies can be combined into a single molecule, and that these modified molecules continue to bind the neutralising antibodies but fail to bind any of the blocking antibodies. Such modified molecules are expected to be much more effective than the natural or wild-type protein structure at inducing a protective neutralising antibody response when used to immunise individuals as a malaria vaccine. In addition we have made other modifications in the primary structure of the molecule which do not affect the binding of the neutralising antibodies but which may contribute to increased immunogenicity of the molecule. The modified MSP-1$_{19}$ structures, either alone or coupled to other carriers, which may or may not contain other parts of MSP-1 to enhance the immunogenicity (for example a combination of the remainder of the MSP-1$_{42}$, which is a 42 kD a fragment of MSP-1, with the modified MSP-1$_{19}$) and provide additional T cell epitopes, would be more effective vaccines than equivalent structures that have not been modified in this way.

Accordingly, the present invention provides a non-naturally occurring variant of a C-terminal fragment of a *Plasmodium* merozoite surface protein-1 (MSP-1) wherein said variant has (i) a reduced affinity, compared with a naturally occurring *Plasmodium* MSP-1$_{19}$, for at least one first antibody capable of blocking the binding of a second antibody, which second antibody inhibits the proteolytic cleavage of *Plasmodium* MSP-1$_{42}$ and (ii) substantially the same affinity for said second antibody compared with said naturally occurring *Plasmodium* MSP-1$_{19}$.

Preferably, the *Plasmodium* MSP-1$_{19}$ and MSP-1$_{42}$ are *Plasmodium falciparum* MSP-1$_{19}$ and MSP-1$_{42}$.

The first antibody is preferably selected from mAbs IE1, 2.2, 7.5, 9C8 and 111.4. The second antibody is preferably selected from mAbs 12.8, 12.10 and 5B1.

The present invention further provides a non-naturally occurring variant of a C-terminal fragment of a *Plasmodium* merozoite surface protein-1 (MSP-1) comprising an amino acid modification at any one of amino acid residues 14, 15, 27, 31, 34, 43 48 and 53 of the *Plasmodium falciparum* MSP-1$_{19}$ amino acid sequence shown as SEQ I.D. No. 1 or their equivalent positions in other *Plasmodium* MSP-1$_{19}$ polypeptides.

Preferably said modifications are substitutions selected from Gln14→Arg, Gln14→Gly, Asn15→Arg, Glu27→Tyr, Leu31→Arg, Tyr34→Ser, Tyr34→Ile, Glu43→Leu, Thr48→Lys and Asn53→Arg and their equivalents in other *Plasmodium* MSP-1$_{19}$ polypeptides. More preferably said substitutions are combinations of substitutions selected from [Glu27→Tyr, Leu31→Arg and Glu43→Leu], [Glu27→Tyr, Leu31→Arg, Tyr34→Ser and Glu43→Leu], [Asn15→Arg, Glu27→Tyr, Leu31→Arg and Glu43→Leu] and their equivalents in other *Plasmodium* MSP-1$_{19}$ polypeptides.

In a preferred embodiment, a variant MSP-1 polypeptide of the invention further comprises a mutation at Cys12 and/or Cys28 of the *Plasmodium falciparum* MSP-1$_{19}$ amino acid sequence shown as SEQ I.D. No. 1. Preferably such modifications are substitutions selected from Cys 12→Ile and Cys28→Trp, and Cys12→Ala and Cys28→Phe.

Most preferably the substitutions are combinations selected from [Cys12→Ile, Asn 15→Arg, Glu27→Tyr, Cys28→Trp, Leu31→Arg, Glu43→Leu], [Cys12→Ile, Asn 15→Arg, Glu27→Tyr, Cys28→Trp, Leu31→Arg, Glu43→Leu, Asn53→Arg], [Cys12→Ile, Asn 15→Arg, Glu27→Tyr, Cys28→Trp, Leu31→Arg, Tyr34→Ser, Glu43→Leu, Asn53→Arg] and their equivalents in other *Plasmodium*MSP-1$_{19}$ polypeptides.

The present invention also provides a method for producing a *Plasmodium* MSP-1 variant for use in preparing a vaccine composition which method comprises modifying one or more amino acid residues of a *Plasmodium* MSP-1 C-terminal fragment such that the resulting derivative has (i) a reduced affinity, compared with a naturally occurring *Plasmodium* MSP-1$_{19}$, for at least one first antibody capable of blocking the binding of a second antibody, which second antibody inhibits the proteolytic cleavage of *Plasmodium* MSP-1$_{42}$ and (ii) substantially the same affinity for said second antibody compared with said naturally occurring *Plasmodium* MSP-1$_{19}$. In particular the method of the invention preferably comprises as a preliminary step, selecting a candidate amino acid residue by reference to a three dimensional NMR model structure, preferably as set out in Table 2. More specifically, the 3D model structure is used to select a surface exposed amino acid residue. Advantageously, a further step is included of computer modelling the three dimensional structure of the variant to exclude polypeptides that do not fold correctly.

The present invention also provides a non-naturally occurring *Plasmodium* MSP-1 variant obtained by the method of the invention.

In a further aspect, the present invention provides a polynucleotide encoding a variant of the invention operably linked to a regulatory sequence capable of directing the expression of said nucleotide in a host cell. The polynucleotide may comprise a sequence which has been optimised for expression in the host cell. The host cell may be a *Pichia pastoris* cell. Also provided is a nucleic acid vector comprising a polynucleotide of the invention, including viral vectors, and a host cell comprising a nucleotide or vector of the invention.

In another aspect, the present invention provides a pharmaceutical composition comprising a variant of the invention, a polynucleotide of the invention or a vector of the invention together with a pharmaceutically acceptable carrier or diluent.

Preferably, the composition further comprises an immunogenic *Plasmodium* polypeptide or fragment or derivative thereof such as MSP-1$_{33}$ or a fragment or derivative thereof which may be covalently attached to the non-naturally occuring MSP-1$_{19}$. It is preferred not to use wild-type MSP-1$_{19}$ sequences. The further immunogenic peptide may itself be derivatised in an analogous manner as described above for MSP-1$_{19}$. Thus, epitopes present in the peptide may be identified and modified to prevent binding of blocking antibodies, without affecting the binding of neutralising antibodies. These epitopes may be capable of binding to antibodies which have similar properties to the first antibody described above, for example, in binding affinity. The further immunogenic peptide may comprise several such modifications in its amino acid sequence.

The present invention also provides a method for producing anti-MSP-1 antibodies which method comprises administering a polypeptide variant of the invention, or a polynucleotide of the invention or a vector of the invention to a mammal, typically a non-human mammal.

In a preferred embodiment, the present invention provides a method for producing polyclonal anti-MSP-1 antibodies which method comprises administering a polypeptide variant of the invention, or a polynucleotide of the invention or a vector of the invention to a mammal, typically a non-human mammal, and extracting the serum from said mammal. Also provided is an antibody produced by the said methods.

The polypeptides, nucleotides and vectors of the present invention may be used in methods of treating and/or preventing malaria caused by *Plasmodium* species, in particular *Plasmodium falciparum*. Accordingly, the present invention provides a method of inducing immunity against malaria induced by *Plasmodium falciparum* which comprises administering to a person in need of such immunity an effective amount of a variant, a polynucleotide or a vector of the invention.

Also provided is a method of immunizing a mammal, said method comprising administering an effective amount of a variant, a polynucleotide or a vector of the invention. In particular, said mammal is immunized against malaria. Preferably the mammal is a human.

The present invention also provides a method of treating a malaria infection in a human patient which comprises administering to the patient an effective amount of the pharmaceutical composition of the invention.

We further provide according to the present invention a nucleic acid encoding a *Plasmodium* MSP-1 polypeptide, in which the nucleic acid is optimised for expression in a heterologous host cell. Preferably, the heterologous host is a *Pischia Pastoris* cell. The MSP-1 polypeptide may be selected from the group comprising an MSP-142 polypeptide comprising a sequence shown in FIGS. 15C (SEQ ID NO. 6) and 15 E (SEQ ID NO. 8), an MSP-1$_{19}$ polypeptide comprising a sequence shown in FIG. 15C (SEQ ID NO. 6), and an MSP-1$_{33}$ polypeptide comprising a sequence shown in FIG. 15E (SEQ ID NO. 8). The optimised nucleic acid may comprise a sequence selected from the sequences of FIG. 15A (SEQ ID NO. 4), FIG. 15B (SEQ ID NO. 5), and FIG. 15D (SEQ ID NO. 7). We further provide a vector comprising such a nucleic acid, a host cell comprising such a vector, and a pharmaceutical composition comprising such a nucleic acid or a vector, together with a pharmaceutically acceptable carrier or diluent. The pharmaceutical composition may further comprise an immunogenic *Plasmodium* polypeptide or fragment or derivative thereof.

DETAILED DESCRIPTION OF THE INVENTION

Although in general the techniques mentioned herein are well known in the art, reference may be made in particular to Sambrook et al., Molecular Cloning, A Laboratory Manual (1989) and Ausubel et al., Current Protocols in Molecular Biology (1995), John Wiley & Sons, Inc.

A. MSP-1 Variant Polypeptides

The variant MSP-1 polypeptides of the present invention will be described with reference to *Plasmodium falciparum* MSP-1 amino acid sequences. However, it should be appreciated that except where otherwise stated, all references to MSP-1 polypeptides include homologues of MSP-1 found in other *Plasmodium* species, such as *P. vivax*, *P. malariae* and *P. ovale* which all infect humans and *P. yoelii* which infects mice.

The variant MSP-1 polypeptides of the present invention are based on C-terminal fragments of the *Plasmodium falciparum* MSP-1$_{42}$ polypeptide shown as SEQ I.D. Nos. 2 or 3. Such polypeptides will comprise some or all of the MSP-1$_{19}$ region (SEQ I.D. No. 1), preferably at least substantially all of the domain 1 and/or domain 2 EGF-like sequences found in MSP-1$_{19}$ (approximately amino acids 1–47 and amino acids 48–96, respectively, of SEQ I.D. No. 1). It is particularly preferred to use regions that are conserved in most, more preferably all parasites of a single species to increase the effectiveness of the variant as a vaccine against a wide range of strains.

Variant MSP-1 polypeptides of the present invention comprise modifications to their primary amino acid sequence that reduce the ability of blocking antibodies to bind to the MSP-1 polypeptides. In addition, any modifications made should maintain epitopes recognised by neutralising antibodies such that the affinity of the neutralising antibodies for the MSP-1 variant is substantially the same as for naturally-occurring MSP-1 polypeptides (such as an MSP-1$_{42}$ polypeptide having the sequence shown in SEQ I.D. Nos. 2 or 3). Some reduction in the binding of some neutralising antibodies may be tolerated since the primary objective is to inhibit the binding of blocking antibodies and it is likely that an effective reduction in the binding of blocking antibodies will compensate in terms of overall vaccine efficacy for a small reduction in neutralising antibody binding.

Neutralising antibodies in the context of the present invention are antibodies that inhibit malaria parasite replication. A variety of neutralising antibodies, polyclonal and monoclonal, are known in the art, including mAbs 12.8, 12.10 and 5B1 referred to in the Examples. The activity of neutralising antibodies can be determined in a variety of ways that have been described in the art. For example, a convenient assay method described in Blackman et al., 1994 involves using preparations of merozoites (Blackman et al., 1993; Mrema et al., 1982) to measure cleavage of MSP-1$_{42}$ into MSP-1$_{33}$ and MSP-1$_{19}$. Briefly, freshly isolated merozoites are washed in ice-cold buffer and divided up into aliquots of about $2\times10^9$ merozoites. A test antibody is added to each aliquot and the sample incubated at 37° C. for 1 hour. The samples are then subjected to SDS-PAGE under non-reducing conditions on a 12.5% polyacrylamide gel, Western blotted and the blot probed with antiserum to MSP-1$_{33}$. In the control sample, two main bands are seen—one corresponding to MSP-1$_{42}$ and one lower molecular weight band corresponding to MSP-1$_{33}$. Neutralising antibodies will reduce the amount of the lower molecular weight band as a result of inhibiting secondary proteolytic processing of MSP-1$_{42}$.

This method is a particularly preferred method for assessing the efficacy of neutralising antibodies in the presence of antibodies believed to act as blocking antibodies. Where candidate competing blocking antibodies are to be tested, the merozoite sample is preincubated with a blocking antibody for 15 mins on ice prior to incubation with a neutralising antibody at 37° C. for 1 hour as described above. Thus blocking antibodies can readily be identified and/or characterised using such an assay method.

Other assay methods include merozoite invasion inhibition tests as described in Blackman et al., 1990.

As discussed above, blocking antibodies are defined in the context of the present invention as antibodies that inhibit the binding of neutralising antibodies to MSP-1 but which do not themselves inhibit invasion of red blood cells by malaria parasites. Thus they "block" the neutralising function of the neutralising antibodies. A variety of blocking antibodies have been characterised in the art, including mAbs IE1, 2.2, 7.5 and 111.4 referred to in the Examples. As discussed above, blocking antibodies can conveniently be identified and/or characterised using assays that test their effect on neutralising antibody function.

Modifications that may be made to produce MSP-1 variants of the invention include substitutions, deletions and insertions. It is particularly preferred to use substitutions to minimise disruption of the secondary/tertiary structure of the polypeptide. Furthermore, particularly preferred substitutions are those that replace one class of amino acid with another class, such as an aliphatic non-polar residue with a charged polar residue. For example, the twenty naturally occurring amino acids may be divided into four main groups (aliphatic non-polar [G, A, P, I, L and V], polar un-charged

[C, S, T, M, N and Q], polar charged [D, E, K and R] and aromatic [H, F, W and Y]) and it is preferred to replace an amino acid from one group with an amino acid from another group.

Other possibilities include replacing a positively charged side chain with a negatively charged side chain, replacing an amino acid with a large side chain with an amino acid with a smaller or no side chain (glycine), replacing a polar amino acid with a charged polar amino acid, replacing a large aromatic amino acid with an amino acid with a small side chain, and replacing cysteine residues that are involved in disulphide bonds.

Particularly preferred modifications are an amino acid modification at any one of amino acid residues 14, 15, 27, 31, 34, 43, 48 and 53 of the *Plasmodium falciparum* MSP-1$_{19}$ amino acid sequence shown as SEQ I.D. No. 1 or their equivalent positions in other *Plasmodium* MSP-1$_{19}$ polypeptides. These residues are all almost within the EGF-like domain 1. It is known that the epitopes of some antibodies contain amino acid sequences that are within EGF-like domain 2, therefore equivalent modifications may also be made in EGF-like domain 2. Preferred examples of modifications include the following substitutions Gln14→Arg, Gln14→Gly, Asn15→Arg, Glu27→Tyr, Leu31→Arg, Tyr34→Ser, Tyr34→Ile, Glu43→Leu, Thr48→Lys and/or Asn53→Arg and their equivalents in other *Plasmodium* MSP-1$_{19}$ polypeptides.

It is especially preferred to carry out more than one modification, i.e. to use combinations of modifications, such as two or more or three or more. In a preferred embodiment, an MSP-1 variant of the invention comprises a combination of amino acid substitutions selected from [Glu27→Tyr, Leu31→Arg and Glu43→Leu], [Glu27→Tyr, Leu31→Arg, Tyr34→Ser and Glu43→Leu], [Asn15→Arg, Glu27→Tyr, Leu31→Arg and Glu43→Leu] and their equivalents in other *Plasmodium* MSP-1$_{19}$ polypeptides.

A particularly preferred combination further comprises a modification to Cys12 and/or Cys28 (and/or their equivalent residues in EGF-like domain 2) to disrupt the disulphide bond. Preferably such modifications are substitutions selected from Cys12→Ile and Cys28→Trp, and Cys12→Ala and Cys28→Phe.

Most preferably the substitutions are combinations selected from [Cys12→Ile, Asn 15→Arg, Glu27→Tyr, Cys28→Trp, Leu31→Arg, Glu43→Leu], [Cys12→Ile, Asn15→Arg, Glu27→Tyr, Cys28→Trp, Leu31→Arg, Glu43→Leu, Asn53→Arg], [Cys12→Ile, Asn15→Arg, Glu27→Tyr, Cys28→Trp, Leu31→Arg, Tyr34→Ser, Glu43→Leu, Asn53→Arg] and their equivalents in other *Plasmodium* MSP-1$_{19}$ polypeptides.

Substitutions are not confined to using naturally occurring amino acids—non-naturally occurring amino acid analogues may also be used, in particular where solid phase synthesis is to be used to chemically synthesise the variant, as opposed to recombinant technology.

Modifications to MSP-1 amino acid sequences may be carried out using standard techniques such as site-directed mutagenesis using the polymerase chain reaction. Alternatively, variants may be obtained by solid phase synthetic techniques.

To determine whether a variant MSP-1 polypeptide produced by modification of its primary amino acid sequence complies with the criteria specified above, the affinity of at least one neutralising antibody and at least one blocking antibody for the variant polypeptide compared with the naturally occurring MSP-1 sequence may be tested. Ideally more than one of each type of antibody should be used, for example two or three.

The ability of antibodies to bind to the variant and wild-type polypeptides may be determined using any one of a variety of methods available in the art for determining antibody-epitope binding. One such method, described in the Examples, involves the use of MSP-1 sequences expressed as fusion proteins with a protein tag such as glutathione-S-transferase (GST). These GST-fusion proteins are typically immobilised to a solid phase such as glutathione sepharose beads or a BIAcore sensor chip. Binding of antibodies, such as monoclonal antibodies, to the fusion proteins may be determined using standard techniques such as Western blotting and/or by labelling the antibodies with a radioactive label such as $^{125}$I. The use of BIAcore technology allows easy quantitation of the results.

Preferably, the reduction in binding of at least one of the blocking antibodies tested is at least 50% compared to wild-type MSP-1, more preferably at least 75, 80 or 90%, typically as assessed using recombinantly expressed MSP-1 immobilised to a BIAcore sensor chip. By contrast, the binding of at least one, for example at least two or three, of the neutralising antibodies tested, more preferably at least half of the neutralising antibodies tested, more preferably substantially all of the neutralising antibodies tested is reduced by less than 50%, more preferably less than 25%. The number of neutralising antibodies that need be tested to confirm compliance with the test criteria will not typically exceed from three to five different antibodies (three antibodies are used in the Examples). In a particularly preferred embodiment the binding of at least one neutralising antibody is increased by at least 10%.

The results given in Table 2 in the Examples provide partial guidance to the skilled person as to which residues may be modified to produce a variant MSP-1 of the invention. However, the provision herein for the first time of the three dimensional solution structure of MSP-1$_{19}$ provides the skilled person with further detailed guidance as to which residues may be altered. In particular, epitopes are expected to be exposed to the aqueous environment on the exterior of the MSP-1$_{19}$ fragment. Consequently, the precise structural information provided which teaches the position of surface exposed amino acids allows the skilled person to target those residues for modification. This data is given in Tables A/B and has also been submitted to the Protein Data Bank (PDB Accession no. 1CEJ). It enables the skilled person to identify the precise location of individual amino acids in the three dimensional structure. Typically, the data is loaded into suitable software, well-known in the art such as Insight II, MOLSCRIPT GRAS P and RASMOL.

Further, knowing the location of a modification in the 3-dimensional structure which affects the binding of a blocking antibody without affecting the binding of the neutralising antibodies, it is possible to identify other residues that are on the surface and in the vicinity of the original modification and which may be easily modified to further improve the properties of a modified protein. These residues may be in either the first or the second EGF-like motifs or in the sequence between them. Since it is known that an antibody binding site can encompass a volume that corresponds approximately to the range of 5 to 8 amino acids, it is clear that modifications of these adjacent residues may also affect the affinity of the protein for the blocking antibodies. Once an adjacent amino acid has been identified it can be modified according to the principles outlined above and the contribution of the modification to the overall antigenicity and immunogenicity of the protein, either alone or in combination with other modifications, can be assessed. Those changes that contribute to a reduced affinity for the blocking antibodies, without a substantial affect on binding of the neutralising antibodies can be incorporated into the improved protein. This can be a reiterative process.

In addition, the 3D NMR structure will enable the skilled person to carry out preliminary computer modelling studies of MSP-$1_{19}$ variants with specific modifications so that, for example variants that cannot fold properly may be discarded. This will assist in minimising the number of candidate MSP-$1_{19}$ variants that need be tested.

Thus the present invention also provides a computer readable medium having stored thereon a model of the MSP-$1_{19}$ NMR structure. In a preferred embodiment, said model is built from all or some of the NMR data shown in Tables A and B.

Variants of the present invention may optionally include additional MSP-1 sequences, in particular regions of the MSP-$1_{33}$ region of MSP-$1_{42}$ to confer additional immunogenicity to the variant. Furthermore, additional sequences known to contain and promote T cell responses are advantageously included (i.e. T cell epitopes). Other modifications may also be made that increase immunogenicity such as modifications that alter the pathway of antigen processing and presentation.

Polypeptide variants of the invention are typically made by recombinant means, for example as described below. However they may also be made by synthetic means using techniques well known to skilled persons such as solid phase synthesis. Proteins of the invention may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the immunogenicity of the MSP-1 variant.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

B. Polynucleotides and Vectors

As discussed above, the variants of the present invention may be produced recombinantly using standard techniques. Thus, the present invention also provides a polynucleotide encoding a polypeptide MSP-1 variant of the invention. Polynucleotides of the invention may comprise DNA or RNA. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention. It will be understood by a skilled person that numerous different polynucleotides can encode the same polypeptide as a result of the degeneracy of the genetic code.

Polynucleotides of the invention comprise can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells. The host cell may be a methylotrophic yeast such as *Pichia pastoris*.

The coding sequence of natural or variant MSP polypeptides (including the polypeptide of the invention) may be modified for optimal expression in a host cell. For example, secondary modification such as N-glycosylation may be prevented by removal of sequences necessary for such modification. The sequence of the polypeptide may alternatively or in addition be modified with respect to codon usage for optimal expression in the host cell. Methods of mutagenising a sequence are known in the art; alternatively, the modified coding sequence may be generated by means of PCR gene assembly using overlapping synthetic oligonucleotides (Stemmer et al., 1995; Withers-Martinez et al., 1999).

Preferably, a polynucleotide of the invention in a vector is operably linked to a regulatory sequence that is capable of providing for the expression of the coding sequence by the host cell, i.e. the vector is an expression vector. The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

Such vectors may be transformed or transfected into a suitable host cell using standard techniques above to provide for expression of a polypeptide of the invention. This process may comprise culturing a host cell transformed with an expression vector as described above under conditions to provide for expression by the vector of a coding sequence encoding the polypeptides, and optionally recovering the expressed polypeptides.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in a method of gene therapy.

Promoters/enhancers and other expression regulation signals may be selected to be compatible with the host cell for which the expression vector is designed. For example, prokaryotic promoters may be used, in particular those suitable for use in *E. coli* strains (such as *E. coli* HB101 or DH5α).

When expression of the polypeptides of the invention in carried out in mammalian cells, either in vitro or in vivo, mammalian promoters may be used. Tissue-specific promoters may also be used. Viral promoters may also be used, for example the Moloney murine leukaemia virus long terminal repeat (MMLV LTR), the promoter rous sarcoma virus (RSV) LTR promoter, the SV40 promoter, the human cytomegalovirus (CMV) IE promoter, herpes simplex virus promoters or adenovirus promoters. All these promoters are readily available in the art.

C. Administration

The variant MSP-1 polypeptides of the present invention and nucleic acid molecules may be used to treat or prevent malaria in animals, specifically humans.

The polypeptides of the invention may be administered by direct injection. Preferably the polypeptides are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration. Typically, each polypeptide is administered at a dose of from 0.01 to 30 µg/kg body weight, preferably from 0.1 to 10 µg/kg, more preferably from 0.1 to 1 µg/kg body weight. It is also possible to use antibodies prepared using the polypeptides of the invention, as described below, in treating or preventing *Plasmodium* infection. Neutralising antibodies, or fragments thereof which retain specificity for *Plasmodium* antigens, can be administered in a similar manner to the polypeptides of the invention.

The polynucleotides of the invention may be administered directly as a naked nucleic acid construct. When the expression cassette is administered as a naked nucleic acid, the amount of nucleic acid administered is typically in the range of from 1 µg to 10 mg, preferably from 100 µg to 1 mg.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Alternatively, the polynucleotide may be administered as part of a nucleic acid vector, including a plasmid vector or viral vector, such as a vaccinia virus vector. When the polynucleotide of the invention is delivered to cells by a viral vector of the invention, the amount of virus administered is in the range of from $10^3$ to $10^{10}$ pfu, preferably from $10^5$ to $10^8$ pfu, more preferably from $10^6$ to $10^7$ pfu. When injected, typically 1–10 µl of virus in a pharmaceutically acceptable suitable carrier or diluent is administered.

Preferably the delivery vehicle (i.e. naked nucleic acid construct or viral vector comprising the polynucleotide for example) is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosages described are intended only as a guide since a skilled practitioner will be able to determine readily the optimum route of administration and dosage for any particular patient and condition.

D. Preparation of Vaccines

Vaccines may be prepared from one or more polypeptides of the invention. They may also include one or more immunogenic *Plasmodium* polypeptides known in the art. Thus a vaccine of the invention may comprise one or more polypeptides of the invention and optionally, one or more polypeptides selected from, for example, the asexual blood stage proteins: apical merozoite antigen-1, erythrocyte binding antigen 175, erythrocyte membrane protein-1; the hepatic stage proteins: liver stage antigens 1 and 3; the sporozoite stage proteins: circumsporozoite protein, thrombospondin related adhesive protein; and the sexual stage proteins Pfs25 and Pfs28 polypeptides and immunogenic fragments thereof. Preferably, the other immunogenic *Plasmodium* polypeptides known in the art do not contain wild type MSP-$1_{19}$ sequences.

The preparation of vaccines which contain an immunogenic polypeptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an MSP-1 antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The polypeptides of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

E. Dosage and Administration of Vaccines

The vaccines are administered in a manner compatible with the dosage formulation, and in such amount as will be prophylactically and/or therapeutically effective. The quantity to be administered, which is generally in the range of 5 μg to 250 μg of antigen per dose, depends on the subject to be treated, capacity of the subject's immune system to synthesise antibodies, and the degree of protection desired. Precise amounts of active ingredient required to be administered may depend on the judgement of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reinforce the immune response, for example, at 1 to 4 months for a second dose, and if needed, a subsequent dose(s) after several months. The dosage regimen will also, at least in part, be determined by the need of the individual and be dependent upon the judgement of the practitioner.

In addition, the vaccine containing the immunogenic MSP-1 antigen(s) may be administered in conjunction with other immunoregulatory agents, for example, immunoglobulins.

F. Preparation of Antibodies Against the Polypeptides of the Invention

The variant MSP-1 polypeptides prepared as described above can be used to produce antibodies, both polyclonal and monoclonal. If polyclonal antibodies are desired, a selected mammal (e.g., mouse, rabbit, goat, horse, etc.) is immunised with an immunogenic polypeptide bearing an MSP-1 epitope(s). Serum from the immunised animal is collected and treated according to known procedures. If serum containing polyclonal antibodies to an MSP-1 epitope contains antibodies to other antigens, the polyclonal antibodies can be purified by immunoaffinity chromatography. Techniques for producing and processing polyclonal antisera are known in the art.

Monoclonal antibodies directed against MSP-1 epitopes in the polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against MSP-1 epitopes can be screened for various properties; i.e., for isotype and epitope affinity.

The polypeptides of the invention can also be used to select for human monoclonal antibodies using the variable regions of immunoglobulin heavy and light chains cloned in the form of a phage display library, preferably from individuals who have been previously exposed to a natural malaria infection.

Antibodies, both monoclonal and polyclonal, which are directed against MSP-1 epitopes are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the infectious agent against which protection is desired.

Techniques for raising anti-idiotype antibodies are known in the art. These anti-idiotype antibodies may also be useful for treatment of *Plasmodium* infections, as well as for an elucidation of the immunogenic regions of MSP-1 antigens. It is also possible to use fragments of the antibodies described above, for example, F(ab')$_2$, Fab, Facb and scFv fragments.

It should be appeciated that features from various sections, aspects and embodiments of the invention as described above are generally equally applicable to other sections, aspects and embodiments *mutatis mutandis*.

The invention will now be further described by way of Examples, which are meant to serve to assist one of ordinary skill in the art in carrying out the invention and are not intended in any way to limit the scope of the invention. The Examples refer to the Figures. In the Figures:

DETAILED DESCRIPTION OF THE FIGURES

FIG. 1—MSP—1 sequences aligned according to the EGF—like motif consensus. Top sequence: *P. falciparum* (SWISS-PROT MSP1 PLAFW SEQ ID NO's 9 and 10). Second sequence: *P. vivax* Belem strain (PIR A45604, SEQ ID NO's 11 and 12). Third sequence: human EGF (PDB 1egf, SEQ ID NO 13). Fourth sequence: EGF-like domain consensus (Prosite EGF1). Bottom sequence: 14 residue EGF core region used for structure alignment in FIG. 6. Black highlighting indicates conserved residues of the EGF-like domain. Dark shading shows hydrophobic residues at the EGF-module pair interface in the *P. falciparum*, and corresponding conserved residues in the *P. vivax* sequence.

FIG. 2—Sample of multidimensional heteronuclear NOESY experiments showing planes containing NOE connections to the MSP-1 C-terminal fragment Lys35 NH proton. Top: $^{13}$C (D4) and $^1$H(D3) plane from the 4D-[$^{13}$C]-HMQC-NOESY-[$^{15}$N]-HSQC experiment, taken at the chemical shift values of Lys35 NH in $^{15}$N(D2) and $^1$H(D1). Bottom: strip from the 3D [$^{15}$N]-NOESY-HSQC at the $^1$H chemical shift value of Lys35 NH (vertical axis, D1) taken at the plane of its $^{15}$N (D3) value. The horizontal $^1$H axis is aligned with that of the top spectrum. The weak cross-peaks at 2.72 and 3.01 ppm in the 3D spectrum do not show corresponding cross-peaks in the 4D spectrum because of the lower signal-to-noise ratio in the latter. These peaks have been assigned as the cross-peaks between Lys35 NH and Asn44 H$_{\beta 2}$ (2.72 ppm), and Cys30 H$_{\beta 3}$ and/or Cys41 H$_{\beta 2}$ (3.01 ppm).

FIG. 3—Stereo drawing showing the backbone C, N, C$_\alpha$ atoms of the 32 refined structures in the final ensemble. The domain-1 is on the left (red), with domain-2 on the right (green), and both the N- and C-termini are near the bottom.

Figure 4:

FIG. 4—MOLSCRIPT picture of the most representative model of the ensemble, showing the backbone C$_\alpha$ trace, antiparallel β-sheet elements, and disulphide bridges (S$_\gamma$ atoms in yellow). Domain-1, red; Domain-2, green.

Figure 5:
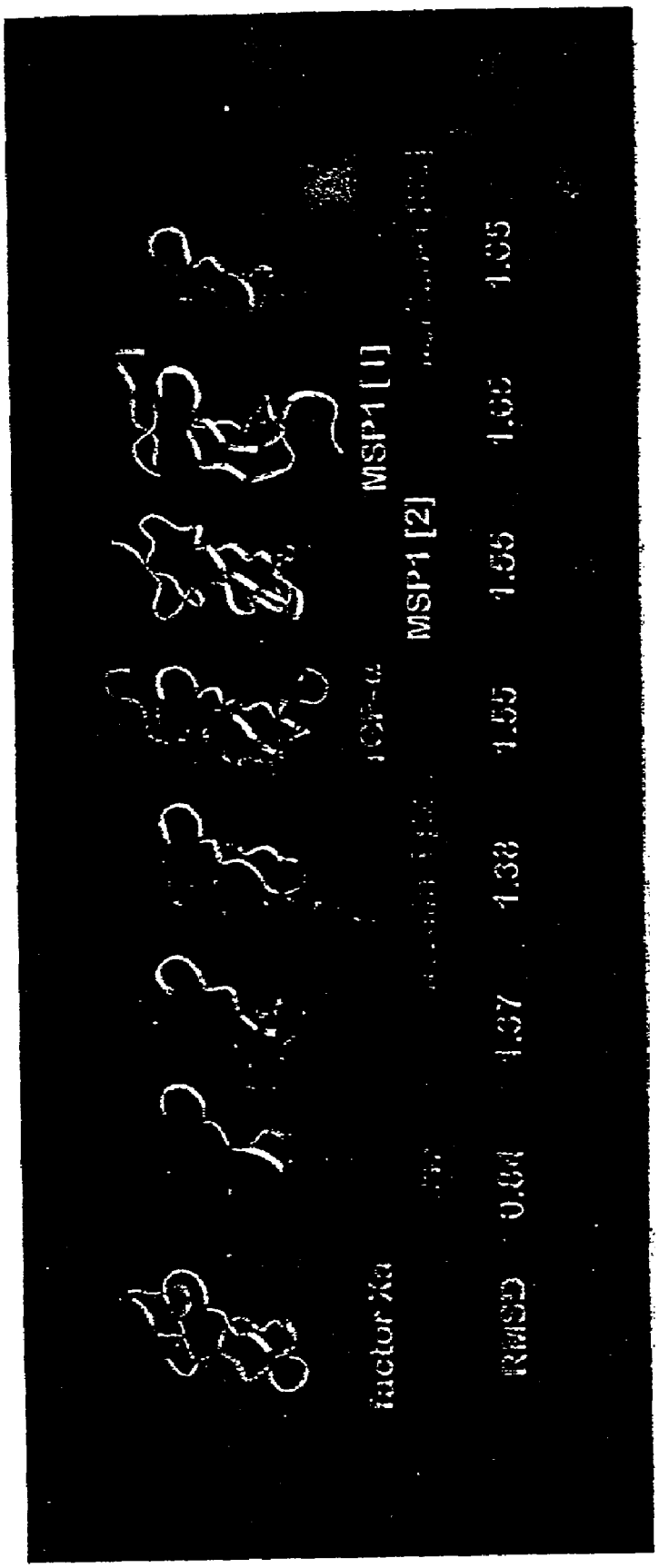

FIG. 5—Alignment of typical EGF-like family members with the fitpdb program, using the 14 amino acid "reduced core" consensus (Bersch et al., 1998) (see FIG. 1). The aligned backbone segment in each structure is white. The structures are aligned relative to the most representative structure of the group (factor Xa), with increasing divergence from left to right. Numbers indicate the rmsd value of the aligned C, N, C$_\alpha$ atoms. PDB identification codes: factor Xa (crystal structure), 1hcg; Complement C1r component, 1apq (14$^{th}$ model); human EGF, legf (11$^{th}$ model); fibrillin-1, domains-32 and -33, 1emn (minimized average structure); transforming growth factor-α, 2tgf (minimized average structure); MSP-1 domains-1 and -2, this study.

Figure 6:
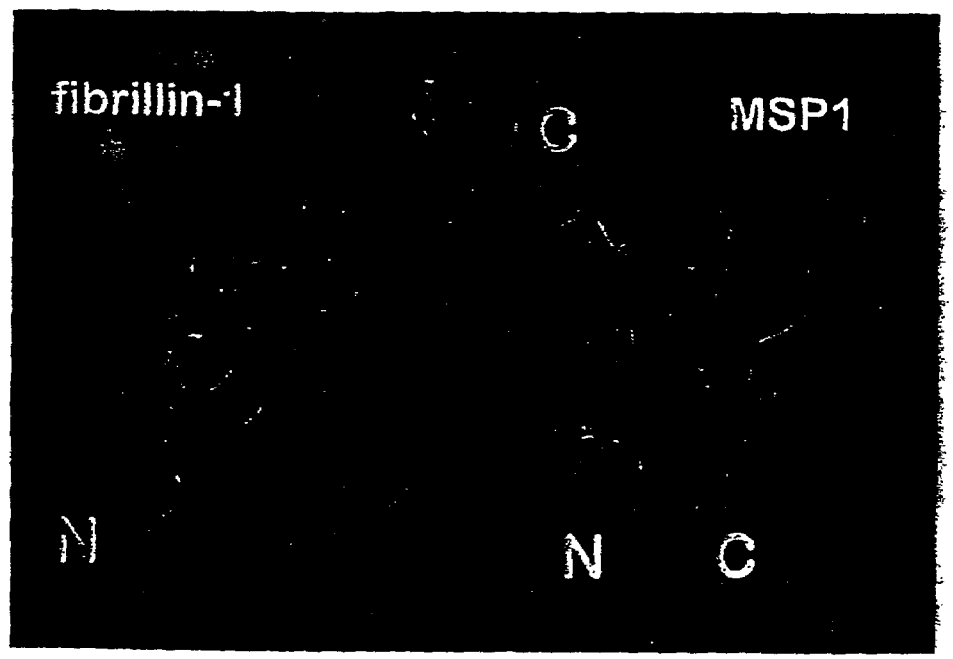

FIG. 6—Backbone ribbon view of fibrillin-1 versus MSP-1 EGF module pair arrangements. Fibrillin-1 (1emn) cyan (domain-32) and magenta (domain-33) (Downing et al., 1996); MSP-1 domain-1 (yellow) and domain-2 (green). Structures were aligned as in FIG. 6 by the core consensus of the N-terminal domain of each pair. The bound Ca$^{2+}$ ions in the fibrillin-1 structure are shown as magenta spheres.

Figure 7:
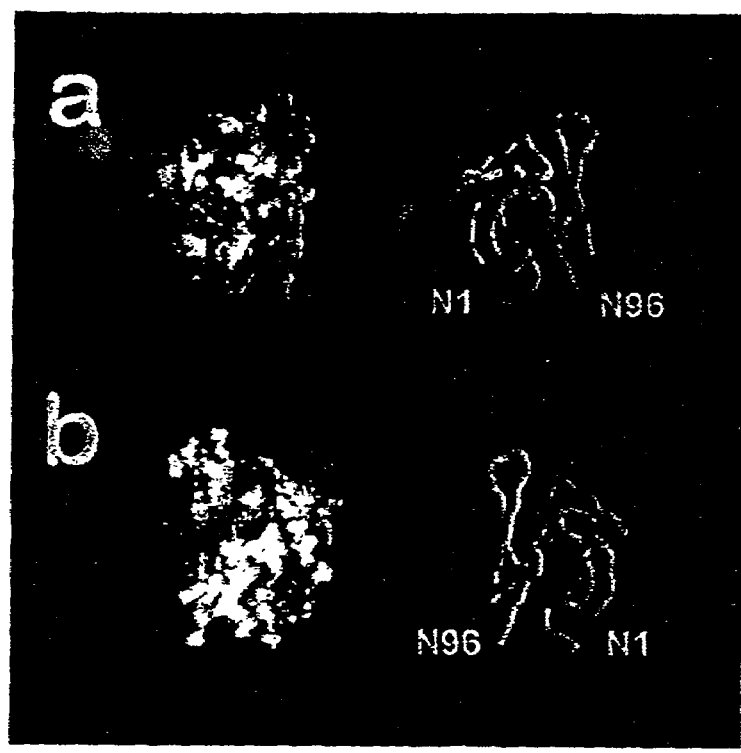

FIG. 7—Two views, a and b, (rotated 180° about the y-axis) of the electrostatic potential surface of the MSP-1 EGF module pair, calculated with GRASP. Red indicates negative charge, blue indicates positive charge, and white is neutral. The orientation of the views is shown by the adjacent worm diagrams.

FIG. 8—CPK model of the MSP-1 C-terminal fragment, showing the location of some mutations that affect binding of monoclonal antibodies. Domain-1 is towards the top and right sides, and domain-2 towards the bottom left.

Figure 9:
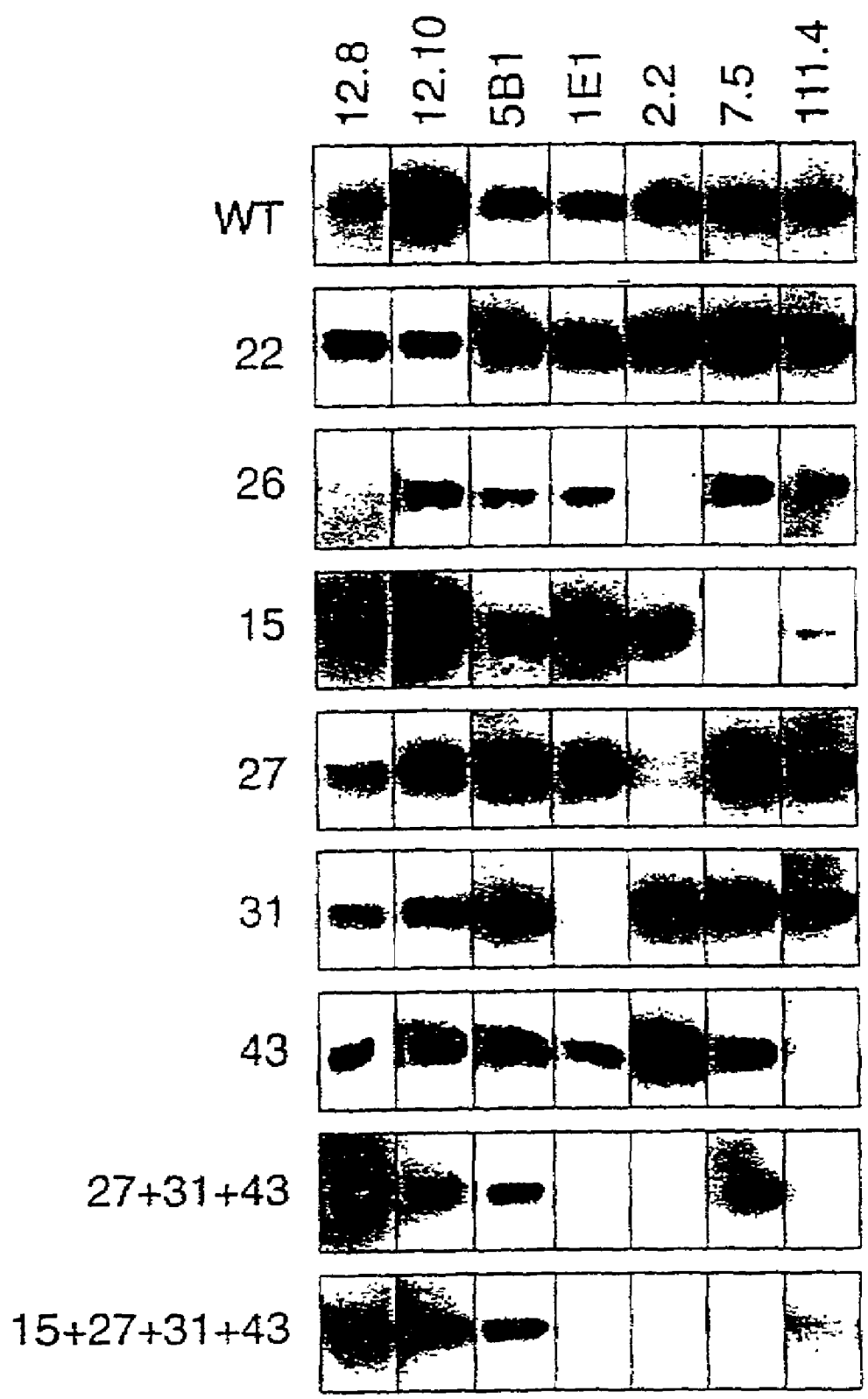

FIG. 9—Examples of the binding of monoclonal antibodies to GST-MSP-1$_{19}$ detected by Western blotting. The binding of each monoclonal antibody to protein based on the wild type sequence and to proteins containing modified sequences is shown. The monoclonal antibodies are shown across the top. On the left is shown the proteins: WT, wild type sequence; 22, Leu22 to Arg; 26, Glu26 to Ile; 15, Asn15 to Arg; 27, Glu27 to Tyr; 31, Leu31 to Arg; 43, Glu43 to Leu; 27+31+43, Glu27 to Tyr and Leu31 to Arg and Glu43 to Leu; 15+27+31+43, Asn15 to Arg and Glu27 to Tyr and Leu31 to Arg and Glu43 to Leu.

FIG. 10—The binding of monoclonal antibodies to GST-MSP-1$_{19}$ detected by BIAcore analysis. The binding of each monoclonal antibody is normalised to 100% binding to protein based on the wild type sequence and the binding of proteins containing modified sequences is expressed as a percentage of this. WT, wild type sequence; 15, Asn15 Arg; 26, Glu26 Ile; 27, Glu27 Tyr; 31, Leu31 Arg; 34, Tyr34 Ser; 43 Glu43 Leu.

FIG. 11—The binding of monoclonal antibodies to GST-MSP-1$_{19}$ containing multiple modifications detected by BIAcore analysis. The binding of each monoclonal antibody is normalised to 100% binding to protein based on the wild type sequence and the binding of proteins containing modified sequences is expressed as a percentage of this. WT, wild type sequence; The combinations contain 3 mutations [27+31+43], or 4 mutations ([27+31+34+43] and [15+27+31+43]), at each site the changes are those identified in FIG. 10.

Figure 12:
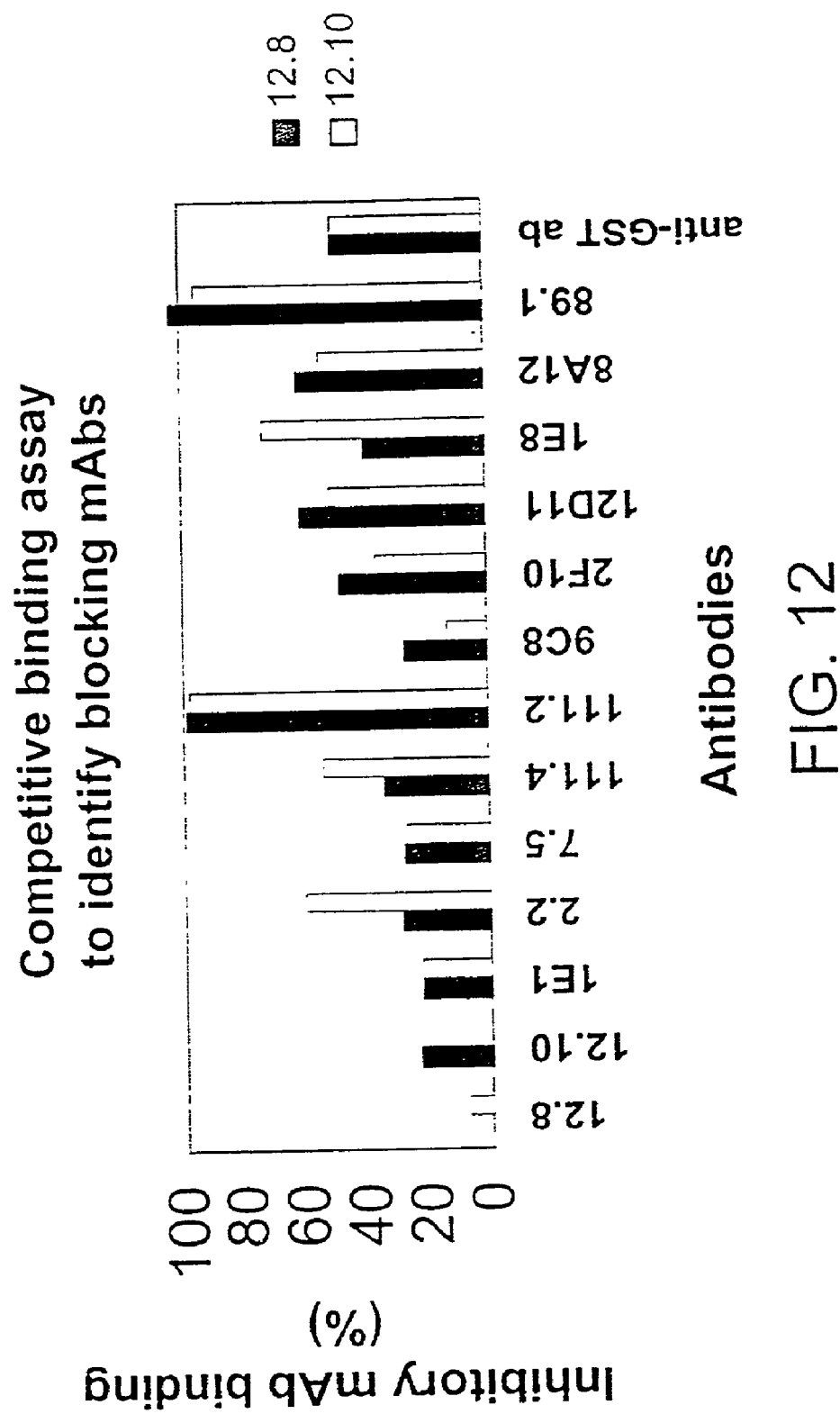

FIG. 12—Identification of blocking antibodies using a competitive binding assay and immobilised wild type GST-MSP-1$_{19}$. The ability of antibodies to compete with the binding of mAbs 12.8 and 12.10 to GST-MSP-1$_{19}$ was measured using BIAcore analysis. Individual antibodies (x-axis) were bound to the antigen and then the amount of either 12.8 or 12.10 (inhibitory mAb) that could subsequently bind was quantified. The amount of binding is presented as a percentage of the total amount of either 12.8 or 12.10 bound in the absence of pre-incubation with another antibody.

Figure 13:
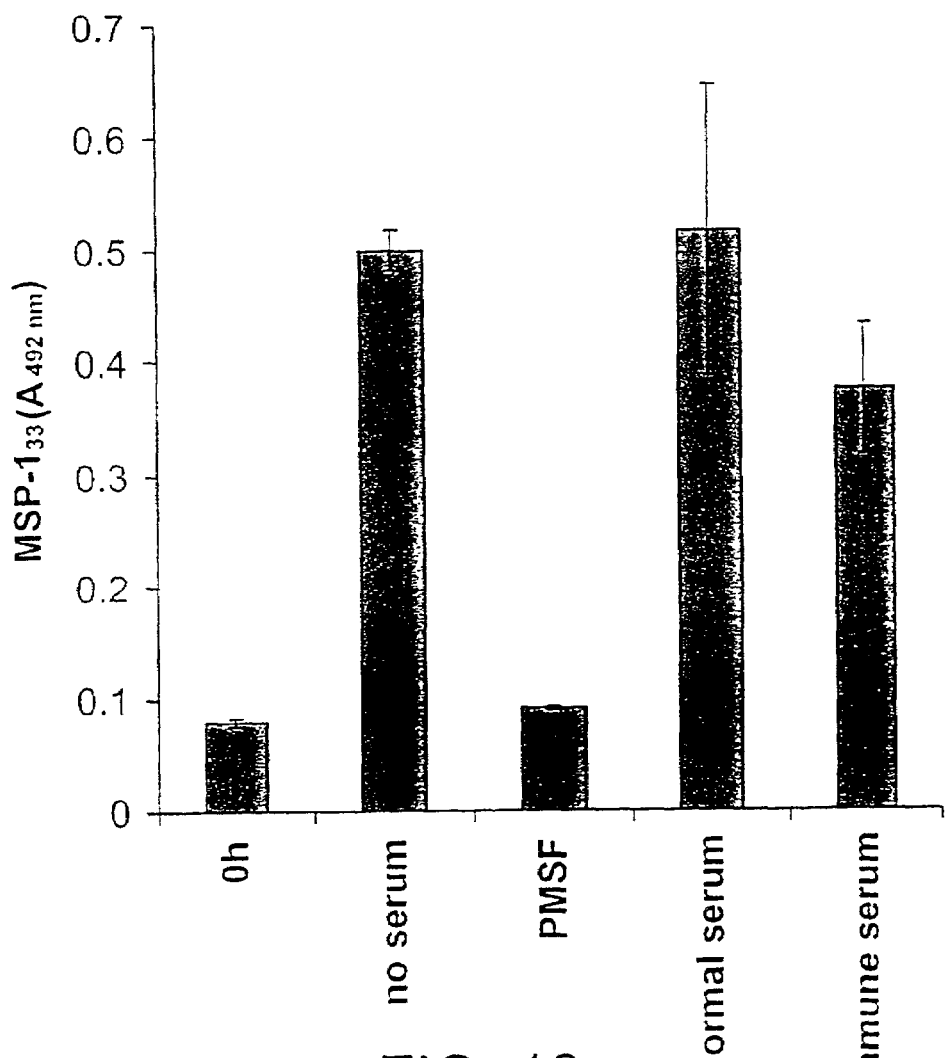

FIG. 13—Antibodies induced by immunisation with a modified recombinant MSP-1$_{19}$ assayed for their ability to inhibit secondary processing. Washed 3D7 merozoites were either analysed directly without incubation (0 h) or incubated for 1 hour at 37° C. in the presence of no serum (no serum), 1 mM PMSF as a control for complete inhibition, normal rabbit sera (normal serum), or serum from a rabbit immunised with the 15+27+31+43 modified protein (immune serum), all at 1:10 dilution in reaction buffer. The level of MSP-1$_{33}$ released into the supernatant as a results of secondary processing was measured using an ELISA method and is represented by Absorbance at 492 nm.

FIG. 14. *Pichia pastoris* codon preference table used for input to the CODOP program.

FIG. 15. DNA and protein sequences for the optimized synthetic MSP142 gene. A: Complete sequence designed for optimum codon usage and expression in *P. pastoris* (SEQ ID NO. 4). B: Sequence of the synthetic MSP-119 construct in the expression vector pPIC9K-Hxa. Uppercase letters: vector sequences, including the His$_6$ tag and factor Xa cleavage site (LEGR). Lowercase letters: synthetic MSP-119 coding sequence (SEQ ID NO. 5). The cloned sequence in located at the SnaBI restriction site of the pPIC9K sequence. C: Expressed protein sequence of the synthetic MSP-119 construct (SEQ ID NO. 6). The sequence shown is produced as a fusion to the pPICK α-factor secretion signal, following the kex2/STE13 processing sites. The synthetic MSP-119 is in bold-face type. D: Sequence of the MSP-133 construct. The cloned sequence is located at the SmaI site of the pUC118 vector (SEQ ID NO. 7). E: Predicted protein sequence of the synthetic MSP-133 construct translation product (SEQ ID NO. 8).

Figure 16:
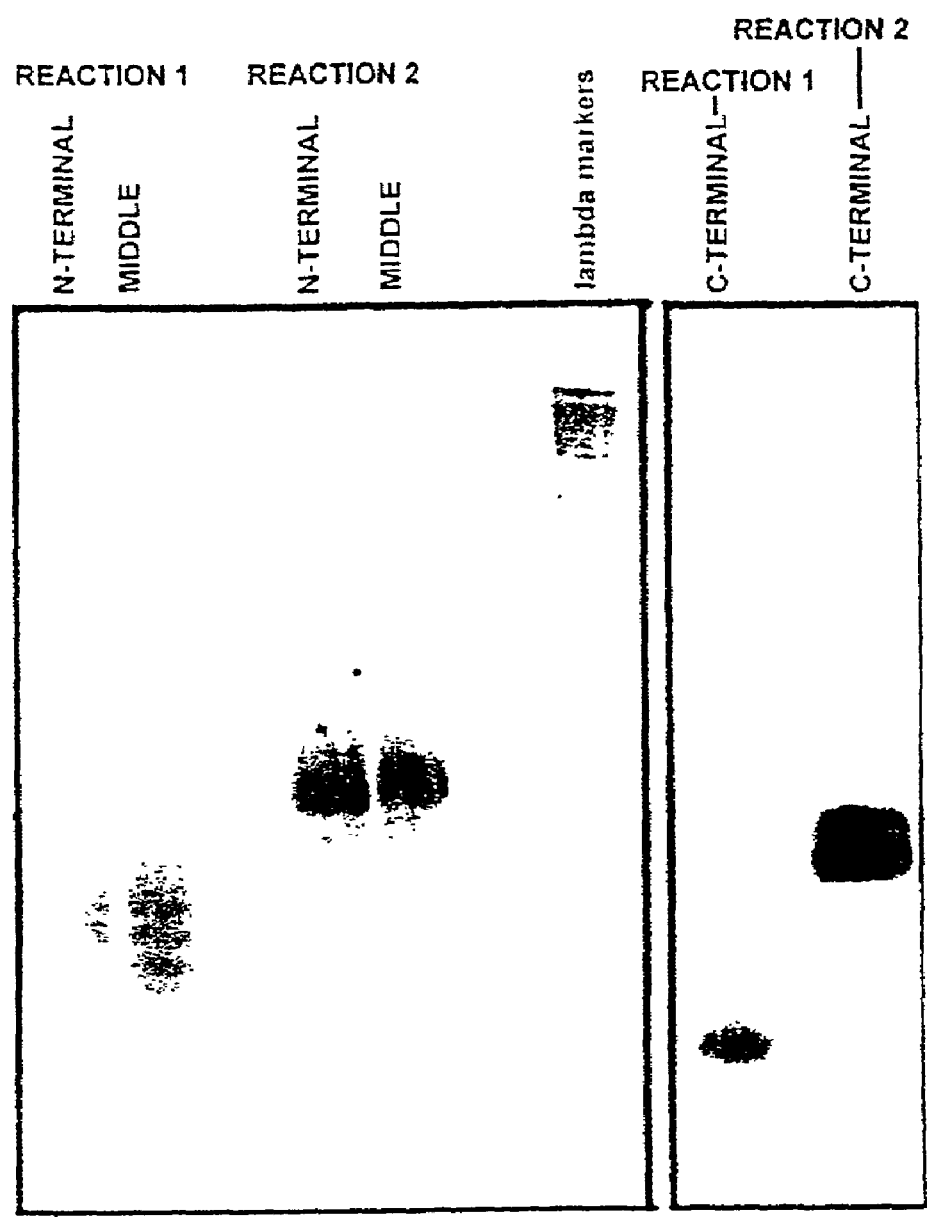

FIG. 16. Gene assembly PCR reactions for the MSP-133 and MSP-119 sequences. Reaction 1: 10 μL aliquots of the assembly reactions. Reaction 2: 20 μL aliquots of the amplification reactions. The N-terminal and middle fragments were subsequently spliced together to form the MSP-133 synthetic construct. The C-terminal fragment synthesis reactions produced the optimized MSP-119 construct.

FIG. 17. Expression of the synthetic MSP-119 protein in *P. pastoris*. Lanes 1–6: trichloroacetic acid precipitates of secreted recombinant protein from culture supernatants, without further purification (5 μL each). Samples from duplicate cultures of three independent transformants. Lane 8,9: purified, deglycosylated MSP-119 produced from the original *P. falciparum* sequence. Lane 7,10: NOVEX molecular weight markers.

FIG. 18. A: {$^1$H/$^{15}$N}-HSQC spectrum of the protein (2.5 mM) expressed from the optimized synthetic MSP-119 gene. B: Control {$^1$H/$^{15}$N}-HSQC of deglycosylated protein (2.2 mM) expressed from the original *P. falciparum* sequence (Morgan et al., 1999).

EXAMPLES

Materials and Methods

Protein Expression and Stable-isotope Labelling for NMR

The coding sequence of the MSP-1 C-terminal fragment was cloned by polymerase chain reaction with Vent polymerase (New England Biolabs) from a plasmid containing the *Plasmodium falciparum* strain T9/94 fragment (Blackman et al., 1991), using primers that included codons for a 6 residue N-terminal His tag (CACCATCATCATCATCAC, SEQ ID NO 14), and inserted into the SnaBI restriction site of the pPIC9K vector (Invitrogen). The sequence corresponds to residues 1526–1621 of the SWISS-PROT entry MSP1 PLAFW (accession number P04933). This produced an α-factor fusion protein with the sequence . . . KR/EA/EA/YHHHHHHNISQ (SEQ ID NO 15) . . . SSSN (SEQ ID NO 16), where the slashes indicate kex2 and STE13 processing sites. High copy number transformants of the methylotrophic yeast *Komagataella* (*Pichia*) *pastoris* protease-deficient strain SMD1168 (his4 pep4) were isolated by screening for high G418 resistance (Clare et al., 1995).

A Mut$^+$ transformant was grown at 29.4° C. in a shaker-incubator in buffered minimal medium (100 mM potassium phosphate, pH 6.0, yeast nitrogen base (0.34% w/vol) (DIFCO: YNB without amino acids and without $(NH_4)_2SO_4$), biotin ($4 \times 10^{-5}$% w/vol), Sigma antifoam 289 (0.01% vol/vol), and carbon and nitrogen sources as described below. Unlabelled samples were initially grown in medium containing 1% w/vol $(NH_4)_2SO_4$ and 1% w/vol glycerol, and induced by transfer to medium containing 0.5% $CH_3OH$ as the carbon source. Labelled samples were initially grown in medium containing 0.2% w/vol [$^{15}$N]—$(NH_4)_2SO_4$ (Isotech), and 0.5% w/vol glucose or [$^{13}C_6$]-glucose (Isotech), and induced by transfer to medium containing as carbon source 0.5% w/vol $CH_3OH$ or [$^{13}$C]—$CH_3OH$ (Isotech). The initial cultures were grown in 150 ml to a density of ~10 $OD_{600}$, then harvested and resuspended in methanol medium at 1 $OD_{600}$ in a volume of 1.5 L. Methanol-induced cultures were grown for 4 d, with daily addition of 7.5 ml $CH_3OH$ or [$^{13}$C]—$CH_3OH$, to a final density of ~18 $OD_{600}$. This protocol produced a maximum yield of 24 mg/L of purified, $^{13}$C/$^{15}$N uniformly labelled protein at the final stage (see below). The YNB-based medium produced about 3-fold higher yields than the FM22 medium (Laroche et al., 1994), for stable-isotope labeling of the MSP-1 C-terminal fragment.

Cells were removed by low-speed centrifugation, protease inhibitors added (COMPLETE™ tablets, Boehringer-Mannheim; 1 tablet/500 ml supernatant), and the supernatant was filter-sterilized. The supernatant was concentrated ~20-fold by ultrafiltration in a stirred cell (Amicon, YM3 membrane) at 4° C. The pH was adjusted to 7.25 with KOH, and the partially N-glycosylated MSP-1 fragment was deglycosylated for 72 h at 37° C. with 5000 U PNGaseF (New England Biolabs). The carbohydrate was completely removed (as shown by electrophoresis and mass spectrometry), with the Asn1 residue presumably converted to Asp in the process. The supernatant was clarified by low-speed centrifugation, 5 M NaCl was added to a final concentration of 0.3 M, and the sample was applied to a 2 ml Ni-NTA affinity column (QIAGEN), washed, and eluted with 250 mM imidazole according to manufacturer's instructions. The eluate was dialyzed against 50 mM sodium phosphate (pH 6.5), 50 mM NaCl, and then passed through a 1 ml Hi-Trap Q anion exchange resin (Pharmacia) to remove misfolded MSP-1 that bound to the column. The MSP-1 fragment was characterized by Western blotting and electrospray mass spectrometry (data not shown). Two principal species of mass 11607 and 11807 Da were observed corresponding to the expected fragment, as well as a fragment with an additional N-terminal Glu-Ala dipeptide resulting from incomplete STE13 processing of the α-factor secretion signal.

Samples for NMR experiments were prepared in either 90% $H_2O$/10% $D_2O$ with 0.01% w/vol $NaN_3$, or 100% $D_2O$, 50 mM sodium phosphate, 100 mM NaCl at pH 6.5, (pH uncorrected for deuterium isotope effects), at a concentration of 2.1 to 2.6 mM in 0.6 ml. Protein concentration was measured by UV absorbance at 280 nm, using a calculated molar extinction coefficient of 5220 liter mol$^{-1}$ cm$^{-1}$. The protein was demonstrated to be monomeric by equilibrium ultracentrifugation of a 0.12 mM sample in the above buffer at 293 K.

NMR Experiments and Data Processing

Most of the experiments were performed at 298 K, using Varian Unity and Unity-Plus spectrometers operating at 600 MHz and 500 MHz respectively. Details of the multidimensional experiments (Clore & Gronenborn, 1998) and acquisition parameters used for resonance assignments and structure determination are given in Tables A/B and have been submitted to the Protein Data Bank database (PDB Accession No 1CEJ).

All spectra were processed using Felix 95.0 or 97.0 (Biosym/MSI) using a 90 degree- or 72 degree-shifted sinebell-squared window function. Dimensions, zero-filling, and linear prediction details are summarized in Tables A/B and in the submission to the BioMagResBank. Four dimensional and interleaved spectra were processed in Felix using macros written in-house.

Signal assignments: Sequential assignments were made based on connectivities established primarily by CBCA(CO)NH and CBCANH experiments on uniformly $^{13}$C/$^{15}$N labelled protein. Side chain-spin system assignments were made on the basis of data from $^{13}$C/$^1$H-HCCH-TOCSY experiment correlated with information from $^{15}$N/$^1$H-TOCSY-HSQC and $^{15}$N/$^1$H-NOESY-HSQC, and HNHA and HNHB experiments. Assignments were obtained for $^1$H, $^{15}$N and aliphatic $^{13}$C signals for 98% of side-chains and 96% of backbone amide groups. The list of assignments is given in Tables A/B and in the submission to the Protein Data Bank database (PDB Accession No 1CEJ). The $^{15}$N{$^1$H} heteronuclear NOE experiment was carried out as described previously (Kay et al., 1989; Polshakov et al., 1997).

Distance Restraints: NOE- and ROE-derived distance restraints between backbone and side chain amide protons were obtained primarily from the 3D $^{15}$N-NOESY-HSQC, $^{15}$N-ROESY-HSQC, and 4D $^{13}$C-HMQC-NOESY-$^{15}$N-HSQC experiments. Aliphatic to aliphatic proton distance restraints were obtained from a 4D $^{13}$C-HMQC-NOESY-$^{13}$C-HSQC experiment. A 3D $^{13}$C-HMQC-NOESY experiment in $D_2O$ was used to identify aliphatic to aromatic proton NOEs and 2D NOESY experiments were used to measure aromatic to aromatic proton NOEs. Crosspeaks were quantified by volume integration in Felix for 2D and 3D experiments and for the 4D $^{13}$C-HMQC-NOESY-$^{15}$N-HSQC experiment, and from peak height measurements in the 4D $^{13}$C-HMQC-NOESY-$^{13}$C-HMQC spectra. Crosspeaks were classified as strong, medium and weak and these were assigned to distance restraints of 0–2.8, 0–3.6, and 0–5.5 Å. Restraints from backbone amide signals were initially treated in this manner, and then recalibrated more precisely using 3D-$^{15}$N-ROESY-HSQC data into four classes involving maximum distances of 2.6, 3.1, 3.6, and 4.1 Å. Restraints to groups of equivalent or non-stereoassigned protons were treated by $r^{-6}$ summation. Most intraresidue distances (HN-H$_\beta$ and H$_\alpha$-H$_\beta$) were converted to $\chi_1$ angle restraints as described below and these distance restraints were not included in the final list.

Dihedral Angle Restraints: $\chi_1$ angles and stereospecific assignments of β-methylene protons were obtained using the grid-search program AngleSearch, with coupling constant and intraresidue ROE distance information (Polshakov et al., 1995). The coupling constant information was provided by HNHB and HN(CO)HB spectral intensities for $^3J(HN-H_\beta)$ and $^3J(CO-H_\beta)$, and intraresidue distances ($HN-H_\beta$, $H_\alpha-H_\beta$) were obtained from 3D $^{15}N$-ROESY-HSQC and 2D ROESY ($D_2O$) experiments. $^3J(HN-H_\alpha)$ coupling constants were obtained from the HNHA experiment. Residues with positive φ angles (ca. +60 degrees) were identified by large intraresidue $H_\alpha$ crosspeak intensities in the HN(CO)HB experiment, and y angles near −60° degrees from strong $H_\alpha(i-1)$ crosspeaks in the HNHB experiment. Ile and Leu $\chi_2$ angles and Leu δ stereoassignments were derived from the LRCH experiment. Minimum ranges of 40 degrees ($\chi_1$, $\chi_2$) and 50 degrees (φ, ψ) were used to account for errors and local dynamic effects on the coupling constants.

Disulphide Bonding Pattern: An initial set of 20 structures was calculated by simulated annealing using approximately 550 unambiguous NOE-derived distance restraints and 36 $\chi_1$ and φ dihedral angle restraints but with no hydrogen bonding or disulphide bond constraints. The Cys-Cys $S_\gamma$ distances in these structures were examined in order to establish the probable bonding pattern. Prior to the calculations, the formation of disulphide bridges for 4 Cys residues (Cys12-Cys28, Cys78-Cys92) was already established with high probability by the observation of $H_\beta-H_\beta$ NOEs between these pairs of Cys residues. Examination of the initial structures confirmed these disulphide bridges and also indicated a disulphide bridge between residues Cys30 and Cys41. The third disulphide bridge in domain-1 (Cys7-Cys18) could thus be assigned by default, although the structure of the N-terminus was not well-defined by the NMR data. The best six structures in terms of total X-PLOR energy and violations indicated that the average Cys-Cys $S_\gamma$ distance was lowest for the disulphide bonding pattern [1-3, 2-4, 5-6] in each domain, and only this combination allowed all Cys residues to form contacts with a partner <3.5 Å away. Thus, this disulphide bonding pattern was most consistent with the experimental data for both domains, and was imposed (initially as NOE-style distance restraints) in subsequent calculations. The [1-3, 2-4, 5-6] pattern is that expected for an EGF-like domain.

Hydrogen Bonds: Non-exchanging amide groups involved in stable hydrogen bonds were identified in spectra of samples examined in 100% $D_2O$. The corresponding hydrogen bond acceptors were determined by examining the initial structural ensemble, using the Insight II and HBPlus (McDonald et al., 1994) programs, and hydrogen bond distance restraints were included in subsequent calculations. Further hydrogen bonds were identified in a similar manner in iterative calculations. Only 10 backbone hydrogen bonds in the antiparallel β sheets were used as restraints. Two distance restraints were used for each hydrogen bond, 1.7–2.3 Å from proton to acceptor, and 3.0–3.6 Å from donor nitrogen atom to acceptor.

Structure Calculations

All the structure calculations were performed following standard protocols for ab initio simulated annealing from an extended chain using X-PLOR version 3.843 on a Silicon Graphics Origin 200 computer. The initial calculations used an initial temperature of 1000K, and 9000 steps of 5 fs in the restrained molecular dynamics stage. A soft-square potential was used for distance restraints. The SHAKE (Ryckaert et al., 1977) algorithm was employed during molecular dynamics to maintain correct bond lengths. Refinement used a square well potential for restraints, and a final slow cooling of 30000 steps of 4 fs each from 2000K. A modified "parallhdg.pro" force-field parameter set was used, with modifications to parameters for Arg and Pro residues, and for hydrogen bonds (Polshakov et al., 1997). Force constants were 50 kcal mol$^{-1}$ A$^{-2}$ for all distance restraints including hydrogen bonds, and 200 kcal mol$^{-1}$ rad$^{-2}$ for dihedral restraints. The N-terminal sequence including the vector-encoded residues and (His)$_6$ tag was excluded from the structure calculations. All peptide bonds were constrained to be trans. NOE data for all 5 Pro residues showed strong $H_{\alpha(i-1)}$-ProH$_\alpha$ crosspeaks, consistent with the trans peptide conformation.

Initial structures were calculated as described above to determine the disulphide bonding pattern. Then the calculation was repeated with identical NOE-derived distance and dihedral angle restraints, with the addition of 6 distance restraints (1.92–3.12 Å) representing the disulphide bridges. A new set of 50 structures was obtained, from which the best 20 structures were selected. The criteria used for selection were that the structures were below the median value of both total X-PLOR energy and rms NOE difference, and had no dihedral angle violations. The resulting structures had good geometry and between zero and two NOE violations >0.5 Å. These structures were used to assign previously ambiguous NOEs and to determine the hydrogen bonds as described above.

The final structure calculation and refinement used an expanded restraint list including hydrogen bonds, additional dihedral restraints, stereoassignments of β-methylene and Leu δ signals, and more precisely calibrated ROE data (see Table 1). A set of 100 structures was obtained using this list, and 38 structures with 0–2 NOE violations >0.5 Å and no dihedral angle violations >5° were accepted. These 38 structures were refined by the slow-cooling procedure described above, producing a final ensemble of 32 accepted structures with no NOE violations >0.5 Å and no dihedral angle violations >5°. These selection criteria produced an ensemble of structures that extend to the end of the continuum of total potential energies in order to include structures having large scale correlated motions (Abseher et al., 1998). Statistics for the final ensemble are given in Table 1. Coordinates for the 32 refined structures have been deposited in the Brookhaven Protein Data Bank (coordinates ID code 1cej; NMR restraints ID code r1cejmr).

Structures were analyzed during the calculation process using X-PLOR 3.8 (Nilges et al., 1991), PROCHECK-NMR/AQUA (Laskowski et al., 1996), and Insight II for quality of agreement with experimental data, precision, geometry, and energy. Models were aligned with Insight II and fitpdb, and displayed with Insight II, MOLSCRIPT (Kraulis, 1991), and GRASP (Nicholls et al.,1991).

TABLE 1

A: RESTRAINTS SUMMARY

| Number of conformers calculated: 100 | | Number of conformers accepted: 32 | |
|---|---|---|---|
| Acceptance criteria: | | | |
| No distance violation: >0.5 Å | | No dihedral angle violation: >5° | |
| NOE/ROE distance restraints: | | | |
| Intraresidue: 73 | | Sequential: 222 | |
| Medium range (2–4): 90 | | Long range (>4): 185 | |
| Total: 570 | | | |
| Dihedral angle restraints: | | | |
| phi: 25 | psi: 33 | chi-1: 22 | chi-2: 5 | Total: 85 |
| Hydrogen bonds: 10 | | Disulphide bonds: 6 | |

TABLE 1-continued

B: STRUCTURE QUALITY

|  | average | +/- s.d. |
|---|---|---|
| Total X-PLOR energy (kcal mol$^{-1}$) | 168 | 20 |
| NOE X-PLOR energy (kcal mol$^{-1}$) | 21 | 8 |
| rmsd NOE | 0.026 | 0.005 |
| rmsd dihedral angle | 0.236 | 0.095 |
| rmsd bond length | 0.0029 | 0.0002 |
| rmsd bond angle | 0.357 | 0.023 |
| rmsd improper | 0.266 | 0.018 |
| Backbone rmsd of structured region: (69 residues) | | |
| Overall: | 1.05 | 0.28 |
| Domain-1: | 0.81 | 0.32 |
| Domain-2: | 0.83 | 0.35 |
| Ramachandran plot quality (phi/psi angles): | | |
| Most favoured | | 49.5 % |
| Additional allowed | | 42.1% |
| Generously allowed | | 5.6 % |
| Disallowed | | 2.7% |

Monoclonal Antibodies (mABs)

Anti-MSP-1$_{19}$ monoclonal antibodies used in this study were: mouse IgG mAbs 1E1, 1E8, 2F10, 111.2, 111.4 2.2, 5.2, 7.5, 9C8, 12.8, 12.10, 12D11, 117.2, 8A12 (Holder et al., 1985; McBride & Heidrich, 1987; Blackman et al., 1987; Guevara Patiño et al., 1997); and mouse IgM mAb 5B1 (Pirson & Perkins, 1985). Of these, mAbs 12.8, 12.10 and 5B1 are neutralising, inhibitory antibodies and 1E1, 2.2, 7.5, 9C8 and 111.4 are blocking antibodies. Some antibodies such as 111.2 are neither inhibitory nor blocking.

Construction of Modified MSP-1$_{19}$ Clones

The DNA coding the wild type MSP-1$_{19}$ domain of *Plasmodium falciparum* (T9-94/Wellcome strain) MSP-1 has been cloned in expression vector pGEX-3X to produce MSP-1$_{19}$ fused to the carboxy-terminus of the *Schistosoma japonicum* glutathione S-transferase (GST) in *Escherichia coli* (Burghaus & Holder, 1994). Site-directed mutagenesis of MSP-1$_{19}$ DNA sequence was done in either of two ways.

The first method was a modification of the method of Perrin & Gilliland (1990) to carry out polymerase chain reaction (PCR)-mediated site specific mutagenesis. DNA was amplified using the plasmid as a template together with one oligonucleotide to introduce the point mutation and a 5' primer from outside of the MSP-1$_{19}$ sequence. The amplified product was purified after electrophoresis on an agarose gel and used in a second amplification step together with a 3' primer from outside of the other end of the MSP-1$_{19}$ sequence and the plasmid as template. This second PCR product was digested with the restriction enzymes EcoR1 and BamH1 and the product consisting of the modified MSP-1$_{19}$ coding sequence was inserted back into pGEX-3X and the products were used to transform DH5α cells.

The second method used the QuikChange™ Site-directed mutagenesis kit from Stratagene.

Briefly, using the plasmid pGEX-MSP-1$_{19}$ as a template, two complementary synthetic oligonucleotide primers containing the desired point mutation were designed and were extended on the template by temperature cycling with the enzyme Pfu DNA Polymerase. This incorporation of the oligonucleotide primers results in the generation of a mutated plasmid containing staggered nicks in the DNA sequence. Following the temperature cycling, the product was treated with DpnI endonuclease which will digest the methylated parental DNA template and leaves the mutation-containing newly synthesised DNA intact. The DNA incorporating the desired mutation was then transformed into *E. coli* strain DH5α (Life technologies) competent cells where the nicks will be repaired.

Clones were screened by analysis of restriction enzyme digests and by PCR screening of the insert gene. The DNA sequence of the selected mutant clones was confirmed using a PerkinElmer Applied Biosystems ABI 377 automatic sequencer according to the manufacturer's instructions.

Expression of the GST-MSP-1$_{19}$ Fusion Proteins

Expression of GST-MSP-1$_{19}$ was induced with 1 mM isopropyl-β-D-thiogalactopyranoside (IPTG; Melford Laboratories) for 1 hour in the *E. coli* strain TOPP 1 (Stratagene). The cells were then harvested by centrifugation and the cell pellet was resuspended in cell lysis buffer (50 mM Tris-HC1/1 mM EDTA pH 8.0 containing 0.2% (v/v) Nonidet P40 (NP40; BDH). Phenylmethylsulphonyl fluoride (PMSF; Sigma) in isopropanol was added to a final concentration of 1 mM. The cell suspension was sonicated, on ice, using VibraCell sonicator (Sonics & Materials) at 50% duty cycle for 3 min (six 30 sec pulses with 30 sec in between). The cell lysate was centrifuged at 65000×g for 1 hour at 4° C. Supernatant containing soluble GST-fusion protein was applied to a glutathione-agrose column (Sigma) and the GST-fusion protein was eluted with 5 mM reduced glutathione. The eluted GST-fusion protein was dialysed extensively against phosphate buffered saline (PBS) at 4° C.

SDS-PAGE and Western Blotting

Proteins were analysed by polyacrylamide gel electrophoresis in the presence of sodium dodecyl sulphate (SDS-PAGE). Samples were solubilised in SDS-PAGE buffer without reducing agents, then fractionated on a homogeneous 12.5% polyacrylamide gel. The pre-stained low range molecular mass markers (24–102 kDa) from Bio-Rad were used as markers. When required, SDS-PAGE-fractionated polypeptides were either stained with Coomassie Brilliant Blue R-250 (CBB; Sigma) or electrophoretically transferred to Optitran BA-S 83 reinforced nitrocellulose (Schleicher & Schull, 0.2 μm pore size) for analysis by western blotting. Blots were blocked with 5% BSA, 0.5% Tween 20 in PBS (PBS-T) for 1 h at room temperature, then washed in PBS-T. Blots were probed with first antibodies for 2 h at room temperature, washed 3 times in PBS-T, and then incubated in 1/1000 dilution of horse radish peroxidase (HRP)-conjugated sheep anti-mouse IgG (H+L) (ICN Immunobiologicals) or Goat anti-mouse IgM (μchain) (Sigma) for 1 h at room temperature. Blots were then washed 3 times in PBS-T and developed using Super Signal Substrate (Pierce) as HRP substrate for 1 min. Blots were then placed in plastic wrap and exposed to X-ray film (XB-200, X-ograph Imaging Systems). The films were processed with an Agfa Gevamatic60 film processor (Agfa).

Analysis of Antibody-Antigen Interaction Using a BIAcore Machine

GST-MSP-1$_{19}$ containing either the wild type or various modified sequences was used to coat a carboxymethyl dextran hydrogen sensor chip by the following methodology. The binding of the GST-MSP-1$_{19}$ was via amino groups using EDC/NHS chemistry. Immobilisation was done with the amine coupling kit (Pharmacia BIAcore). The CM dextran surface was activated with 50 μl of 200 mM 1-ethyl-3-(3-dimethylaminopropyl) carbodiimide (EDC) and 5 mM N-hydroxysuccinamide (NHS) for 10 min. GST-MSP-1$_{19}$ was then coupled to the BIAcore sensor surface using 50 μl of a solution at 100 μg ml$^{-1}$ in coating buffer (0.01M sodium acetate buffer, pH 3.5) for 10 min. Unreacted carboxyl groups were blocked by adding 50 μl 1 M ethanolamine, pH 8.5 for 10 min. The cells were washed with two pulses of 20 μl 10 mM glycine-HCl, pH 2.8 for 8 min in total to remove any non-covalently bound protein. The immobilisation procedure was carried out at a flow rate of 5 μl min$^{-1}$. Measurements were performed on the BIAcore 2000 instrument.

Results

EXAMPLE 1

Resonance Assignments, NMR Restraints and Structure Determination

The assignments and restraints were obtained as described in Materials and Methods using a range of multidimensional heteronuclear experiments with $^{13}C/^{15}N$ uniformly labelled protein. Sample spectra from 3D and 4D experiments showing NOE connections to the Lys35 backbone amide NH proton, resolved and unambiguously assigned using the $^{13}C$ chemical shift information, are shown in FIG. 2. The distance, dihedral angle and hydrogen bond restraints used in the final set of structure calculations are summarized in Table 1. A total of 570 unambiguously assigned distance restraints, 85 dihedral angle restraints, and 10 hydrogen bonds were used in the final set. The assignments and restraint list shown in Table A have been submitted to the BioMagResBank database. Three disulphide bonds, with the (1-3, 2-4, 5-6) pattern for each domain were experimentally determined from the NMR data in preliminary calculations as described in Materials and Methods, and these were also included in the final refinement. A final set of 32 models was calculated and refined using these restraints and these structures are shown in FIG. 3 superimposed on the backbone of the representative structure $S_{rep}$. Table 1 shows that all 32 models have good geometry and are in good agreement with the experimental data with no NOE violations >0.5 Å and no dihedral angle violations >5°. The atomic rmsd value for the backbone atoms of the well-structured region (residues 15–64, 74–92) is 1.05 Å (see Table 1). The local backbone rmsd is highest at the N-terminus (up to Cys12), in the loop Glu65-Lys73, and following Cys92 at the C-terminus. The Ramachandran plot quality is typical of that found for other EGF structures (Doreleijers et al., 1998).

Description of the Structure

EGF-domains

Analysis of the final ensemble by PROCHECK-NMR indicated that each domain contains a major stretch of antiparallel β-sheet containing the third and fourth Cys residues of each domain, as expected for an EGF-like fold, as well as an additional minor antiparallel β-sheet at the C-terminal end of domain-1, similar to some (but not all) EGF family members. These secondary structure features, together with the disulphide bonding patterns, can be seen in FIG. 4. There is also a well-defined type II tight turn in domain-1, with a hydrogen bond from Tyr 34NH proton to Leu31 carbonyl oxygen. The normally conserved EGF consensus Gly residue in the tight turn is replaced in domain-1 by a residue with a positive φ angle (Asn33), while the conserved aromatic residue is present (Tyr34). There is a probable hydrogen bond between Leu 31NH proton to Asn15 carbonyl oxygen. Domain-2 contains two turns preceding the major β-sheet, (Asn53-Cys56, Asp57-Ala60), and a final bend from Leu86-Phe91 with a probable hydrogen bond from Asp57 NH proton to the carbonyl oxygen of Ile90 or Gly89. A surface-exposed loop from Pro81 to Pro85 replaces the tight turn, while the aromatic residue is not conserved. The large loop at the end of the major b-sheet (Glu65-Lys73) is relatively disordered, and high mobility for the segment Gly68-Gly71was confirmed by backbone amide $^{15}N\{^{1}H\}$ heteronuclear NOE measurements (Barbato et al., 1992). The heteronuclear NOE values are dramatically reduced for residues in this region. At the N-terminus: the low NOE intensities correspond to increased mobility compared with the rest of the protein. The interdomain linker region from Pro45 to Pro47 is distinct from other EGF-like module pairs. The conformations of the disulphide bridges between Cys30-Cys41 in domain-1, and the three Cys-Cys bonds in domain-2 are all left handed spirals (Richardson, 1981). Bridges between Cys30-Cys41, Cys56-Cys76, and Cys78-Cys92 are particularly close to their equivalents in the blood coagulation factor Xa structure (1hcg). The conformations of the first two disulphide bridges in the relatively disordered N-terminal segment of domain-1 were not determined.

FIG. 5 shows the backbone C, N, $C_\alpha$ atom alignments of the two MSP-1 C-terminal fragment domains made with typical examples of EGF-like domains from several proteins, using the fitpdb program. Pairwise alignments showed that the two domains from MSP-1 are more similar to the factor Xa structure and its close relative from C1r, than to each other or to the other structures tested. The rmsd values for MSP-1 domains compared to factor Xa are comparable to those of the more distantly related structures fibrillin-1 and transforming growth factor-α.

The overall fold of each MSP-1 domain is thus similar to typical EGF family members, with the turns following the fifth Cys residue roughly equivalent, in spite of the divergence from the EGF consensus (C(5)xxGα) where α is a Phe or Tyr residue. Although some of the external loops are disordered, the scaffold is quite stable, as indicated by the non-exchangeable backbone amides (see above and in Protein Data Bank/BioMagResBank submission for details).

Unlike many EGF-like domains such as fibrillin-1, the MSP-1 C-terminal fragment lacks the conserved EGF $Ca^{2+}$-binding sequence and there was no evidence of $Ca^{2+}$ binding to the MSP-1 C-terminal fragment. The 2D $^1H$-NOESY spectra were virtually identical in the absence or presence of 20 mM $CaCl_2$, indicating that any binding that might occur has, at most, only a small affect the overall structure.

Domain Interface and Surface

The most striking feature of the MSP-1 C-terminal fragment structure is the interface between the domains, which consists of several nonpolar amino acids (Phe19, Leu31, Leu32, Leu86, Phe87, Ile90 and Phe91) involved in hydrophobic interactions. These residues join the base of the major β-sheet and the tight turn in domain-1 with the final bend from residue 86 to 91 in domain-2. The domain interactions result in the domains forming a U-shaped structure which contrasts with structures observed for other pairs of EGF domains (Downing et al., 1996; Brandstetter et al., 1995). For example, in fibrillin-1, the interface between EGF domains 32 and 33 is largely formed by a shared $Ca^{2+}$ ligation site (Downing et al., 1996), and the overall structure resembles a rigid rod, with distant N- and C-termini. This contrasts with MSP-1 where the EGF-like domains are folded against each other so that their termini are relatively close together. A comparison of fibrillin-1 and MSP-1 EGF module pairs is shown in FIG. 6. Although both termini of the MSP-1 C-terminal fragment are somewhat disordered, NOE contacts were observed between nuclei in the two ends. The proximity of the C- and N-terminal positions may be significant, since it suggests that the proteolytic processing site that produces the C-terminal 96 amino acid fragment may be very close to the GPI membrane attachment site at or near residue 96. This proximity is consistent with the idea that a membrane-bound *Plasmodium* proteinase is responsible for secondary processing.

The electrostatic potential surface of the MSP-1 C-terminal fragment is shown in two views in FIG. 7. The surface in FIG. 7a is highly charged, especially in the protruding loop regions 23–27, 35–40 and 64–66. The surface in FIG. 7b contains more neutral hydrophilic residues as well as a small hydrophobic patch from Pro85-Phe87 near the center of the surface. In the future, such information could assist in understanding how these different surfaces may be involved in interactions with the rest of the MSP-1 precursor, the processing proteinase, other proteins on the merozoite surface, or unknown targets on the erythrocyte or parasite vacuolar membrane surfaces.

Primary Sequence Conservation

The residues involved in the hydrophobic domain interface in *P. falciparum* are also shown in FIG. 1, together with corresponding residues in MSP-1 of the less virulent human malaria parasite, *P. vivax* (Del Portillo et al., 1991; Gibson et al., 1992). Extensive conservation of the interface residues (with conservative substitutions) suggests that *P. vivax* and perhaps other *Plasmodium* species as well, may have a similar U-shaped EGF module pair arrangement. Another feature of the *P. vivax* sequence, also seen in other *Plasmodium* species, is the single disulphide bond deficiency in the first EGF-like domain resulting from the absence of cysteine residues equivalent to the *P. falciparum* Cys12 and Cys28.

*P. falciparum* Dimorphic Sites

Five dimorphic sites have been observed in the *P. falciparum* MSP-1$_{19}$ C-terminal fragment from different isolates (Qari et al., 1998). Several observations can be made about the position of these sites on the MSP-1 structure. Two sites, Gln14/Glu14 and Lys61/Thr61, involve residues in relatively well-structured backbone regions, with surface-exposed hydrophilic or charged side-chains. A pair of adjacent sites, with the sequence variants Asn70-Gly71/Ser70-Arg71, occurs in the disordered loop of domain-2, within a segment (residues 68–71) that has been shown to be highly mobile. The region from Glu65 to Lys73 also appears to be the most variable region among different *Plasmodium* species (Daly et al., 1992; Holder et al., 1992). Finally, the fifth site has a substitution between hydrophobic residues (Leu86/Phe86). This partially-exposed side-chain is located at the hydrophobic domain interface, and the conservative substitution is consistent with a role in this interaction.

EXAMPLE 2

Mutation and Monoclonal Antibody Binding Studies

As a step towards understanding antibody interactions with the MSP-1 C-terminal fragment, the effect of engineered point mutations (within domain-1) on antibody binding has been studied. Amino acid substitutions were made that consisted of radical changes. These radical changes consisted of, for example, replacing an aliphatic residue with a charged polar residue, replacing a positively charged side chain with a negatively charged side chain, replacing an amino acid with a large side chain with an amino acid with a smaller or no side chain (glycine), replacing a polar amino acid with a charged polar amino acid, replacing a polar amino acid with an aromatic amino acid, replacing a large aromatic amino acid with an amino acid with a small side chain, and replacing cysteine residues that are involved in disulphide bonds.

Four individual amino acid substitutions shown in FIG. 8, each completely abolish binding of one or more mAbs to the mutant fragment, as detected by Western blotting. The Glu26 mutation, shown in cyan, is closest to the N-terminal proteolytic processing site (magenta) at Asn1, and is the only one of this group of mutations that affects binding of a processing-inhibitory antibody, i.e. one that is capable of preventing both proteolytic processing of the MSP-1 precursor and erythrocyte invasion in vitro. The other three mutations abolish binding of blocking antibodies that bind to the native C-terminal fragment and interfere with the binding of processing-inhibitory antibodies.

Additional mutations were made based on the immunochemical analyses and the tertiary structure of the molecule, and the binding of the mAbs was assessed by western blotting and BIAcore analysis. The results are summarised in Table 2. The results of the binding of selected mAbs to the modified proteins as detected by Western blotting are shown in FIG. 9, and by BIAcore analysis in FIG. 10. Some individual amino acid changes have no effect on the binding of any of the mAbs tested (for example Leu22 to Arg). Other substitutions affect the binding of one or more mAbs.

Of particular interest are those changes that prevent the binding of blocking antibodies but have no effect on the binding of the inhibitory antibodies. For example, replacement of Asn15 by Arg prevents the binding of mAb 7.5, replacement of Glu27 by Tyr prevents the binding of mAb 2.2, replacement of Leu31 by Arg prevents the binding of mAb 1E1, replacement of Tyr34 by Ser prevents the binding of mAb 7.5, and replacement of Glu43 by Leu prevents the binding of mAb 111.4.

Several combinations of substitutions that prevent the binding of blocking antibodies but do not affect the binding of inhibitory antibodies were made in single proteins (Table 2 and FIG. 11). In the first Glu27→Tyr, Leu31→Arg and Glu43→Leu were combined, in the second Glu27→Tyr, Leu31→Arg, Tyr34→Ser, and Glu43→Leu were combined, and the third Asn15→Arg, Glu27→Tyr, Leu31→Arg and Glu43→Leu were combined. None of these modified proteins bound any of the blocking antibodies but continued to bind the inhibitory antibodies. We propose that the mutant proteins will induce a polyclonal response that is more inhibitory than that induced by the wild type protein.

The modified recombinant proteins will also be used to affinity select antibodies from pooled serum from individuals exposed to malaria. We hypothesise that the modified proteins will select less blocking antibody than the wild type protein and that therefore these selected antibodies will be more effective in inhibiting parasite invasion in vitro and secondary processing.

In the first EGF-like domain of MSP-1 from the rodent, primate and *P. vivax* malaria parasites, cysteines 2 and 4 are not present. We have replaced this cysteine pair (Cys12 and Cys28) in the *P. falciparum* protein. This does not have appear to have any effect on the binding of any of the inhibitory antibodies, but does abolish the binding of the blocking antibody mAb 2.2. We propose that one reason why the proteins from these other malaria parasites are more immunogenic is that T cell recognition is more effective or that processing by antigen processing cells proceeds by a different degradation pathway that drives the fine specificity of the antibody response in a more productive direction (see for example Egan et al., 1997). Removal of the cysteine pair may improve the immunogenicity of the modified protein and this will be assessed by measuring the level of antibodies induced by the *P. falciparum* protein without the two cysteines with the level of antibodies induced by the wild type protein.

TABLE 2

The location of amino acid sequence changes and their effect on the binding of monoclonal antibodies

| Position | Amino acid Wild type | mutant | 12.8 | 12.10 | 5B1 | 1E1 | 2.2 | 7.5 | 111.4 | 111.2 | 9C8 | 2F10 | 12D11 | 117.2 | 5.2 | 1E8 | 8A12 |
|---|---|---|---|---|---|---|---|---|---|---|---|---|---|---|---|---|---|
| 6 | Gln | Ile | ++ | ++ | ++ | ++ | + | + | ++ | ++ | ++ | ++ | ++ | ++ | ++ | ++ | ++ |
| 14 | Gln | Gly | ++ | ++ | ++ | ++ | ++ | + | + | ++ | ++ | ++ | ++ | + | ++ | ++ | ++ |
| 14 | Gln | Arg | ++ | ++ | ++ | ++ | ++ | + | + | ++ | + | ++ | ++ | + | ++ | ++ | ++ |
| 15 | Asn | Arg | ++ | ++ | ++ | ++ | ++ | − | + | ++ | ++ | ++ | ++ | ++ | ++ | ++ | ++ |
| 20 | Arg | Glu | + | ++ | + | ++ | + | + | ++ | + | + | ++ | + | + | ++ | + | ++ |
| 22 | Leu | Arg | ++ | ++ | ++ | ++ | ++ | ++ | ++ | ++ | ++ | ++ | ++ | ++ | ++ | ++ | ++ |
| 24 | Glu | Lys | + | ++ | ++ | ++ | ++ | ++ | ++ | ++ | + | ++ | ++ | ++ | ++ | + | ++ |
| 25 | Arg | Gly | ++ | ++ | ++ | ++ | + | ++ | ++ | ++ | ++ | ++ | ++ | ++ | ++ | + | ++ |
| 26 | Glu | Ile | − | ++ | + | ++ | − | ++ | ++ | ++ | ++ | ++ | ++ | ++ | + | + | + |
| 27 | Glu | Tyr | ++ | ++ | ++ | ++ | − | ++ | ++ | ++ | ++ | ++ | ++ | ++ | ++ | ++ | + |
| 29 | Lys | Ser | + | ++ | ++ | ++ | + | + | ++ | ++ | ++ | ++ | ++ | ++ | ++ | ++ | ++ |
| 31 | Leu | Arg | + | ++ | ++ | − | ++ | ++ | ++ | − | − | ++ | ++ | ++ | ++ | ++ | + |
| 32 | Leu | Arg | ++ | ++ | ++ | ++ | ++ | ++ | ++ | ++ | ++ | ++ | ++ | ++ | ++ | ++ | ++ |
| 33 | Asn | Ile | ++ | ++ | ++ | ++ | ++ | ++ | ++ | + | ++ | ++ | ++ | ++ | ++ | ++ | ++ |
| 34 | Tyr | Ser | ++ | ++ | ++ | + | + | + | + | ++ | + | ++ | + | + | ++ | ++ | ++ |
| 34 | Tyr | Ile | ++ | ++ | ++ | + | ++ | + | + | ++ | ++ | ++ | ++ | ++ | ++ | ++ | ++ |
| 35 | Lys | Ile | ++ | ++ | ++ | ++ | ++ | ++ | ++ | ++ | ++ | ++ | ++ | ++ | ++ | ++ | ++ |
| 36 | Gln | Gly | ++ | ++ | ++ | ++ | ++ | ++ | ++ | ++ | ++ | ++ | ++ | ++ | ++ | ++ | ++ |
| 37 | Glu | Ile | ++ | ++ | ++ | ++ | ++ | ++ | ++ | ++ | ++ | ++ | ++ | ++ | ++ | ++ | ++ |
| 39 | Asp | Thr | ++ | ++ | ++ | ++ | ++ | ++ | + | ++ | ++ | ++ | ++ | ++ | ++ | ++ | ++ |
| 40 | Lys | Ile | + | ++ | + | + | ++ | ++ | + | + | + | + | + | + | ++ | + | ++ |
| 43 | Glu | Leu | ++ | ++ | ++ | + | ++ | + | − | ++ | + | ++ | + | + | ++ | ++ | + |
| 48 | Thr | Lys | ++ | ++ | ++ | ++ | ++ | ++ | ++ | ++ | ++ | − | ++ | ++ | ++ | ++ | ++ |
| 53 | Asn | Arg | ++ | ++ | ++ | ++ | ++ | ++ | ++ | ++ | ++ | − | − | + | ++ | ++ | ++ |
| 80 | Lys | Ile | ++ | ++ | ++ | ++ | ++ | ++ | ++ | ++ | ++ | ++ | ++ | ++ | ++ | ++ | ++ |
| Wild type Combinations | | | ++ | ++ | ++ | ++ | ++ | ++ | ++ | ++ | ++ | ++ | ++ | ++ | ++ | ++ | ++ |
| 12 + 28 | Cys Cys | Ile Trp | ++ | ++ | ++ | ++ | − | ++ | ++ | + | + | ++ | ++ | + | − | ++ | ++ |
| 12 + 28 | Cys Cys | Ala Phe | ++ | ++ | ++ | ++ | − | ++ | ++ | ++ | ++ | ++ | ++ | ++ | − | ++ | ++ |
| 14 + 18 | Gln Cys | Gly Tyr | − | + | − | − | − | − | − | − | + | + | | | | | |
| 14 + 18 | Gln Cys | Arg Tyr | − | − | − | − | − | − | − | − | + | + | | | | | |
| 34 + 39 | Tyr Asp | Ser Asn | ++ | ++ | ++ | + | + | + | + | ++ | ++ | ++ | ++ | ++ | + | ++ | ++ |
| 43 + 48 | Glu Thr | Leu Ilu | ++ | ++ | ++ | + | + | + | − | − | + | − | + | + | ++ | ++ | + |
| 43 + 48 | Glu Thr | Leu Asn | ++ | ++ | ++ | ++ | ++ | + | − | ++ | ++ | + | ++ | ++ | ++ | ++ | ++ |
| 47 + 48 | Pro Thr | Ser Lys | + | + | + | + | + | + | + | | + | − | + | | | | |
| 27 + 31 + 43 | Glu Leu Glu | Tyr Arg Leu | ++ | ++ | ++ | − | − | + | − | − | ++ | ++ | + | ++ | + | + | |
| 27 + 31 + 34 + 43 | Glu Leu Tyr Glu | Tyr Arg Ser Leu | ++ | ++ | ++ | − | − | − | − | − | − | ++ | ++ | + | ++ | + | ++ |
| 15 + 27 + 31 + 43 | Asn Glu Leu Glu | Arg Tyr Arg Leu | ++ | ++ | ++ | − | − | − | − | − | − | ++ | ++ | + | ++ | + | ++ |
| 12 + 15 + 27 + 31 + 43 | Cys Asn Glu Leu Glu | Ile Arg Tyr Arg Leu | − | − | − | − | − | − | − | − | − | ++ | ++ | − | − | − | ++ |

++ = strong binding, + = binding, − = no binding

TABLE A

\#
\# 13-10-98
\# merozoite surface protein-1 (MSP-1) *Plasmodium falciparum* (C-terminal fragment)
\# Reference: $^1$H: DSS = 0.000    dioxane = 3.755   (internal)
\#         $^{15}$N: indirect
\#         $^{13}$C: indirect
\# 25C  pH 6.5   50 mM NaPO4   100 mM NaCl   90% H2O/10% D2O
\# --FORMAT--

TABLE A-continued

```
# BioMagResBank

# The original sequence entered was:

NISQHQCVKKQCPQNSGCFRHLDEREECKCLLNYKQEGDKCVENPNPTCNENNGGCD
ADAKCTEEDSGSNGKKITCECTKPDSYPLFDGIFCSSSN (SEQ ID NO 1)

# Expressed in NMR-STAR, this sequence is:
_Mol_residue_sequence
;
NISQHQCVKKQCPQNSGCFR
HLDEREECKCLLNYKQEGDK
CVENPNPTCNENNGGCDADA
KCTEEDSGSNGKKITCECTK
PDSYPLFDGIFCSSSN (SEQ ID NO 1)
;
loop_
    _Residue_seq_code
    _Residue_author_seq_code
    _Residue_label
 1 @ ASN      2 @ ILE     3 @ SER     4 @ GLN     5 @ HIS
 6 @ GLN      7 @ CYS     8 @ VAL     9 @ LYS    10 @ LYS
11 @ GLN     12 @ CYS    13 @ PRO    14 @ GLN    15 @ ASN
16 @ SER     17 @ GLY    18 @ CYS    19 @ PHE    20 @ ARG
21 @ HIS     22 @ LEU    23 @ ASP    24 @ GLU    25 @ ARG
26 @ GLU     27 @ GLU    28 @ CYS    29 @ LYS    30 @ CYS
31 @ LEU     32 @ LEU    33 @ ASN    34 @ TYR    35 @ LYS
36 @ GLN     37 @ GLU    38 @ GLY    39 @ ASP    40 @ LYS
41 @ CYS     42 @ VAL    43 @ GLU    44 @ ASN    45 @ PRO
46 @ ASN     47 @ PRO    48 @ THR    49 @ CYS    50 @ ASN
51 @ GLU     52 @ ASN    53 @ ASN    54 @ GLY    55 @ GLY
56 @ CYS     57 @ ASP    58 @ ALA    59 @ ASP    60 @ ALA
61 @ LYS     62 @ CYS    63 @ THR    64 @ GLU    65 @ GLU
66 @ ASP     67 @ SER    68 @ GLY    69 @ SER    70 @ ASN
71 @ GLY     72 @ LYS    73 @ LYS    74 @ ILE    75 @ THR
76 @ CYS     77 @ GLU    78 @ CYS    79 @ THR    80 @ LYS
81 @ PRO     82 @ ASP    83 @ SER    84 @ TYR    85 @ PRO
86 @ LEU     87 @ PHE    88 @ ASP    89 @ GLY    90 @ ILE
91 @ PHE     92 @ CYS    93 @ SER    94 @ SER    95 @ SER
96 @ ASN (SEQ
ID NO 1)
stop_
```

Chemical Shift Ambiguity Code Definitions

| Codes | Definition |
|---|---|
| 1 | Unique |
| 2 | Ambiguity of geminal atoms or geminal methyl proton groups |
| 3 | Aromatic atoms on opposite sides of the ring # (e.g. Tyr HE1 and HE2 protons) |
| 4 | Intraresidue ambiguities (e.g. Lys HG and HD protons) |
| 5 | Interresidue ambiguities (Lys 12 vs. Lys 27) |
| 9 | Ambiguous, specific ambiguity not defined |

INSTRUCTIONS
1) Replace the @-signs with appropriate values.
2)Text comments concerning the assignments can be supplied in the full deposition.
3)Feel free to add or delete rows to the table as needed.
The row numbers (_Atom_shift_assign_ID values) will be re-assigned to sequential values by BMRB
The atom table chosen for this sequence is:
loop_
    _Atom_shift_assign_ID
    _Residue_seq_code
    _Residue_label
    _Atom_name
    _Atom_type
    _Chem_shift_value
    _Chem_shift_value_error
    _Chem_shift_ambiguity_code

TABLE A1

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 1 | 1 | ASN | H | H | 8.29 | 0.02 | 1 |
| 2 | 1 | ASN | HA | H | 4.60 | 0.02 | 1 |
| 3 | 1 | ASN | HB2 | H | 2.86 | 0.02 | 2 |
| 4 | 1 | ASN | HB3 | H | 2.75 | 0.02 | 2 |
| 5 | 1 | ASN | HD21 | H | ? | ? | ? |
| 6 | 1 | ASN | HD22 | H | ? | ? | ? |
| 7 | 1 | ASN | C | C | ? | ? | ? |
| 8 | 1 | ASN | CA | C | 55.5 | 0.6 | 1 |
| 9 | 1 | ASN | CB | C | 40.9 | 0.6 | 1 |
| 11 | 1 | ASN | N | N | 125.8 | 0.3 | 1 |
| 12 | 1 | ASN | ND2 | N | ? | ? | ? |
| 13 | 2 | ILE | H | H | 8.29 | 0.02 | 1 |
| 14 | 2 | ILE | HA | H | 4.25 | 0.02 | 1 |
| 15 | 2 | ILE | HB | H | 1.97 | 0.02 | 1 |
| 16 | 2 | ILE | HG12 | H | 1.39 | 0.02 | 2 |
| 17 | 2 | ILE | HG13 | H | 1.19 | 0.02 | 2 |
| 18 | 2 | ILE | HG2 | H | 0.92 | 0.02 | 1 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 19 | 2 | ILE | HD1 | H | 0.81 | 0.02 | 1 |
| 20 | 2 | ILE | C | C | 173.8 | 0.6 | 1 |
| 21 | 2 | ILE | CA | C | 62.2 | 0.6 | 1 |
| 22 | 2 | ILE | CB | C | 38.7 | 0.6 | 1 |
| 23 | 2 | ILE | CG1 | C | 27.5 | 0.6 | 1 |
| 24 | 2 | ILE | CG2 | C | 18.2 | 0.6 | 1 |
| 25 | 2 | ILE | CD1 | C | 13.7 | 0.6 | 1 |
| 26 | 2 | ILE | N | N | 121.1 | 0.3 | 1 |
| 27 | 3 | SER | H | H | 8.47 | 0.02 | 1 |
| 28 | 3 | SER | HA | H | 4.20 | 0.02 | 1 |
| 29 | 3 | SER | HB2 | H | 3.90 | 0.02 | 1 |
| 30 | 3 | SER | HB3 | H | 3.90 | 0.02 | 1 |
| 32 | 3 | SER | C | C | ? | ? | ? |
| 33 | 3 | SER | CA | C | 60.9 | 0.6 | 1 |
| 34 | 3 | SER | CB | C | 63.3 | 0.6 | 1 |
| 35 | 3 | SER | N | N | 119.3 | 0.3 | 1 |
| 36 | 4 | GLN | H | H | 8.32 | 0.02 | 1 |
| 37 | 4 | GLN | HA | H | 4.02 | 0.02 | 1 |
| 38 | 4 | GLN | HB2 | H | 1.88 | 0.02 | 1 |
| 39 | 4 | GLN | HB3 | H | 1.88 | 0.02 | 1 |
| 40 | 4 | GLN | HG2 | H | 1.75 | 0.02 | 1 |
| 41 | 4 | GLN | HG3 | H | 1.75 | 0.02 | 1 |
| 42 | 4 | GLN | HE21 | H | ? | ? | ? |
| 43 | 4 | GLN | HE22 | H | ? | ? | ? |
| 44 | 4 | GLN | C | C | ? | ? | ? |
| 45 | 4 | GLN | CA | C | 57.7 | 0.6 | 1 |
| 46 | 4 | GLN | CB | C | 27.9 | 0.6 | 1 |
| 47 | 4 | GLN | CG | C | 32.7 | 0.6 | 1 |
| 49 | 4 | GLN | N | N | 121.6 | 0.3 | 1 |
| 50 | 4 | GLN | NE2 | N | ? | ? | ? |
| 51 | 5 | HIS | H | H | 7.76 | 0.02 | 9 |
| 52 | 5 | HIS | HA | H | 5.09 | 0.02 | 1 |
| 53 | 5 | HIS | HB2 | H | 2.70 | 0.02 | 1 |
| 54 | 5 | HIS | HB3 | H | 2.70 | 0.02 | 1 |
| 56 | 5 | HIS | HD2 | H | 6.87 | 0.02 | 1 |
| 57 | 5 | HIS | HE1 | H | 7.92 | 0.02 | 1 |
| 59 | 5 | HIS | C | C | 175.7 | 0.6 | 1 |
| 60 | 5 | HIS | CA | C | 54.8 | 0.6 | 1 |
| 61 | 5 | HIS | CB | C | 29.2 | 0.6 | 1 |
| 65 | 5 | HIS | N | N | 113.6 | 0.3 | 9 |
| 68 | 6 | GLN | H | H | 7.42 | 0.02 | 9 |
| 69 | 6 | GLN | HA | H | 4.43 | 0.02 | 1 |
| 70 | 6 | GLN | HB2 | H | 2.05 | 0.02 | 1 |
| 71 | 6 | GLN | HB3 | H | 2.05 | 0.02 | 1 |
| 72 | 6 | GLN | HG2 | H | 2.42 | 0.02 | 1 |
| 73 | 6 | GLN | HG3 | H | 2.42 | 0.02 | 1 |
| 74 | 6 | GLN | HE21 | H | 7.59 | 0.02 | 5 |
| 75 | 6 | GLN | HE22 | H | 6.92 | 0.02 | 5 |
| 76 | 6 | GLN | C | C | 175.7 | 0.6 | 1 |
| 77 | 6 | GLN | CA | C | 55.1 | 0.6 | 1 |
| 78 | 6 | GLN | CB | C | 28.8 | 0.6 | 1 |
| 79 | 6 | GLN | CG | C | 33.8 | 0.6 | 1 |
| 81 | 6 | GLN | N | N | 122.5 | 0.3 | 9 |
| 82 | 6 | GLN | NE2 | N | 112.6 | 0.3 | 5 |
| 83 | 7 | CYS | H | H | 9.18 | 0.02 | 1 |
| 84 | 7 | CYS | HA | H | 4.09 | 0.02 | 1 |
| 85 | 7 | CYS | HB2 | H | 3.31 | 0.02 | 2 |
| 86 | 7 | CYS | HB3 | H | 3.11 | 0.02 | 2 |
| 88 | 7 | CYS | C | C | 174.4 | 0.6 | 1 |
| 89 | 7 | CYS | CA | C | 56.6 | 0.6 | 1 |
| 90 | 7 | CYS | CB | C | 42.3 | 0.6 | 1 |
| 91 | 7 | CYS | N | N | 124.5 | 0.3 | 1 |
| 92 | 8 | VAL | H | H | 10.42 | 0.02 | 1 |
| 93 | 8 | VAL | HA | H | 4.33 | 0.02 | 1 |
| 94 | 8 | VAL | HB | H | 2.15 | 0.02 | 1 |
| 95 | 8 | VAL | HG1 | H | 0.84 | 0.02 | 2 |
| 96 | 8 | VAL | HG2 | H | 0.82 | 0.02 | 2 |
| 97 | 8 | VAL | C | C | 176.6 | 0.6 | 1 |
| 98 | 8 | VAL | CA | C | 62.5 | 0.6 | 1 |
| 99 | 8 | VAL | CB | C | 34.4 | 0.6 | 1 |
| 100 | 8 | VAL | CG1 | C | 21.5 | 0.6 | 2 |
| 101 | 8 | VAL | CG2 | C | 19.7 | 0.6 | 2 |
| 102 | 8 | VAL | N | N | 119.1 | 0.3 | 1 |
| 103 | 9 | LYS | H | H | 9.42 | 0.02 | 1 |
| 104 | 9 | LYS | HA | H | 4.51 | 0.02 | 1 |
| 105 | 9 | LYS | HB2 | H | 1.81 | 0.02 | 4 |
| 106 | 9 | LYS | HB3 | H | 1.81 | 0.02 | 4 |
| 107 | 9 | LYS | HG2 | H | 1.41 | 0.02 | 4 |
| 108 | 9 | LYS | HG3 | H | 1.41 | 0.02 | 4 |
| 109 | 9 | LYS | HD2 | H | ? | ? | ? |
| 110 | 9 | LYS | HD3 | H | ? | ? | ? |
| 111 | 9 | LYS | HE2 | H | 3.33 | 0.02 | 1 |
| 112 | 9 | LYS | HE3 | H | 3.33 | 0.02 | 1 |
| 114 | 9 | LYS | C | C | ? | ? | ? |
| 115 | 9 | LYS | CA | C | 57.7 | 0.6 | 1 |
| 116 | 9 | LYS | CB | C | ? | ? | ? |
| 117 | 9 | LYS | CG | C | ? | ? | ? |
| 118 | 9 | LYS | CD | C | ? | ? | ? |
| 119 | 9 | LYS | CE | C | ? | ? | ? |
| 120 | 9 | LYS | N | N | 124.1 | 0.03 | 1 |
| 122 | 10 | LYS | H | H | 8.94 | 0.02 | 1 |
| 123 | 10 | LYS | HA | H | 4.06 | 0.02 | 1 |
| 124 | 10 | LYS | HB2 | H | 1.86 | 0.02 | 1 |
| 125 | 10 | LYS | HB3 | H | 1.86 | 0.02 | 1 |
| 126 | 10 | LYS | HG2 | H | 1.29 | 0.02 | 1 |
| 127 | 10 | LYS | HG3 | H | 1.29 | 0.02 | 1 |
| 128 | 10 | LYS | HD2 | H | 1.70 | 0.02 | 2 |
| 129 | 10 | LYS | HD3 | H | 1.59 | 0.02 | 2 |
| 130 | 10 | LYS | HE2 | H | 3.04 | 0.02 | 1 |
| 131 | 10 | LYS | HE3 | H | 3.04 | 0.02 | 1 |
| 133 | 10 | LYS | C | C | ? | ? | ? |
| 134 | 10 | LYS | CA | C | 57.1 | 0.6 | 1 |
| 135 | 10 | LYS | CB | C | 34.3 | 0.6 | 1 |
| 136 | 10 | LYS | CG | C | 25.6 | 0.6 | 1 |
| 137 | 10 | LYS | CD | C | 29.6 | 0.6 | 1 |
| 138 | 10 | LYS | CE | C | 42.4 | 0.6 | 1 |
| 139 | 10 | LYS | N | N | 122.4 | 0.3 | 1 |
| 141 | 11 | GLN | H | H | ? | ? | ? |
| 142 | 11 | GLN | HA | H | 4.47 | 0.02 | 1 |
| 143 | 11 | GLN | HB2 | H | 2.03 | 0.02 | 2 |
| 144 | 11 | GLN | HB3 | H | 1.89 | 0.02 | 2 |
| 145 | 11 | GLN | HG2 | H | 2.28 | 0.02 | 1 |
| 146 | 11 | GLN | HG3 | H | 2.28 | 0.02 | 1 |
| 147 | 11 | GLN | HE21 | H | 7.45 | 0.02 | 2 |
| 148 | 11 | GLN | HE22 | H | 6.84 | 0.02 | 2 |
| 149 | 11 | GLN | C | C | ? | ? | ? |
| 150 | 11 | GLN | CA | C | 54.4 | 0.6 | 1 |
| 151 | 11 | GLN | CB | C | 28.7 | 0.6 | 1 |
| 152 | 11 | GLN | CG | C | 33.8 | 0.6 | 1 |
| 154 | 11 | GLN | N | N | ? | ? | ? |
| 155 | 11 | GLN | NE2 | N | 112.9 | 0.3 | 1 |
| 156 | 12 | CYS | H | H | ? | ? | ? |
| 157 | 12 | CYS | HA | H | 5.09 | 0.02 | 1 |
| 158 | 12 | CYS | HB2 | H | 3.49 | 0.02 | 2 |
| 159 | 12 | CYS | HB3 | H | 2.34 | 0.02 | 2 |
| 161 | 12 | CYS | C | C | ? | ? | ? |
| 162 | 12 | CYS | CA | C | 52.4 | 0.6 | 1 |
| 163 | 12 | CYS | CB | C | 37.2 | 0.6 | 1 |
| 164 | 12 | CYS | N | N | ? | ? | ? |
| 165 | 13 | PRO | HA | H | 4.55 | 0.02 | 1 |
| 166 | 13 | PRO | HB2 | H | 2.45 | 0.02 | 1 |
| 167 | 13 | PRO | HB3 | H | 1.94 | 0.02 | 1 |
| 168 | 13 | PRO | HG2 | H | 1.73 | 0.02 | 2 |
| 169 | 13 | PRO | HG3 | H | 2.04 | 0.02 | 2 |
| 170 | 13 | PRO | HD2 | H | 3.43 | 0.02 | 2 |
| 171 | 13 | PRO | HD3 | H | 3.80 | 0.02 | 2 |
| 172 | 13 | PRO | C | C | 176.4 | 0.6 | 1 |
| 173 | 13 | PRO | CA | C | 62.6 | 0.6 | 1 |
| 174 | 13 | PRO | CB | C | 33.0 | 0.6 | 1 |
| 175 | 13 | PRO | CG | C | 27.5 | 0.6 | 1 |
| 176 | 13 | PRO | CD | C | 50.6 | 0.6 | 1 |
| 178 | 14 | GLN | H | H | 8.48 | 0.02 | 1 |
| 179 | 14 | GLN | HA | H | 4.01 | 0.02 | 1 |
| 180 | 14 | GLN | HB2 | H | 1.94 | 0.02 | 1 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 181 | 14 | GLN | HB3 | H | 1.94 | 0.02 | 1 |
| 182 | 14 | GLN | HG2 | H | 2.42 | 0.02 | 1 |
| 183 | 14 | GLN | HG3 | H | 2.42 | 0.02 | 1 |
| 184 | 14 | GLN | HE21 | H | 7.59 | 0.02 | 5 |
| 185 | 14 | GLN | HE22 | H | 6.92 | 0.02 | 5 |
| 186 | 14 | GLN | C | C | 176.6 | 0.6 | 1 |
| 187 | 14 | GLN | CA | C | 57.4 | 0.6 | 1 |
| 188 | 14 | GLN | CB | C | 28.6 | 0.6 | 1 |
| 189 | 14 | GLN | CG | C | 33.8 | 0.6 | 1 |
| 191 | 14 | GLN | N | N | 120.5 | 0.3 | 1 |
| 192 | 14 | GLN | NE2 | N | 112.6 | 0.3 | 5 |
| 193 | 15 | ASN | H | H | 8.93 | 0.02 | 1 |
| 194 | 15 | ASN | HA | H | 3.77 | 0.02 | 1 |
| 195 | 15 | ASN | HB2 | H | 2.58 | 0.02 | 1 |
| 196 | 15 | ASN | HB3 | H | 1.09 | 0.02 | 1 |
| 197 | 15 | ASN | HD21 | H | 6.97 | 0.02 | 1 |
| 198 | 15 | ASN | HD22 | H | 7.12 | 0.02 | 1 |
| 199 | 15 | ASN | C | C | 171.9 | 0.6 | 1 |
| 200 | 15 | ASN | CA | C | 54.6 | 0.6 | 1 |
| 201 | 15 | ASN | CB | C | 36.3 | 0.6 | 1 |
| 203 | 15 | ASN | N | N | 115.8 | 0.3 | 1 |
| 204 | 15 | ASN | ND2 | N | 115.4 | 0.3 | 1 |
| 205 | 16 | SER | H | H | 7.34 | 0.02 | 1 |
| 206 | 16 | SER | HA | H | 4.93 | 0.02 | 1 |
| 207 | 16 | SER | HB2 | H | 3.62 | 0.02 | 2 |
| 208 | 16 | SER | HB3 | H | 3.52 | 0.02 | 2 |
| 210 | 16 | SER | C | C | 173.5 | 0.6 | 1 |
| 211 | 16 | SER | CA | C | 57.5 | 0.6 | 1 |
| 212 | 16 | SER | CB | C | 67.9 | 0.6 | 1 |
| 213 | 16 | SER | N | N | 109.9 | 0.3 | 1 |
| 214 | 17 | GLY | H | H | 8.92 | 0.02 | 1 |
| 215 | 17 | GLY | HA2 | H | 3.83 | 0.02 | 1 |
| 216 | 17 | GLY | HA3 | H | 2.06 | 0.02 | 1 |
| 217 | 17 | GLY | C | C | ? | ? | ? |
| 218 | 17 | GLY | CA | C | 42.6 | 0.6 | 1 |
| 219 | 17 | GLY | N | N | 108.5 | 0.3 | 1 |
| 220 | 18 | CYS | H | H | 7.01 | 0.02 | 1 |
| 221 | 18 | CYS | HA | H | 5.63 | 0.02 | 1 |
| 222 | 18 | CYS | HB2 | H | 3.01 | 0.02 | 1 |
| 223 | 18 | CYS | HB3 | H | 3.01 | 0.02 | 1 |
| 225 | 18 | CYS | C | C | 172.5 | 0.6 | 1 |
| 226 | 18 | CYS | CA | C | 55.8 | 0.6 | 1 |
| 227 | 18 | CYS | CB | C | 43.2 | 0.6 | 1 |
| 228 | 18 | CYS | N | N | 120.5 | 0.3 | 1 |
| 229 | 19 | PHE | H | H | 9.12 | 0.02 | 1 |
| 230 | 19 | PHE | HA | H | 4.43 | 0.02 | 1 |
| 231 | 19 | PHE | HB2 | H | 1.70 | 0.02 | 2 |
| 232 | 19 | PHE | HB3 | H | 0.62 | 0.02 | 2 |
| 233 | 19 | PHE | HD1 | H | 6.12 | 0.02 | 1 |
| 234 | 19 | PHE | HD2 | H | 6.12 | 0.02 | 1 |
| 235 | 19 | PHE | HE1 | H | 6.30 | 0.02 | 1 |
| 236 | 19 | PHE | HE2 | H | 6.30 | 0.02 | 1 |
| 237 | 19 | PHE | HZ | H | 6.37 | 0.02 | 1 |
| 238 | 19 | PHE | C | C | 172.3 | 0.6 | 1 |
| 239 | 19 | PHE | CA | C | 57.0 | 0.6 | 1 |
| 240 | 19 | PHE | CB | C | 41.7 | 0.6 | 1 |
| 247 | 19 | PHE | N | N | 132.0 | 0.6 | 1 |
| 248 | 20 | ARG | H | H | 7.76 | 0.02 | 1 |
| 249 | 20 | ARG | HA | H | 4.83 | 0.02 | 1 |
| 250 | 20 | ARG | HB2 | H | 1.26 | 0.02 | 2 |
| 251 | 20 | ARG | HB3 | H | 0.99 | 0.02 | 2 |
| 252 | 20 | ARG | HG2 | H | 1.59 | 0.02 | 2 |
| 253 | 20 | ARG | HG3 | H | 1.42 | 0.02 | 2 |
| 254 | 20 | ARG | HD2 | H | 3.35 | 0.02 | 2 |
| 255 | 20 | ARG | HD3 | H | 3.10 | 0.02 | 2 |
| 256 | 20 | ARG | HE | H | 7.18 | 0.02 | 1 |
| 257 | 20 | ARG | HH11 | H | 6.23 | 0.02 | 5 |
| 258 | 20 | ARG | HH12 | H | 6.23 | 0.02 | 5 |
| 259 | 20 | ARG | HH21 | H | 6.23 | 0.02 | 5 |
| 260 | 20 | ARG | HH22 | H | 6.23 | 0.02 | 5 |
| 261 | 20 | ARG | C | C | 174.7 | 0.6 | 1 |
| 262 | 20 | ARG | CA | C | 54.3 | 0.6 | 1 |
| 263 | 20 | ARG | CB | C | 32.3 | 0.6 | 1 |
| 264 | 20 | ARG | CG | C | 28.0 | 0.6 | 1 |
| 265 | 20 | ARG | CD | C | 44.1 | 0.6 | 1 |
| 267 | 20 | ARG | N | N | 129.4 | 0.3 | 1 |
| 268 | 20 | ARG | NE | N | 85.0 | 0.3 | 1 |
| 269 | 20 | ARG | NH1 | N | 70.1 | 0.3 | 5 |
| 270 | 20 | ARG | NH2 | N | 70.1 | 0.3 | 5 |
| 271 | 21 | HIS | H | H | 9.30 | 0.02 | 1 |
| 272 | 21 | HIS | HA | H | 4.50 | 0.02 | 1 |
| 273 | 21 | HIS | HB2 | H | 3.52 | 0.02 | 2 |
| 274 | 21 | HIS | HB3 | H | 3.44 | 0.02 | 2 |
| 276 | 21 | HIS | HD2 | H | 7.02 | 0.02 | 1 |
| 277 | 21 | HIS | HE1 | H | 8.44 | 0.02 | 1 |
| 279 | 21 | HIS | C | C | 177.6 | 0.6 | 1 |
| 280 | 21 | HIS | CA | C | 56.4 | 0.6 | 1 |
| 281 | 21 | HIS | CB | C | 32.2 | 0.6 | 1 |
| 285 | 21 | HIS | N | N | 125.9 | 0.3 | 1 |
| 288 | 22 | LEU | H | H | 9.30 | 0.02 | 1 |
| 289 | 22 | LEU | HA | H | 4.11 | 0.02 | 1 |
| 290 | 22 | LEU | HB2 | H | 1.87 | 0.02 | 1 |
| 291 | 22 | LEU | HB3 | H | 1.65 | 0.02 | 1 |
| 292 | 22 | LEU | HG | H | 1.87 | 0.02 | 1 |
| 293 | 22 | LEU | HD1 | H | 0.77 | 0.02 | 2 |
| 294 | 22 | LEU | HD2 | H | 0.98 | 0.02 | 2 |
| 295 | 22 | LEU | C | C | 177.7 | 0.6 | 1 |
| 296 | 22 | LEU | CA | C | 57.7 | 0.6 | 1 |
| 297 | 22 | LEU | CB | C | 40.8 | 0.6 | 1 |
| 298 | 22 | LEU | CG | C | 27.6 | 0.6 | 1 |
| 299 | 22 | LEU | CD1 | C | 22.6 | 0.6 | 2 |
| 300 | 22 | LEU | CD2 | C | 25.3 | 0.6 | 2 |
| 301 | 22 | LEU | N | N | 122.0 | 0.3 | 1 |
| 302 | 23 | ASP | H | H | 7.86 | 0.02 | 1 |
| 303 | 23 | ASP | HA | H | 4.52 | 0.02 | 1 |
| 304 | 23 | ASP | HB2 | H | 3.10 | 0.02 | 1 |
| 305 | 23 | ASP | HB3 | H | 2.53 | 0.02 | 1 |
| 306 | 23 | ASP | C | C | 176.8 | 0.6 | 1 |
| 307 | 23 | ASP | CA | C | 53.6 | 0.6 | 1 |
| 308 | 23 | ASP | CB | C | 39.7 | 0.6 | 1 |
| 310 | 23 | ASP | N | N | 116.9 | 0.3 | 1 |
| 311 | 24 | GLU | H | H | 8.01 | 0.02 | 1 |
| 312 | 24 | GLU | HA | H | 3.63 | 0.02 | 1 |
| 313 | 24 | GLU | HB2 | H | 2.57 | 0.02 | 2 |
| 314 | 24 | GLU | HB3 | H | 2.17 | 0.02 | 2 |
| 315 | 24 | GLU | HG2 | H | 2.14 | 0.02 | 1 |
| 316 | 24 | GLU | HG3 | H | 2.14 | 0.02 | 1 |
| 317 | 24 | GLU | C | C | 176.1 | 0.6 | 1 |
| 318 | 24 | GLU | CA | C | 59.4 | 0.6 | 1 |
| 319 | 24 | GLU | CB | C | 27.5 | 0.6 | 1 |
| 320 | 24 | GLU | CG | C | 37.0 | 0.6 | 1 |
| 322 | 24 | GLU | N | N | 110.3 | 0.3 | 1 |
| 323 | 25 | ARG | H | H | 8.04 | 0.02 | 1 |
| 324 | 25 | ARG | HA | H | 4.24 | 0.02 | 1 |
| 325 | 25 | ARG | HB2 | H | 1.84 | 0.02 | 2 |
| 326 | 25 | ARG | HB3 | H | 1.75 | 0.02 | 2 |
| 327 | 25 | ARG | HG2 | H | 1.56 | 0.02 | 1 |
| 328 | 25 | ARG | HG3 | H | 1.56 | 0.02 | 1 |
| 329 | 25 | ARG | HD2 | H | 3.16 | 0.02 | 1 |
| 330 | 25 | ARG | HD3 | H | 3.16 | 0.02 | 1 |
| 331 | 25 | ARG | HE | H | 8.01 | 0.02 | 1 |
| 332 | 25 | ARG | HH11 | H | 6.71 | 0.02 | 5 |
| 333 | 25 | ARG | HH12 | H | 6.71 | 0.02 | 5 |
| 334 | 25 | ARG | HH21 | H | 6.71 | 0.02 | 5 |
| 335 | 25 | ARG | HH22 | H | 6.71 | 0.02 | 5 |
| 336 | 25 | ARG | C | C | 175.6 | 0.6 | 1 |
| 337 | 25 | ARG | CA | C | 57.8 | 0.6 | 1 |
| 338 | 25 | ARG | CB | C | 31.0 | 0.6 | 1 |
| 339 | 25 | ARG | CG | C | 28.3 | 0.6 | 1 |
| 340 | 25 | ARG | CD | C | 43.5 | 0.6 | 1 |
| 342 | 25 | ARG | N | N | 121.9 | 0.3 | 1 |
| 343 | 25 | ARG | NE | N | 85.8 | 0.3 | 1 |
| 344 | 25 | ARG | NH1 | N | 70.3 | 0.3 | 5 |
| 345 | 25 | ARG | NH2 | N | 70.3 | 0.3 | 5 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 346 | 26 | GLU | H | H | 8.69 | 0.02 | 1 |
| 347 | 26 | GLU | HA | H | 5.40 | 0.02 | 1 |
| 348 | 26 | GLU | HB2 | H | 1.90 | 0.02 | 1 |
| 349 | 26 | GLU | HB3 | H | 1.90 | 0.02 | 1 |
| 350 | 26 | GLU | HG2 | H | 2.63 | 0.02 | 2 |
| 351 | 26 | GLU | HG3 | H | 2.09 | 0.02 | 2 |
| 352 | 26 | GLU | C | C | 173.6 | 0.6 | 1 |
| 353 | 26 | GLU | CA | C | 55.6 | 0.6 | 1 |
| 354 | 26 | GLU | CB | C | 37.9 | 0.6 | 1 |
| 355 | 26 | GLU | CG | C | 31.5 | 0.6 | 1 |
| 357 | 26 | GLU | N | N | 124.3 | 0.3 | 1 |
| 358 | 27 | GLU | H | H | 9.07 | 0.02 | 1 |
| 359 | 27 | GLU | HA | H | 4.84 | 0.02 | 1 |
| 360 | 27 | GLU | HB2 | H | 2.15 | 0.02 | 2 |
| 361 | 27 | GLU | HB3 | H | 2.27 | 0.02 | 2 |
| 362 | 27 | GLU | HG2 | H | 2.48 | 0.02 | 2 |
| 363 | 27 | GLU | HG3 | H | 2.32 | 0.02 | 2 |
| 364 | 27 | GLU | C | C | 174.5 | 0.6 | 1 |
| 365 | 27 | GLU | CA | C | 54.6 | 0.6 | 1 |
| 366 | 27 | GLU | CB | C | 34.8 | 0.6 | 1 |
| 367 | 27 | GLU | CG | C | 36.5 | 0.6 | 1 |
| 369 | 27 | GLU | N | N | 123.9 | 0.3 | 1 |
| 370 | 28 | CYS | H | H | 8.88 | 0.02 | 1 |
| 371 | 28 | CYS | HA | H | 5.65 | 0.02 | 1 |
| 372 | 28 | CYS | HB2 | H | 3.00 | 0.02 | 2 |
| 373 | 28 | CYS | HB3 | H | 2.81 | 0.02 | 2 |
| 375 | 28 | CYS | C | C | 175.5 | 0.6 | 1 |
| 376 | 28 | CYS | CA | C | 53.0 | 0.6 | 1 |
| 377 | 28 | CYS | CB | C | 40.9 | 0.6 | 1 |
| 378 | 28 | CYS | N | N | 122.0 | 0.3 | 1 |
| 379 | 29 | LYS | H | H | 8.76 | 0.02 | 1 |
| 380 | 29 | LYS | HA | H | 4.56 | 0.02 | 1 |
| 381 | 29 | LYS | HB2 | H | 1.40 | 0.02 | 1 |
| 382 | 29 | LYS | HB3 | H | 1.40 | 0.02 | 1 |
| 383 | 29 | LYS | HG2 | H | 1.38 | 0.02 | 1 |
| 384 | 29 | LYS | HG3 | H | 1.38 | 0.02 | 1 |
| 385 | 29 | LYS | HD2 | H | 1.13 | 0.02 | 2 |
| 386 | 29 | LYS | HD3 | H | 0.92 | 0.02 | 2 |
| 387 | 29 | LYS | HE2 | H | 2.86 | 0.02 | 1 |
| 388 | 29 | LYS | HE3 | H | 2.86 | 0.02 | 1 |
| 389 | 29 | LYS | HZ | H | 7.23 | 0.02 | 5 |
| 390 | 29 | LYS | C | C | 174.6 | 0.6 | 1 |
| 391 | 29 | LYS | CA | C | 56.4 | 0.6 | 1 |
| 392 | 29 | LYS | CB | C | 38.4 | 0.6 | 1 |
| 393 | 29 | LYS | CG | C | 25.8 | 0.6 | 1 |
| 394 | 29 | LYS | CD | C | 29.6 | 0.6 | 1 |
| 395 | 29 | LYS | CE | C | 42.4 | 0.6 | 1 |
| 396 | 29 | LYS | N | N | 124.0 | 0.3 | 1 |
| 397 | 29 | LYS | NZ | N | 33.0 | 0.3 | 5 |
| 398 | 30 | CYS | H | H | 8.78 | 0.02 | 1 |
| 399 | 30 | CYS | HA | H | 4.65 | 0.02 | 1 |
| 400 | 30 | CYS | HB2 | H | 2.49 | 0.02 | 1 |
| 401 | 30 | CYS | HB3 | H | 3.01 | 0.02 | 1 |
| 403 | 30 | CYS | C | C | 173.3 | 0.6 | 1 |
| 404 | 30 | CYS | CA | C | 54.6 | 0.6 | 1 |
| 405 | 30 | CYS | CB | C | 35.9 | 0.6 | 1 |
| 406 | 30 | CYS | N | N | 121.7 | 0.3 | 1 |
| 407 | 31 | LEU | H | H | 7.81 | 0.02 | 1 |
| 408 | 31 | LEU | HA | H | 4.23 | 0.02 | 1 |
| 409 | 31 | LEU | HB2 | H | 1.39 | 0.02 | 1 |
| 410 | 31 | LEU | HB3 | H | 1.73 | 0.02 | 1 |
| 411 | 31 | LEU | HG | H | 0.94 | 0.02 | 1 |
| 412 | 31 | LEU | HD1 | H | 0.68 | 0.02 | 1 |
| 413 | 31 | LEU | HD2 | H | 0.77 | 0.02 | 1 |
| 414 | 31 | LEU | C | C | 176.2 | 0.6 | 1 |
| 415 | 31 | LEU | CA | C | 54.8 | 0.6 | 1 |
| 416 | 31 | LEU | CB | C | 42.5 | 0.6 | 1 |
| 417 | 31 | LEU | CG | C | 27.1 | 0.6 | 1 |
| 418 | 31 | LEU | CD1 | C | 26.0 | 0.6 | 1 |
| 419 | 31 | LEU | CD2 | C | 21.9 | 0.6 | 1 |
| 420 | 31 | LEU | N | N | 119.2 | 0.3 | 1 |
| 421 | 32 | LEU | H | H | 8.91 | 0.02 | 1 |
| 422 | 32 | LEU | HA | H | 4.26 | 0.02 | 1 |
| 423 | 32 | LEU | HB2 | H | 1.75 | 0.02 | 1 |
| 424 | 32 | LEU | HB3 | H | 1.32 | 0.02 | 1 |
| 425 | 32 | LEU | HG | H | 1.77 | 0.02 | 1 |
| 426 | 32 | LEU | HD1 | H | 0.96 | 0.02 | 1 |
| 427 | 32 | LEU | HD2 | H | 0.77 | 0.02 | 1 |
| 428 | 32 | LEU | C | C | 179.0 | 0.6 | 1 |
| 429 | 32 | LEU | CA | C | 56.4 | 0.6 | 1 |
| 430 | 32 | LEU | CB | C | 42.1 | 0.6 | 1 |
| 431 | 32 | LEU | CG | C | 26.9 | 0.6 | 1 |
| 432 | 32 | LEU | CD1 | C | 26.0 | 0.6 | 1 |
| 433 | 32 | LEU | CD2 | C | 23.4 | 0.6 | 1 |
| 434 | 32 | LEU | N | N | 118.4 | 0.3 | 1 |
| 435 | 33 | ASN | H | H | 8.84 | 0.02 | 1 |
| 436 | 33 | ASN | HA | H | 3.90 | 0.02 | 1 |
| 437 | 33 | ASN | HB2 | H | 3.26 | 0.02 | 1 |
| 438 | 33 | ASN | HB3 | H | 2.88 | 0.02 | 1 |
| 439 | 33 | ASN | HD21 | H | 6.86 | 0.02 | 1 |
| 440 | 33 | ASN | HD22 | H | 7.25 | 0.02 | 1 |
| 441 | 33 | ASN | C | C | 173.8 | 0.6 | 1 |
| 442 | 33 | ASN | CA | C | 56.9 | 0.6 | 1 |
| 443 | 33 | ASN | CB | C | 37.3 | 0.6 | 1 |
| 445 | 33 | ASN | N | N | 110.8 | 0.3 | 1 |
| 446 | 33 | ASN | ND2 | N | 112.0 | 0.3 | 1 |
| 447 | 34 | TYR | H | H | 8.61 | 0.02 | 1 |
| 448 | 34 | TYR | HA | H | 5.02 | 0.02 | 1 |
| 449 | 34 | TYR | HB2 | H | 3.35 | 0.02 | 1 |
| 450 | 34 | TYR | HB3 | H | 2.52 | 0.02 | 1 |
| 451 | 34 | TYR | HD1 | H | 6.74 | 0.02 | 1 |
| 452 | 34 | TYR | HD2 | H | 6.74 | 0.02 | 1 |
| 453 | 34 | TYR | HE1 | H | 6.69 | 0.02 | 1 |
| 454 | 34 | TYR | HE2 | H | 6.69 | 0.02 | 1 |
| 456 | 34 | TYR | C | C | 174.7 | 0.6 | 1 |
| 457 | 34 | TYR | CA | C | 57.6 | 0.6 | 1 |
| 458 | 34 | TYR | CB | C | 41.0 | 0.6 | 1 |
| 465 | 34 | TYR | N | N | 118.6 | 0.3 | 1 |
| 466 | 35 | LYS | H | H | 9.99 | 0.02 | 1 |
| 467 | 35 | LYS | HA | H | 4.84 | 0.02 | 1 |
| 468 | 35 | LYS | HB2 | H | 1.82 | 0.02 | 1 |
| 469 | 35 | LYS | HB3 | H | 1.59 | 0.02 | 1 |
| 470 | 35 | LYS | HG2 | H | 1.18 | 0.02 | 1 |
| 471 | 35 | LYS | HG3 | H | 1.18 | 0.02 | 1 |
| 472 | 35 | LYS | HD2 | H | 1.48 | 0.02 | 1 |
| 473 | 35 | LYS | HD3 | H | 1.48 | 0.02 | 1 |
| 474 | 35 | LYS | HE2 | H | 2.89 | 0.02 | 1 |
| 475 | 35 | LYS | HE3 | H | 2.89 | 0.02 | 1 |
| 477 | 35 | LYS | C | C | 174.1 | 0.6 | 1 |
| 478 | 35 | LYS | CA | C | 54.2 | 0.6 | 1 |
| 479 | 35 | LYS | CB | C | 36.3 | 0.6 | 1 |
| 480 | 35 | LYS | CG | C | 24.1 | 0.6 | 1 |
| 481 | 35 | LYS | CD | C | 29.6 | 0.6 | 1 |
| 482 | 35 | LYS | CE | C | 41.6 | 0.6 | 1 |
| 483 | 35 | LYS | N | N | 119.7 | 0.3 | 1 |
| 485 | 36 | GLN | H | H | 8.77 | 0.02 | 1 |
| 486 | 36 | GLN | HA | H | 4.67 | 0.02 | 1 |
| 487 | 36 | GLN | HB2 | H | 2.06 | 0.02 | 1 |
| 488 | 36 | GLN | HB3 | H | 2.06 | 0.02 | 1 |
| 489 | 36 | GLN | HG2 | H | 2.35 | 0.02 | 1 |
| 490 | 36 | GLN | HG3 | H | 2.35 | 0.02 | 1 |
| 491 | 36 | GLN | HE21 | H | 7.50 | 0.02 | 2 |
| 492 | 36 | GLN | HE22 | H | 6.55 | 0.02 | 2 |
| 493 | 36 | GLN | C | C | 176.3 | 0.6 | 1 |
| 494 | 36 | GLN | CA | C | 56.7 | 0.6 | 1 |
| 495 | 36 | GLN | CB | C | 28.6 | 0.6 | 1 |
| 496 | 36 | GLN | CG | C | 33.7 | 0.6 | 1 |
| 498 | 36 | GLN | N | N | 124.9 | 0.3 | 1 |
| 499 | 36 | GLN | NE2 | N | 110.9 | 0.3 | 1 |
| 500 | 37 | GLU | H | H | 8.96 | 0.02 | 1 |
| 501 | 37 | GLU | HA | H | 4.51 | 0.02 | 1 |
| 502 | 37 | GLU | HB2 | H | 1.96 | 0.02 | 2 |
| 503 | 37 | GLU | HB3 | H | 1.80 | 0.02 | 2 |
| 504 | 37 | GLU | HG2 | H | 2.11 | 0.02 | 1 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 505 | 37 | GLU | HG3 | H | 2.11 | 0.02 | 1 |
| 506 | 37 | GLU | C | C | 176.2 | 0.6 | 1 |
| 507 | 37 | GLU | CA | C | 56.0 | 0.6 | 1 |
| 508 | 37 | GLU | CB | C | 31.9 | 0.6 | 1 |
| 509 | 37 | GLU | CG | C | 36.6 | 0.6 | 1 |
| 511 | 37 | GLU | N | N | 130.2 | 0.3 | 1 |
| 512 | 38 | GLY | H | H | 9.20 | 0.02 | 1 |
| 513 | 38 | GLY | HA2 | H | 3.69 | 0.02 | 1 |
| 514 | 38 | GLY | HA3 | H | 4.05 | 0.02 | 1 |
| 515 | 38 | GLY | C | C | 174.7 | 0.6 | 1 |
| 516 | 38 | GLY | CA | C | 47.4 | 0.6 | 1 |
| 517 | 38 | GLY | N | N | 118.4 | 0.3 | 1 |
| 518 | 39 | ASP | H | H | 8.81 | 0.02 | 1 |
| 519 | 39 | ASP | HA | H | 4.69 | 0.02 | 1 |
| 520 | 39 | ASP | HB2 | H | 2.78 | 0.02 | 1 |
| 521 | 39 | ASP | HB3 | H | 2.78 | 0.02 | 1 |
| 522 | 39 | ASP | C | C | 175.2 | 0.6 | 1 |
| 523 | 39 | ASP | CA | C | 54.2 | 0.6 | 1 |
| 524 | 39 | ASP | CB | C | 41.0 | 0.6 | 1 |
| 526 | 39 | ASP | N | N | 127.1 | 0.3 | 1 |
| 527 | 40 | LYS | H | H | 7.86 | 0.02 | 1 |
| 528 | 40 | LYS | HA | H | 4.71 | 0.02 | 1 |
| 529 | 40 | LYS | HB2 | H | 1.86 | 0.02 | 1 |
| 530 | 40 | LYS | HB3 | H | 1.86 | 0.02 | 1 |
| 531 | 40 | LYS | HG2 | H | 1.52 | 0.02 | 1 |
| 532 | 40 | LYS | HG3 | H | 1.52 | 0.02 | 1 |
| 533 | 40 | LYS | HD2 | H | 1.69 | 0.02 | 1 |
| 534 | 40 | LYS | HD3 | H | 1.69 | 0.02 | 1 |
| 535 | 40 | LYS | HE2 | H | 3.02 | 0.02 | 1 |
| 536 | 40 | LYS | HE3 | H | 3.02 | 0.02 | 1 |
| 538 | 40 | LYS | C | C | 175.4 | 0.6 | 1 |
| 539 | 40 | LYS | CA | C | 54.8 | 0.6 | 1 |
| 540 | 40 | LYS | CB | C | 36.3 | 0.6 | 1 |
| 541 | 40 | LYS | CG | C | 24.9 | 0.6 | 1 |
| 542 | 40 | LYS | CD | C | 29.0 | 0.6 | 1 |
| 543 | 40 | LYS | CE | C | 42.0 | 0.6 | 1 |
| 544 | 40 | LYS | N | N | 118.0 | 0.3 | 1 |
| 546 | 41 | CYS | H | H | 8.95 | 0.02 | 1 |
| 547 | 41 | CYS | HA | H | 5.29 | 0.02 | 1 |
| 548 | 41 | CYS | HB2 | H | 3.00 | 0.02 | 1 |
| 549 | 41 | CYS | HB3 | H | 2.58 | 0.02 | 1 |
| 551 | 41 | CYS | C | C | 174.4 | 0.6 | 1 |
| 552 | 41 | CYS | CA | C | 55.0 | 0.6 | 1 |
| 553 | 41 | CYS | CB | C | 41.9 | 0.6 | 1 |
| 554 | 41 | CYS | N | N | 119.8 | 0.3 | 1 |
| 555 | 42 | VAL | H | H | 9.35 | 0.02 | 1 |
| 556 | 42 | VAL | HA | H | 4.88 | 0.02 | 1 |
| 557 | 42 | VAL | HB | H | 2.32 | 0.02 | 1 |
| 558 | 42 | VAL | HG1 | H | 1.00 | 0.02 | 1 |
| 559 | 42 | VAL | HG2 | H | 0.88 | 0.02 | 1 |
| 560 | 42 | VAL | C | C | 175.2 | 0.6 | 1 |
| 561 | 42 | VAL | CA | C | 59.2 | 0.6 | 1 |
| 562 | 42 | VAL | CB | C | 35.2 | 0.6 | 1 |
| 563 | 42 | VAL | CG1 | C | 21.6 | 0.6 | 1 |
| 564 | 42 | VAL | CG2 | C | 19.3 | 0.6 | 1 |
| 565 | 42 | VAL | N | N | 118.7 | 0.3 | 1 |
| 566 | 43 | GLU | H | H | 9.18 | 0.02 | 1 |
| 567 | 43 | GLU | HA | H | 3.34 | 0.02 | 1 |
| 568 | 43 | GLU | HB2 | H | 1.84 | 0.02 | 2 |
| 569 | 43 | GLU | HB3 | H | 1.75 | 0.02 | 2 |
| 570 | 43 | GLU | HG2 | H | 2.15 | 0.02 | 2 |
| 571 | 43 | GLU | HG3 | H | 2.07 | 0.02 | 2 |
| 572 | 43 | GLU | C | C | 175.4 | 0.6 | 1 |
| 573 | 43 | GLU | CA | C | 59.0 | 0.6 | 1 |
| 574 | 43 | GLU | CB | C | 29.8 | 0.6 | 1 |
| 575 | 43 | GLU | CG | C | 36.8 | 0.6 | 1 |
| 577 | 43 | GLU | N | N | 123.4 | 0.3 | 1 |
| 578 | 44 | ASN | H | H | 8.25 | 0.02 | 1 |
| 579 | 44 | ASN | HA | H | 4.95 | 0.02 | 1 |
| 580 | 44 | ASN | HB2 | H | 2.72 | 0.02 | 2 |
| 581 | 44 | ASN | HB3 | H | 1.97 | 0.02 | 2 |
| 582 | 44 | ASN | HD21 | H | 8.07 | 0.02 | 2 |
| 583 | 44 | ASN | HD22 | H | 7.24 | 0.02 | 2 |
| 584 | 44 | ASN | C | C | ? | ? | ? |
| 585 | 44 | ASN | CA | C | 48.5 | 0.6 | 1 |
| 586 | 44 | ASN | CB | C | 39.2 | 0.6 | 1 |
| 588 | 44 | ASN | N | N | 120.2 | 0.3 | 1 |
| 589 | 44 | ASN | ND2 | N | 112.1 | 0.3 | 1 |
| 590 | 45 | PRO | HA | H | 4.40 | 0.02 | 1 |
| 591 | 45 | PRO | HB2 | H | 2.31 | 0.02 | 1 |
| 592 | 45 | PRO | HB3 | H | 1.95 | 0.02 | 1 |
| 593 | 45 | PRO | HG2 | H | 1.97 | 0.02 | 1 |
| 594 | 45 | PRO | HG3 | H | 1.97 | 0.02 | 1 |
| 595 | 45 | PRO | HD2 | H | 3.86 | 0.02 | 2 |
| 596 | 45 | PRO | HD3 | H | 3.81 | 0.02 | 2 |
| 597 | 45 | PRO | C | C | 176.2 | 0.6 | 1 |
| 598 | 45 | PRO | CA | C | 63.7 | 0.6 | 1 |
| 599 | 45 | PRO | CB | C | 32.6 | 0.6 | 1 |
| 600 | 45 | PRO | CG | C | 26.8 | 0.6 | 1 |
| 601 | 45 | PRO | CD | C | 50.9 | 0.6 | 1 |
| 603 | 46 | ASN | H | H | 7.47 | 0.02 | 1 |
| 604 | 46 | ASN | HA | H | 5.09 | 0.02 | 1 |
| 605 | 46 | ASN | HB2 | H | 2.72 | 0.02 | 2 |
| 606 | 46 | ASN | HB3 | H | 2.43 | 0.02 | 2 |
| 607 | 46 | ASN | HD21 | H | 7.57 | 0.02 | 1 |
| 608 | 46 | ASN | HD22 | H | 6.91 | 0.02 | 1 |
| 609 | 46 | ASN | C | C | ? | ? | ? |
| 610 | 46 | ASN | CA | C | 51.6 | 0.6 | 1 |
| 611 | 46 | ASN | CB | C | 40.1 | 0.6 | 1 |
| 613 | 46 | ASN | N | N | 114.0 | 0.3 | 1 |
| 614 | 46 | ASN | ND2 | N | 112.6 | 0.3 | 1 |
| 615 | 47 | PRO | HA | H | 4.34 | 0.02 | 1 |
| 616 | 47 | PRO | HB2 | H | 1.97 | 0.02 | 1 |
| 617 | 47 | PRO | HB3 | H | 1.77 | 0.02 | 1 |
| 618 | 47 | PRO | HG2 | H | 1.96 | 0.02 | 1 |
| 619 | 47 | PRO | HG3 | H | 1.96 | 0.02 | 1 |
| 620 | 47 | PRO | HD2 | H | 3.52 | 0.02 | 2 |
| 621 | 47 | PRO | HD3 | H | 3.39 | 0.02 | 2 |
| 622 | 47 | PRO | C | C | 175.5 | 0.6 | 1 |
| 623 | 47 | PRO | CA | C | 63.7 | 0.6 | 1 |
| 624 | 47 | PRO | CB | C | 32.4 | 0.6 | 1 |
| 625 | 47 | PRO | CG | C | 27.5 | 0.6 | 1 |
| 626 | 47 | PRO | CD | C | 49.8 | 0.6 | 1 |
| 628 | 48 | THR | H | H | 8.28 | 0.02 | 1 |
| 629 | 48 | THR | HA | H | 4.68 | 0.02 | 1 |
| 630 | 48 | THR | HB | H | 4.32 | 0.02 | 1 |
| 632 | 48 | THR | HG2 | H | 1.13 | 0.02 | 1 |
| 633 | 48 | THR | C | C | 174.5 | 0.6 | 1 |
| 634 | 48 | THR | CA | C | 59.1 | 0.6 | 1 |
| 635 | 48 | THR | CB | C | 69.9 | 0.6 | 1 |
| 636 | 48 | THR | CG2 | C | 19.3 | 0.6 | 1 |
| 637 | 48 | THR | N | N | 112.4 | 0.3 | 1 |
| 638 | 49 | CYS | H | H | 9.35 | 0.02 | 1 |
| 639 | 49 | CYS | HA | H | 4.44 | 0.02 | 1 |
| 640 | 49 | CYS | HB2 | H | 2.64 | 0.02 | 1 |
| 641 | 49 | CYS | HB3 | H | 3.14 | 0.02 | 1 |
| 643 | 49 | CYS | C | C | 175.8 | 0.6 | 1 |
| 644 | 49 | CYS | CA | C | 55.5 | 0.6 | 1 |
| 645 | 49 | CYS | CB | C | 37.7 | 0.6 | 1 |
| 646 | 49 | CYS | N | N | 125.3 | 0.3 | 1 |
| 647 | 50 | ASN | H | H | 8.36 | 0.02 | 1 |
| 648 | 50 | ASN | HA | H | 4.60 | 0.02 | 1 |
| 649 | 50 | ASN | HB2 | H | 2.88 | 0.02 | 1 |
| 650 | 50 | ASN | HB3 | H | 2.70 | 0.02 | 1 |
| 651 | 50 | ASN | HD21 | H | 7.60 | 0.02 | 2 |
| 652 | 50 | ASN | HD22 | H | 6.97 | 0.02 | 2 |
| 653 | 50 | ASN | C | C | 174.4 | 0.6 | 1 |
| 654 | 50 | ASN | CA | C | 54.8 | 0.6 | 1 |
| 655 | 50 | ASN | CB | C | 38.9 | 0.6 | 1 |
| 657 | 50 | ASN | N | N | 116.4 | 0.3 | 1 |
| 658 | 50 | ASN | ND2 | N | 113.6 | 0.3 | 1 |
| 659 | 51 | GLU | H | H | 7.43 | 0.02 | 1 |
| 660 | 51 | GLU | HA | H | 4.64 | 0.02 | 1 |
| 661 | 51 | GLU | HB2 | H | 1.96 | 0.02 | 2 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ppm | Error/ppm | Ambiguity Code |
|---|---|---|---|---|---|---|---|
| 662 | 51 | GLU | HB3 | H | 1.81 | 0.02 | 2 |
| 663 | 51 | GLU | HG2 | H | 2.12 | 0.02 | 1 |
| 664 | 51 | GLU | HG3 | H | 2.12 | 0.02 | 1 |
| 665 | 51 | GLU | C | C | 176.1 | 0.6 | 1 |
| 666 | 51 | GLU | CA | C | 55.3 | 0.6 | 1 |
| 667 | 51 | GLU | CB | C | 31.5 | 0.6 | 1 |
| 668 | 51 | GLU | CG | C | 36.1 | 0.6 | 1 |
| 670 | 51 | GLU | N | N | 119.2 | 0.3 | 1 |
| 671 | 52 | ASN | H | H | 9.57 | 0.02 | 1 |
| 672 | 52 | ASN | HA | H | 4.45 | 0.02 | 1 |
| 673 | 52 | ASN | HB2 | H | 3.14 | 0.02 | 1 |
| 674 | 52 | ASN | HB3 | H | 2.64 | 0.02 | 1 |
| 675 | 52 | ASN | HD21 | H | 6.99 | 0.02 | 1 |
| 676 | 52 | ASN | HD22 | H | 7.71 | 0.02 | 1 |
| 677 | 52 | ASN | C | C | 176.4 | 0.6 | 1 |
| 678 | 52 | ASN | CA | C | 54.2 | 0.6 | 1 |
| 679 | 52 | ASN | CB | C | 37.8 | 0.6 | 1 |
| 681 | 52 | ASN | N | N | 125.4 | 0.3 | 1 |
| 682 | 52 | ASN | ND2 | N | 112.8 | 0.3 | 1 |
| 683 | 53 | ASN | H | H | 9.31 | 0.02 | 1 |
| 684 | 53 | ASN | HA | H | 4.64 | 0.02 | 1 |
| 685 | 53 | ASN | HB2 | H | 3.25 | 0.02 | 1 |
| 686 | 53 | ASN | HB3 | H | 2.31 | 0.02 | 1 |
| 687 | 53 | ASN | HD21 | H | 6.95 | 0.02 | 1 |
| 688 | 53 | ASN | HD22 | H | 6.26 | 0.02 | 1 |
| 689 | 53 | ASN | C | C | 176.2 | 0.6 | 1 |
| 690 | 53 | ASN | CA | C | 54.1 | 0.6 | 1 |
| 691 | 53 | ASN | CB | C | 39.2 | 0.6 | 1 |
| 693 | 53 | ASN | N | N | 119.3 | 0.3 | 1 |
| 694 | 53 | ASN | ND2 | N | 111.6 | 0.3 | 1 |
| 695 | 54 | GLY | H | H | 7.92 | 0.02 | 1 |
| 696 | 54 | GLY | HA2 | H | 4.28 | 0.02 | 1 |
| 697 | 54 | GLY | HA3 | H | 3.67 | 0.02 | 1 |
| 698 | 54 | GLY | C | C | 173.0 | 0.6 | 1 |
| 699 | 54 | GLY | CA | C | 46.3 | 0.6 | 1 |
| 700 | 54 | GLY | N | N | 106.3 | 0.3 | 1 |
| 701 | 55 | GLY | H | H | 8.06 | 0.02 | 1 |
| 702 | 55 | GLY | HA2 | H | 4.39 | 0.02 | 1 |
| 703 | 55 | GLY | HA3 | H | 3.47 | 0.02 | 1 |
| 704 | 55 | GLY | C | C | 175.1 | 0.6 | 1 |
| 705 | 55 | GLY | CA | C | 44.4 | 0.6 | 1 |
| 706 | 55 | GLY | N | N | 105.3 | 0.3 | 1 |
| 707 | 56 | CYS | H | H | 7.77 | 0.02 | 1 |
| 708 | 56 | CYS | HA | H | 4.39 | 0.02 | 1 |
| 709 | 56 | CYS | HB2 | H | 3.12 | 0.02 | 1 |
| 710 | 56 | CYS | HB3 | H | 2.81 | 0.02 | 1 |
| 712 | 56 | CYS | C | C | 175.2 | 0.6 | 1 |
| 713 | 56 | CYS | CA | C | 53.1 | 0.6 | 1 |
| 714 | 56 | CYS | CB | C | 36.6 | 0.6 | 1 |
| 715 | 56 | CYS | N | N | 117.6 | 0.3 | 1 |
| 716 | 57 | ASP | H | H | 8.37 | 0.02 | 1 |
| 717 | 57 | ASP | HA | H | 3.98 | 0.02 | 1 |
| 718 | 57 | ASP | HB2 | H | 2.24 | 0.02 | 2 |
| 719 | 57 | ASP | HB3 | H | 2.03 | 0.02 | 2 |
| 720 | 57 | ASP | C | C | 176.0 | 0.6 | 1 |
| 721 | 57 | ASP | CA | C | 56.0 | 0.6 | 1 |
| 722 | 57 | ASP | CB | C | 45.0 | 0.6 | 1 |
| 724 | 57 | ASP | N | N | 122.3 | 0.3 | 1 |
| 725 | 58 | ALA | H | H | 8.48 | 0.02 | 1 |
| 726 | 58 | ALA | HA | H | 3.98 | 0.02 | 1 |
| 727 | 58 | ALA | HB | H | 1.41 | 0.02 | 1 |
| 728 | 58 | ALA | C | C | 178.9 | 0.6 | 1 |
| 729 | 58 | ALA | CA | C | 55.6 | 0.6 | 1 |
| 730 | 58 | ALA | CB | C | 19.1 | 0.6 | 1 |
| 731 | 58 | ALA | N | N | 127.2 | 0.3 | 1 |
| 732 | 59 | ASP | H | H | 9.11 | 0.02 | 1 |
| 733 | 59 | ASP | HA | H | 4.90 | 0.02 | 1 |
| 734 | 59 | ASP | HB2 | H | 2.44 | 0.02 | 1 |
| 735 | 59 | ASP | HB3 | H | 2.82 | 0.02 | 1 |
| 736 | 59 | ASP | C | C | 174.6 | 0.6 | 1 |
| 737 | 59 | ASP | CA | C | 53.9 | 0.6 | 1 |
| 738 | 59 | ASP | CB | C | 40.7 | 0.6 | 1 |
| 740 | 59 | ASP | N | N | 116.7 | 0.3 | 1 |
| 741 | 60 | ALA | H | H | 7.94 | 0.02 | 1 |
| 742 | 60 | ALA | HA | H | 5.13 | 0.02 | 1 |
| 743 | 60 | ALA | HB | H | 1.27 | 0.02 | 1 |
| 744 | 60 | ALA | C | C | 176.3 | 0.6 | 1 |
| 745 | 60 | ALA | CA | C | 50.5 | 0.6 | 1 |
| 746 | 60 | ALA | CB | C | 21.3 | 0.6 | 1 |
| 747 | 60 | ALA | N | N | 121.9 | 0.3 | 1 |
| 748 | 61 | LYS | H | H | 9.06 | 0.02 | 1 |
| 749 | 61 | LYS | HA | H | 4.54 | 0.02 | 1 |
| 750 | 61 | LYS | HB2 | H | 1.77 | 0.02 | 1 |
| 751 | 61 | LYS | HB3 | H | 1.77 | 0.02 | 1 |
| 752 | 61 | LYS | HG2 | H | 1.31 | 0.02 | 2 |
| 753 | 61 | LYS | HG3 | H | 1.39 | 0.02 | 2 |
| 754 | 61 | LYS | HD2 | H | 1.72 | 0.02 | 2 |
| 755 | 61 | LYS | HD3 | H | 1.63 | 0.02 | 2 |
| 756 | 61 | LYS | HE2 | H | 2.92 | 0.02 | 2 |
| 757 | 61 | LYS | HE3 | H | 2.92 | 0.02 | 2 |
| 759 | 61 | LYS | C | C | 175.7 | 0.6 | 1 |
| 760 | 61 | LYS | CA | C | 55.1 | 0.6 | 1 |
| 761 | 61 | LYS | CB | C | 34.1 | 0.6 | 1 |
| 762 | 61 | LYS | CG | C | 24.6 | 0.6 | 1 |
| 763 | 61 | LYS | CD | C | 29.1 | 0.6 | 1 |
| 764 | 61 | LYS | CE | C | 42.1 | 0.6 | 1 |
| 765 | 61 | LYS | N | N | 122.5 | 0.3 | 1 |
| 767 | 62 | CYS | H | H | 9.19 | 0.02 | 1 |
| 768 | 62 | CYS | HA | H | 5.32 | 0.02 | 1 |
| 769 | 62 | CYS | HB2 | H | 2.44 | 0.02 | 1 |
| 770 | 62 | CYS | HB3 | H | 2.80 | 0.02 | 1 |
| 772 | 62 | CYS | C | C | 174.5 | 0.6 | 1 |
| 773 | 62 | CYS | CA | C | 56.1 | 0.6 | 1 |
| 774 | 62 | CYS | CB | C | 37.6 | 0.6 | 1 |
| 775 | 62 | CYS | N | N | 131.5 | 0.3 | 1 |
| 776 | 63 | THR | H | H | 9.23 | 0.02 | 1 |
| 777 | 63 | THR | HA | H | 4.51 | 0.02 | 1 |
| 778 | 63 | THR | HB | H | 4.01 | 0.02 | 1 |
| 780 | 63 | THR | HG2 | H | 1.16 | 0.02 | 1 |
| 781 | 63 | THR | C | C | 172.2 | 0.6 | 1 |
| 782 | 63 | THR | CA | C | 62.8 | 0.6 | 1 |
| 783 | 63 | THR | CB | C | 71.5 | 0.6 | 1 |
| 784 | 63 | THR | CG2 | C | 22.0 | 0.6 | 1 |
| 785 | 63 | THR | N | N | 125.9 | 0.3 | 1 |
| 786 | 64 | GLU | H | H | 8.61 | 0.02 | 1 |
| 787 | 64 | GLU | HA | H | 5.12 | 0.02 | 1 |
| 788 | 64 | GLU | HB2 | H | 1.90 | 0.02 | 1 |
| 789 | 64 | GLU | HB3 | H | 1.90 | 0.02 | 1 |
| 790 | 64 | GLU | HG2 | H | 2.30 | 0.02 | 1 |
| 791 | 64 | GLU | HG3 | H | 2.30 | 0.02 | 1 |
| 792 | 64 | GLU | C | C | ? | ? | ? |
| 793 | 64 | GLU | CA | C | 54.4 | 0.6 | 1 |
| 794 | 64 | GLU | CB | C | 32.0 | 0.6 | 1 |
| 795 | 64 | GLU | CG | C | 36.8 | 0.6 | 1 |
| 797 | 64 | GLU | N | N | 123.0 | 0.3 | 1 |
| 798 | 65 | GLU | H | H | 8.76 | 0.02 | 1 |
| 799 | 65 | GLU | HA | H | 4.60 | 0.02 | 1 |
| 800 | 65 | GLU | HB2 | H | 2.01 | 0.02 | 2 |
| 801 | 65 | GLU | HB3 | H | 1.86 | 0.02 | 2 |
| 802 | 65 | GLU | HG2 | H | 2.15 | 0.02 | 1 |
| 803 | 65 | GLU | HG3 | H | 2.15 | 0.02 | 1 |
| 804 | 65 | GLU | C | C | ? | ? | ? |
| 805 | 65 | GLU | CA | C | 55.1 | 0.6 | 1 |
| 806 | 65 | GLU | CB | C | 32.9 | 0.6 | 1 |
| 807 | 65 | GLU | CG | C | 36.1 | 0.6 | 1 |
| 809 | 65 | GLU | N | N | 123.0 | 0.3 | 1 |
| 810 | 66 | ASP | H | H | 8.79 | 0.02 | 1 |
| 811 | 66 | ASP | HA | H | 4.80 | 0.02 | 1 |
| 812 | 66 | ASP | HB2 | H | 2.80 | 0.02 | 2 |
| 813 | 66 | ASP | HB3 | H | 2.58 | 0.02 | 2 |
| 814 | 66 | ASP | C | C | 176.4 | 0.6 | 1 |
| 815 | 66 | ASP | CA | C | 54.8 | 0.6 | 1 |
| 816 | 66 | ASP | CB | C | 41.2 | 0.6 | 1 |
| 818 | 66 | ASP | N | N | 123.9 | 0.3 | 1 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 819 | 67 | SER | H | H | 8.38 | 0.02 | 1 |
| 820 | 67 | SER | HA | H | 4.55 | 0.02 | 1 |
| 821 | 67 | SER | HB2 | H | 3.83 | 0.02 | 2 |
| 822 | 67 | SER | HB3 | H | 3.70 | 0.02 | 2 |
| 824 | 67 | SER | C | C | 175.4 | 0.6 | 1 |
| 825 | 67 | SER | CA | C | 58.0 | 0.6 | 1 |
| 826 | 67 | SER | CB | C | 64.6 | 0.6 | 1 |
| 827 | 67 | SER | N | N | 119.1 | 0.3 | 1 |
| 828 | 68 | GLY | H | H | 8.65 | 0.02 | 1 |
| 829 | 68 | GLY | HA2 | H | 4.13 | 0.02 | 2 |
| 830 | 68 | GLY | HA3 | H | 3.85 | 0.02 | 2 |
| 831 | 68 | GLY | C | C | 175.0 | 0.6 | 1 |
| 832 | 68 | GLY | CA | C | 46.0 | 0.6 | 1 |
| 833 | 68 | GLY | N | N | 112.2 | 0.3 | 1 |
| 834 | 69 | SER | H | H | 8.58 | 0.02 | 1 |
| 835 | 69 | SER | HA | H | 4.42 | 0.02 | 1 |
| 836 | 69 | SER | HB2 | H | 3.87 | 0.02 | 2 |
| 837 | 69 | SER | HB3 | H | 3.87 | 0.02 | 2 |
| 839 | 69 | SER | C | C | 174.8 | 0.6 | 1 |
| 840 | 69 | SER | CA | C | 59.1 | 0.6 | 1 |
| 841 | 69 | SER | CB | C | 63.4 | 0.6 | 1 |
| 842 | 69 | SER | N | N | 117.7 | 0.3 | 1 |
| 843 | 70 | ASN | H | H | 8.39 | 0.02 | 1 |
| 844 | 70 | ASN | HA | H | 4.74 | 0.02 | 1 |
| 845 | 70 | ASN | HB2 | H | 2.94 | 0.02 | 2 |
| 846 | 70 | ASN | HB3 | H | 2.77 | 0.02 | 2 |
| 847 | 70 | ASN | HD21 | H | ? | ? | ? |
| 848 | 70 | ASN | HD22 | H | ? | ? | ? |
| 849 | 70 | ASN | C | C | ? | ? | ? |
| 850 | 70 | ASN | CA | C | 53.8 | 0.6 | 1 |
| 851 | 70 | ASN | CB | C | 38.9 | 0.6 | 1 |
| 853 | 70 | ASN | N | N | 118.4 | 0.3 | 1 |
| 854 | 70 | ASN | ND2 | N | ? | ? | ? |
| 855 | 71 | GLY | H | H | 7.88 | 0.02 | 1 |
| 856 | 71 | GLY | HA2 | H | 4.07 | 0.02 | 1 |
| 857 | 71 | GLY | HA3 | H | 4.07 | 0.02 | 1 |
| 858 | 71 | GLY | C | C | 173.7 | 0.6 | 1 |
| 859 | 71 | GLY | CA | C | 45.0 | 0.6 | 1 |
| 860 | 71 | GLY | N | N | 108.1 | 0.3 | 1 |
| 861 | 72 | LYS | H | H | 8.39 | 0.02 | 1 |
| 862 | 72 | LYS | HA | H | 4.84 | 0.02 | 1 |
| 863 | 72 | LYS | HB2 | H | 1.75 | 0.02 | 2 |
| 864 | 72 | LYS | HB3 | H | 1.59 | 0.02 | 2 |
| 865 | 72 | LYS | HG2 | H | 1.46 | 0.02 | 2 |
| 866 | 72 | LYS | HG3 | H | 1.38 | 0.02 | 2 |
| 867 | 72 | LYS | HD2 | H | 1.66 | 0.02 | 1 |
| 868 | 72 | LYS | HD3 | H | 1.66 | 0.02 | 1 |
| 869 | 72 | LYS | HE2 | H | 2.93 | 0.02 | 1 |
| 870 | 72 | LYS | HE3 | H | 2.93 | 0.02 | 1 |
| 872 | 72 | LYS | C | C | 173.7 | 0.6 | 1 |
| 873 | 72 | LYS | CA | C | 55.4 | 0.6 | 1 |
| 874 | 72 | LYS | CB | C | 35.0 | 0.6 | 1 |
| 875 | 72 | LYS | CG | C | 24.9 | 0.6 | 1 |
| 876 | 72 | LYS | CD | C | 28.9 | 0.6 | 1 |
| 877 | 72 | LYS | CE | C | 42.2 | 0.6 | 1 |
| 878 | 72 | LYS | N | N | 120.8 | 0.3 | 1 |
| 880 | 73 | LYS | H | H | 8.81 | 0.02 | 1 |
| 881 | 73 | LYS | HA | H | 4.64 | 0.02 | 1 |
| 882 | 73 | LYS | HB2 | H | 1.71 | 0.02 | 1 |
| 883 | 73 | LYS | HB3 | H | 1.71 | 0.02 | 1 |
| 884 | 73 | LYS | HG2 | H | 1.36 | 0.02 | 2 |
| 885 | 73 | LYS | HG3 | H | 1.25 | 0.02 | 2 |
| 886 | 73 | LYS | HD2 | H | 1.63 | 0.02 | 1 |
| 887 | 73 | LYS | HD3 | H | 1.63 | 0.02 | 1 |
| 888 | 73 | LYS | HE2 | H | 2.89 | 0.02 | 1 |
| 889 | 73 | LYS | HE3 | H | 2.89 | 0.02 | 1 |
| 891 | 73 | LYS | C | C | 175.3 | 0.6 | 1 |
| 892 | 73 | LYS | CA | C | 55.0 | 0.6 | 1 |
| 893 | 73 | LYS | CB | C | 35.4 | 0.6 | 1 |
| 894 | 73 | LYS | CG | C | 24.6 | 0.6 | 1 |
| 895 | 73 | LYS | CD | C | ? | ? | ? |
| 896 | 73 | LYS | CE | C | ? | ? | ? |
| 897 | 73 | LYS | N | N | 122.6 | 0.3 | 1 |
| 899 | 74 | ILE | H | H | 8.54 | 0.02 | 1 |
| 900 | 74 | ILE | HA | H | 4.83 | 0.02 | 1 |
| 901 | 74 | ILE | HB | H | 1.91 | 0.02 | 1 |
| 902 | 74 | ILE | HG12 | H | 1.50 | 0.02 | 2 |
| 903 | 74 | ILE | HG13 | H | 1.50 | 0.02 | 2 |
| 904 | 74 | ILE | HG2 | H | 1.00 | 0.02 | 1 |
| 905 | 74 | ILE | HD1 | H | 0.57 | 0.02 | 1 |
| 906 | 74 | ILE | C | C | 176.2 | 0.6 | 1 |
| 907 | 74 | ILE | CA | C | 58.4 | 0.6 | 1 |
| 908 | 74 | ILE | CB | C | 38.4 | 0.6 | 1 |
| 909 | 74 | ILE | CG1 | C | 27.1 | 0.6 | 1 |
| 910 | 74 | ILE | CG2 | C | 19.0 | 0.6 | 1 |
| 911 | 74 | ILE | CD1 | C | 10.3 | 0.6 | 1 |
| 912 | 74 | ILE | N | N | 126.8 | 0.3 | 1 |
| 913 | 75 | THR | H | H | 8.88 | 0.02 | 1 |
| 914 | 75 | THR | HA | H | 4.51 | 0.02 | 1 |
| 915 | 75 | THR | HB | H | 4.01 | 0.02 | 1 |
| 917 | 75 | THR | HG2 | H | 1.15 | 0.02 | 1 |
| 918 | 75 | THR | C | C | 172.4 | 0.6 | 1 |
| 919 | 75 | THR | CA | C | 61.2 | 0.6 | 1 |
| 920 | 75 | THR | CB | C | 71.5 | 0.6 | 1 |
| 921 | 75 | THR | CG2 | C | 22.0 | 0.6 | 1 |
| 922 | 75 | THR | N | N | 120.3 | 0.3 | 1 |
| 923 | 76 | CYS | H | H | 8.82 | 0.02 | 1 |
| 924 | 76 | CYS | HA | H | 5.53 | 0.02 | 1 |
| 925 | 76 | CYS | HB2 | H | 3.28 | 0.02 | 1 |
| 926 | 76 | CYS | HB3 | H | 2.69 | 0.02 | 1 |
| 928 | 76 | CYS | C | C | 174.7 | 0.6 | 1 |
| 929 | 76 | CYS | CA | C | 52.2 | 0.6 | 1 |
| 930 | 76 | CYS | CB | C | 40.6 | 0.6 | 1 |
| 931 | 76 | CYS | N | N | 121.5 | 0.3 | 1 |
| 932 | 77 | GLU | H | H | 8.64 | 0.02 | 1 |
| 933 | 77 | GLU | HA | H | 4.74 | 0.02 | 1 |
| 934 | 77 | GLU | HB2 | H | 1.94 | 0.02 | 1 |
| 935 | 77 | GLU | HB3 | H | 1.94 | 0.02 | 1 |
| 936 | 77 | GLU | HG2 | H | 1.83 | 0.02 | 1 |
| 937 | 77 | GLU | HG3 | H | 1.83 | 0.02 | 1 |
| 938 | 77 | GLU | C | C | 175.7 | 0.6 | 1 |
| 939 | 77 | GLU | CA | C | 54.7 | 0.6 | 1 |
| 940 | 77 | GLU | CB | C | 33.1 | 0.6 | 1 |
| 941 | 77 | GLU | CG | C | 36.1 | 0.6 | 1 |
| 943 | 77 | GLU | N | N | 123.0 | 0.3 | 1 |
| 944 | 78 | CYS | H | H | 9.71 | 0.02 | 1 |
| 945 | 78 | CYS | HA | H | 4.48 | 0.02 | 1 |
| 946 | 78 | CYS | HB2 | H | 2.63 | 0.02 | 1 |
| 947 | 78 | CYS | HB3 | H | 3.30 | 0.02 | 1 |
| 949 | 78 | CYS | C | C | 175.8 | 0.6 | 1 |
| 950 | 78 | CYS | CA | C | 57.4 | 0.6 | 1 |
| 951 | 78 | CYS | CB | C | 39.2 | 0.6 | 1 |
| 952 | 78 | CYS | N | N | 129.1 | 0.3 | 1 |
| 953 | 79 | THR | H | H | 8.20 | 0.02 | 1 |
| 954 | 79 | THR | HA | H | 4.25 | 0.02 | 1 |
| 955 | 79 | THR | HB | H | 4.25 | 0.02 | 1 |
| 957 | 79 | THR | HG2 | H | 1.25 | 0.02 | 1 |
| 958 | 79 | THR | C | C | 176.2 | 0.6 | 1 |
| 959 | 79 | THR | CA | C | 63.4 | 0.6 | 1 |
| 960 | 79 | THR | CB | C | 70.1 | 0.6 | 1 |
| 961 | 79 | THR | CG2 | C | 22.2 | 0.6 | 1 |
| 962 | 79 | THR | N | N | 114.7 | 0.3 | 1 |
| 963 | 80 | LYS | H | H | 8.56 | 0.02 | 1 |
| 964 | 80 | LYS | HA | H | 4.50 | 0.02 | 1 |
| 965 | 80 | LYS | HB2 | H | 1.79 | 0.02 | 1 |
| 966 | 80 | LYS | HB3 | H | 1.79 | 0.02 | 1 |
| 967 | 80 | LYS | HG2 | H | 1.47 | 0.02 | 2 |
| 968 | 80 | LYS | HG3 | H | 1.64 | 0.02 | 2 |
| 969 | 80 | LYS | HD2 | H | 1.70 | 0.02 | 1 |
| 970 | 80 | LYS | HD3 | H | 1.70 | 0.02 | 1 |
| 971 | 80 | LYS | HE2 | H | 2.94 | 0.02 | 1 |
| 972 | 80 | LYS | HE3 | H | 2.94 | 0.02 | 1 |
| 974 | 80 | LYS | C | C | ? | ? | ? |
| 975 | 80 | LYS | CA | C | 55.4 | 0.6 | 1 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 976 | 80 | LYS | CB | C | 30.9 | 0.6 | 1 |
| 977 | 80 | LYS | CG | C | 25.6 | 0.6 | 1 |
| 978 | 80 | LYS | CD | C | 29.1 | 0.6 | 1 |
| 979 | 80 | LYS | CE | C | 42.1 | 0.6 | 1 |
| 980 | 80 | LYS | N | N | 124.8 | 0.3 | 1 |
| 982 | 81 | PRO | HA | H | 4.26 | 0.02 | 1 |
| 983 | 81 | PRO | HB2 | H | 2.27 | 0.02 | 1 |
| 984 | 81 | PRO | HB3 | H | 1.87 | 0.02 | 1 |
| 985 | 81 | PRO | HG2 | H | 2.10 | 0.02 | 2 |
| 986 | 81 | PRO | HG3 | H | 2.04 | 0.02 | 2 |
| 987 | 81 | PRO | HD2 | H | 3.90 | 0.02 | 2 |
| 988 | 81 | PRO | HD3 | H | 3.63 | 0.02 | 2 |
| 989 | 81 | PRO | C | C | 176.9 | 0.6 | 1 |
| 990 | 81 | PRO | CA | C | 64.2 | 0.6 | 1 |
| 991 | 81 | PRO | CB | C | 31.9 | 0.6 | 1 |
| 992 | 81 | PRO | CG | C | 27.8 | 0.6 | 1 |
| 993 | 81 | PRO | CD | C | 50.8 | 0.6 | 1 |
| 995 | 82 | ASP | H | H | 8.78 | 0.02 | 1 |
| 996 | 82 | ASP | HA | H | 4.25 | 0.02 | 1 |
| 997 | 82 | ASP | HB2 | H | 2.88 | 0.02 | 2 |
| 998 | 82 | ASP | HB3 | H | 2.77 | 0.02 | 2 |
| 999 | 82 | ASP | C | C | ? | ? | ? |
| 1000 | 82 | ASP | CA | C | 55.1 | 0.6 | 1 |
| 1001 | 82 | ASP | CB | C | 40.0 | 0.6 | 1 |
| 1003 | 82 | ASP | N | N | 117.9 | 0.3 | 1 |
| 1004 | 83 | SER | H | H | 7.39 | 0.02 | 1 |
| 1005 | 83 | SER | HA | H | 4.47 | 0.02 | 1 |
| 1006 | 83 | SER | HB2 | H | 3.55 | 0.02 | 2 |
| 1007 | 83 | SER | HB3 | H | 3.50 | 0.02 | 2 |
| 1009 | 83 | SER | C | C | 175.4 | 0.6 | 1 |
| 1010 | 83 | SER | CA | C | 57.4 | 0.6 | 1 |
| 1011 | 83 | SER | CB | C | 65.9 | 0.6 | 1 |
| 1012 | 83 | SER | N | N | 112.9 | 0.3 | 1 |
| 1013 | 84 | TYR | H | H | 8.72 | 0.02 | 1 |
| 1014 | 84 | TYR | HA | H | 5.01 | 0.02 | 1 |
| 1015 | 84 | TYR | HB2 | H | 2.93 | 0.02 | 2 |
| 1016 | 84 | TYR | HB3 | H | 2.75 | 0.02 | 2 |
| 1017 | 84 | TYR | HD1 | H | 6.92 | 0.02 | 1 |
| 1018 | 84 | TYR | HD2 | H | 6.92 | 0.02 | 1 |
| 1019 | 84 | TYR | HE1 | H | 6.69 | 0.02 | 1 |
| 1020 | 84 | TYR | HE2 | H | 6.69 | 0.02 | 1 |
| 1022 | 84 | TYR | C | C | ? | ? | ? |
| 1023 | 84 | TYR | CA | C | 54.6 | 0.6 | 1 |
| 1024 | 84 | TYR | CB | C | 39.7 | 0.6 | 1 |
| 1031 | 84 | TYR | N | N | 122.2 | 0.3 | 1 |
| 1032 | 85 | PRO | HA | H | 5.09 | 0.02 | 1 |
| 1033 | 85 | PRO | HB2 | H | 2.25 | 0.02 | 2 |
| 1034 | 85 | PRO | HB3 | H | 1.72 | 0.02 | 2 |
| 1035 | 85 | PRO | HG2 | H | 2.22 | 0.02 | 1 |
| 1036 | 85 | PRO | HG3 | H | 2.22 | 0.02 | 1 |
| 1037 | 85 | PRO | HD2 | H | 3.85 | 0.02 | 1 |
| 1038 | 85 | PRO | HD3 | H | 3.85 | 0.02 | 1 |
| 1039 | 85 | PRO | C | C | 176.9 | 0.6 | 1 |
| 1040 | 85 | PRO | CA | C | 62.9 | 0.6 | 1 |
| 1041 | 85 | PRO | CB | C | 32.8 | 0.6 | 1 |
| 1042 | 85 | PRO | CG | C | 27.3 | 0.6 | 1 |
| 1043 | 85 | PRO | CD | C | 50.6 | 0.6 | 1 |
| 1045 | 86 | LEU | H | H | 8.51 | 0.02 | 1 |
| 1046 | 86 | LEU | HA | H | 4.77 | 0.02 | 1 |
| 1047 | 86 | LEU | HB2 | H | 1.76 | 0.02 | 1 |
| 1048 | 86 | LEU | HB3 | H | 1.76 | 0.02 | 1 |
| 1049 | 86 | LEU | HG | H | 1.85 | 0.02 | 1 |
| 1050 | 86 | LEU | HD1 | H | 1.00 | 0.02 | 1 |
| 1051 | 86 | LEU | HD2 | H | 1.00 | 0.02 | 1 |
| 1052 | 86 | LEU | C | C | 177.9 | 0.6 | 1 |
| 1053 | 86 | LEU | CA | C | 54.5 | 0.6 | 1 |
| 1054 | 86 | LEU | CB | C | 44.8 | 0.6 | 1 |
| 1055 | 86 | LEU | CG | C | 29.0 | 0.6 | 1 |
| 1056 | 86 | LEU | CD1 | C | 25.7 | 0.6 | 1 |
| 1057 | 86 | LEU | CD2 | C | 25.7 | 0.6 | 1 |
| 1058 | 86 | LEU | N | N | 120.2 | 0.3 | 1 |
| 1059 | 87 | PHE | H | H | 9.29 | 0.02 | 1 |
| 1060 | 87 | PHE | HA | H | 4.16 | 0.02 | 1 |
| 1061 | 87 | PHE | HB2 | H | 3.26 | 0.02 | 2 |
| 1062 | 87 | PHE | HB3 | H | 3.19 | 0.02 | 2 |
| 1063 | 87 | PHE | HD1 | H | 7.31 | 0.02 | 1 |
| 1064 | 87 | PHE | HD2 | H | 7.31 | 0.02 | 1 |
| 1065 | 87 | PHE | HE1 | H | 7.70 | 0.02 | 1 |
| 1066 | 87 | PHE | HE2 | H | 7.70 | 0.02 | 1 |
| 1067 | 87 | PHE | HZ | H | 7.67 | 0.02 | 1 |
| 1068 | 87 | PHE | C | C | 176.4 | 0.6 | 1 |
| 1069 | 87 | PHE | CA | C | 59.3 | 0.6 | 1 |
| 1070 | 87 | PHE | CB | C | 36.9 | 0.6 | 1 |
| 1077 | 87 | PHE | N | N | 122.6 | 0.3 | 1 |
| 1078 | 88 | ASP | H | H | 8.93 | 0.02 | 1 |
| 1079 | 88 | ASP | HA | H | 4.33 | 0.02 | 1 |
| 1080 | 88 | ASP | HB2 | H | 3.11 | 0.02 | 2 |
| 1081 | 88 | ASP | HB3 | H | 3.02 | 0.02 | 2 |
| 1082 | 88 | ASP | C | C | 175.2 | 0.6 | 1 |
| 1083 | 88 | ASP | CA | C | 56.3 | 0.6 | 1 |
| 1084 | 88 | ASP | CB | C | 39.9 | 0.6 | 1 |
| 1086 | 88 | ASP | N | N | 111.3 | 0.3 | 1 |
| 1087 | 89 | GLY | H | H | 7.87 | 0.02 | 1 |
| 1088 | 89 | GLY | HA2 | H | 3.48 | 0.02 | 1 |
| 1089 | 89 | GLY | HA3 | H | 4.08 | 0.02 | 1 |
| 1090 | 89 | GLY | C | C | 174.7 | 0.6 | 1 |
| 1091 | 89 | GLY | CA | C | 46.0 | 0.6 | 1 |
| 1092 | 89 | GLY | N | N | 102.0 | 0.3 | 1 |
| 1093 | 90 | ILE | H | H | 7.17 | 0.02 | 1 |
| 1094 | 90 | ILE | HA | H | 4.39 | 0.02 | 1 |
| 1095 | 90 | ILE | HB | H | 1.52 | 0.02 | 1 |
| 1096 | 90 | ILE | HG12 | H | 0.65 | 0.02 | 2 |
| 1097 | 90 | ILE | HG13 | H | 0.65 | 0.02 | 2 |
| 1098 | 90 | ILE | HG2 | H | 1.05 | 0.02 | 1 |
| 1099 | 90 | ILE | HD1 | H | 0.51 | 0.02 | 1 |
| 1100 | 90 | ILE | C | C | 175.1 | 0.6 | 1 |
| 1101 | 90 | ILE | CA | C | 64.2 | 0.6 | 1 |
| 1102 | 90 | ILE | CB | C | 35.9 | 0.6 | 1 |
| 1103 | 90 | ILE | CG1 | C | 25.5 | 0.6 | 1 |
| 1104 | 90 | ILE | CG2 | C | 16.9 | 0.6 | 1 |
| 1105 | 90 | ILE | CD1 | C | 14.9 | 0.6 | 1 |
| 1106 | 90 | ILE | N | N | 113.3 | 0.3 | 1 |
| 1107 | 91 | PHE | H | H | 7.43 | 0.02 | 1 |
| 1108 | 91 | PHE | HA | H | 5.15 | 0.02 | 1 |
| 1109 | 91 | PHE | HB2 | H | 2.40 | 0.02 | 1 |
| 1110 | 91 | PHE | HB3 | H | 2.40 | 0.02 | 1 |
| 1111 | 91 | PHE | HD1 | H | 7.00 | 0.02 | 1 |
| 1112 | 91 | PHE | HD2 | H | 7.00 | 0.02 | 1 |
| 1113 | 91 | PHE | HE1 | H | 6.95 | 0.02 | 1 |
| 1114 | 91 | PHE | HE2 | H | 6.95 | 0.02 | 1 |
| 1115 | 91 | PHE | HZ | H | 7.06 | 0.02 | 1 |
| 1116 | 91 | PHE | C | C | 175.1 | 0.6 | 1 |
| 1117 | 91 | PHE | CA | C | 56.5 | 0.6 | 1 |
| 1118 | 91 | PHE | CB | C | 44.3 | 0.6 | 1 |
| 1125 | 91 | PHE | N | N | 114.0 | 0.3 | 1 |
| 1126 | 92 | CYS | H | H | 7.86 | 0.02 | 1 |
| 1127 | 92 | CYS | HA | H | 5.18 | 0.02 | 1 |
| 1128 | 92 | CYS | HB2 | H | 2.57 | 0.02 | 1 |
| 1129 | 92 | CYS | HB3 | H | 3.08 | 0.02 | 1 |
| 1131 | 92 | CYS | C | C | 174.1 | 0.6 | 1 |
| 1132 | 92 | CYS | CA | C | 54.1 | 0.6 | 1 |
| 1133 | 92 | CYS | CB | C | 44.7 | 0.6 | 1 |
| 1134 | 92 | CYS | N | N | 119.0 | 0.3 | 1 |
| 1135 | 93 | SER | H | H | 9.26 | 0.02 | 1 |
| 1136 | 93 | SER | HA | H | 4.23 | 0.02 | 1 |
| 1137 | 93 | SER | HB2 | H | 3.90 | 0.02 | 1 |
| 1138 | 93 | SER | HB3 | H | 3.90 | 0.02 | 1 |
| 1140 | 93 | SER | C | C | ? | ? | ? |
| 1141 | 93 | SER | CA | C | 60.4 | 0.6 | 1 |
| 1142 | 93 | SER | CB | C | 63.7 | 0.6 | 1 |
| 1143 | 93 | SER | N | N | 118.3 | 0.3 | 1 |
| 1144 | 94 | SER | H | H | 8.04 | 0.02 | 1 |
| 1145 | 94 | SER | HA | H | 4.59 | 0.02 | 1 |
| 1146 | 94 | SER | HB2 | H | 3.91 | 0.02 | 1 |

TABLE A1-continued

Supplementary: 1H, 13C and 15N chemical shift assignments of MSP-1 C-terminal fragment

| Atom shift assign | Residue Seq no. | Residue Name | Atom Name | Atom Type | Shift/ ppm | Error/ ppm | Ambiguity Code |
|---|---|---|---|---|---|---|---|
| 1147 | 94 | SER | HB3 | H | 3.91 | 0.02 | 1 |
| 1149 | 94 | SER | C | C | ? | ? | ? |
| 1150 | 94 | SER | CA | C | 58.7 | 0.6 | 1 |
| 1151 | 94 | SER | CB | C | 64.0 | 0.6 | 1 |
| 1152 | 94 | SER | N | N | 114.2 | 0.3 | 1 |
| 1153 | 95 | SER | H | H | ? | ? | ? |
| 1154 | 95 | SER | HA | H | 4.71 | 0.02 | 1 |
| 1155 | 95 | SER | HB2 | H | 4.02 | 0.02 | 2 |
| 1156 | 95 | SER | HB3 | H | 3.94 | 0.02 | 2 |
| 1158 | 95 | SER | C | C | ? | ? | ? |
| 1159 | 95 | SER | CA | C | 58.4 | 0.6 | 1 |
| 1160 | 95 | SER | CB | C | 64.5 | 0.6 | 1 |
| 1161 | 95 | SER | N | N | ? | ? | ? |
| 1162 | 96 | ASN | H | H | ? | ? | ? |
| 1163 | 96 | ASN | HA | H | 4.61 | 0.02 | 1 |
| 1164 | 96 | ASN | HB2 | H | 2.75 | 0.02 | 2 |
| 1165 | 96 | ASN | HB3 | H | 2.60 | 0.02 | 2 |
| 1166 | 96 | ASN | HD21 | H | ? | ? | ? |
| 1167 | 96 | ASN | HD22 | H | ? | ? | ? |
| 1168 | 96 | ASN | C | C | ? | ? | ? |
| 1169 | 96 | ASN | CA | C | 54.3 | 0.6 | 1 |
| 1170 | 96 | ASN | CB | C | 41.8 | 0.6 | 1 |
| 1172 | 96 | ASN | N | N | ? | ? | ? |
| 1173 | 96 | ASN | ND2 | N | ? | ? | ? |
| stop_ | | | | | | | |

The following loop is used to define sets of Atom-shift assignment IDs that represent related ambiguous assignments taken from the above list of assigned chemical shifts. Each element in the set should be separated by a comma, as shown in the example below, and is the assignment ID for a chemical shift assignment that has been given as ambiguity code of 4 or 5. Each set indicates that the observed chemical shifts are related to the defined atoms, but have not been assigned uniquely to a specific atom in the set.

```
    loop_
        _Atom_shift_assign_ID_ambiguity
    #
    # Sets of Atom-shift Assignment Ambiguities
        #
    # -------------------------------
    # Example: 5,4,7
    #
        @
    stop_
```

```
################################################################
----REMARKS----                          ##
################################################################
#   #   #   #   #   #   #   #   #

#PROTECTED BACKBONE AMIDE GROUPS
# (SLOWLY EXCHANGING IN D2O) FOR RESIDUES:
# GLY 17 ,PHE 19 ,GLU 27 ,LYS 29 ,LEU 31 ,
# TYR 34 , LYS 35 , VAL 42 , CYS 56 ,ASP 57 ,
# ALA 60 ,LYS 61 ,THR 63 ,THR 75 , GLU 77,
# LEU 86 ,GLY 89 ,ILE 90 ,PHE 91

#BROAD HN SIGNALS IN [15-N]-HSQC OBSERVED FOR RESIDUES:
# VAL 8 ,LYS 9 ,LYS 10 ,CYS 18 ,ARG 20

#TWO BACKBONE HN CROSSPEAKS OBSERVED FOR RESIDUES:
# HIS 5 : 7.78,113.8/7.74,113.5
# GLN 6 : 7.44,122.6/7.40,122.4

#TWO AVERAGED NH*/HH* SIGNALS OBSERVED FOR RESIDUES:
# ARG 20, ARG 25 : NOT SPECIFICALLY ASSIGNED
# TO INDIVIDUAL ARGININES

#LYS 29 NZ/HZ* SIGNAL: TENTATIVELY ASSIGNED TO
# LYS 29 (BURIED LYSINE SIDE CHAIN)
# BASED ON GREATER PROTECTION FROM H2O EXCHANGE
# THAN OTHER LYSINE NZ/HZ* SIGNALS

#ASPARAGINE SIDE CHAIN AMIDE SIGNALS:
# PROBABLE OVERLAPPING CROSSPEAKS ~112 PPM [15N]
# FOR ASN 1 ,ASN 70 ,ASN 96

                ################################################
#                                    #
                ################################################
```

TABLE A2

Supplementary: NMR experimental details

| Experiment {Reference} | Dimension | Nucleus | Complex Points [after LP] (points) | Spectral width (Hz) | Acquisition Time (ms) | Carrier Frequency (ppm) | Instrument $^1$H-frequency (MHz) | Solvent | Temperature (°C.) | Final data size (points) | Digital Resolution (Hz/point) | Mixing time (ms) | Total time (hr) |
|---|---|---|---|---|---|---|---|---|---|---|---|---|---|
| 2D NOESY | t1 | $^1$H | 400 | 8000 | 50 | 4.74 | 600 | D$_2$O | 25 | 1024 | 7.8 | 75–150 | 22 |
|  | t2 | $^1$H | 2048 | 8000 | 256 | 4.74 |  |  |  | 2048 | 3.9 |  |  |
| 2D NOESY | t1 | $^1$H | 360 | 8000 | 45 | 4.74 | 600 | H$_2$O | 25 | 1024 | 7.8 | 75 | 23 |
|  | t2 | $^1$H | 2048 | 8000 | 256 | 4.74 |  |  |  | 2048 | 3.9 |  |  |
| 2D ROESY | t1 | $^1$H | 260 | 6000 | 43 | 4.74 | 500 | D$_2$O | 25 | 1024 | 5.9 | 60 | 16 |
|  | t2 | $^1$H | 2048 | 6000 | 341 | 4.74 |  |  |  | 2048 | 2.9 |  |  |
| 2D ROESY | t1 | $^1$H | 360 | 7000 | 54 | 4.74 | 500 | H$_2$O | 25 | 1024 | 6.8 | 60 | 62 |
|  | t2 | $^1$H | 2048 | 7000 | 293 | 4.74 |  |  |  | 2048 | 3.4 |  |  |
| 3D [$^{15}$N]-NOESY-HSQ | t1 | $^{15}$N | 36 [64] | 2500 | 14.4 | 121.5 | 500 | H$_2$O | 25 | 128 | 19.5 | 125 | 64 |
|  | t2 | $^1$H | 180 | 7000 | 26 | 4.74 |  |  |  | 512 | 13.7 |  |  |
|  | t3 | $^1$H | 512 | 7000 | 73 | 4.74 |  |  |  | 512 | 13.7 |  |  |
| 3D [$^{15}$N]-ROESY-HSQC | t1 | $^{15}$N | 32 | 2500 | 12.8 | 121.5 | 500 | H$_2$O | 25 | 128 | 19.5 | 60 | 87 |
|  | t2 | $^1$H | 180 | 7000 | 26 | 4.74 |  |  |  | 512 | 13.7 |  |  |
|  | t3 | $^1$H | 512 | 7000 | 73 | 4.74 |  |  |  | 512 | 13.7 |  |  |
| 3D [$^{13}$C]-HMQC-NOESY | t1 | $^1$H | 160 | 7200 | 22 | 4.74 | 600 | D$_2$O | 25 | 512 | 14.1 | 125 | 89 |
|  | t2 | $^{13}$C | 96 | 10000 | 9.6 | 41.0 |  |  |  | 256 | 39.1 |  |  |
|  | t3 | $^1$H | 384 | 7200 | 53 | 4.74 |  |  |  | 1024 | 7.0 |  |  |
| 4D [13C]-HMQC-NOESY-[13C]-HSQC | t1 | $^{13}$C | 18 [24] | 3360 | 5.4 | 40.2 | 600 | D$_2$O | 25 | 64 | 52.5 | 125 | 105 |
|  | t2 | $^1$H | 74 | 3600 | 21 | 3.00 |  |  |  | 256 | 14.1 |  |  |
|  | t3 | $^{13}$C | 18 [24] | 3360 | 5.4 | 40.2 |  |  |  | 64 | 52.5 |  |  |
|  | t4 | $^1$H | 256 | 4500 | 57 | 3.00 |  |  |  | 256 | 17.6 |  |  |
| 4D [$^{13}$C]-HMQC-NOESY-[$^{15}$N]-HSQC | t1 | $^{13}$C | 14 [24] | 3360 | 4.2 | 40.2 | 600 | H$_2$O | 25 | 64 | 52.5 | 125 | 96 |
|  | t2 | $^1$H | 56 | 3600 | 15.6 | 3.00 |  |  |  | 128 | 28.1 |  |  |
|  | t3 | $^{15}$N | 14 [24] | 1800 | 7.8 | 118.9 |  |  |  | 64 | 28.1 |  |  |
|  | t4 | $^1$H | 256 | 7400 | 34.6 | 4.74 |  |  |  | 256 | 29.0 |  |  |
| 2D DQF-COSY | t1 | $^1$H | 1000 | 6000 | 167 | 4.74 | 500 | D$_2$O | 25 | 4096 | 1.5 |  | 31 |
|  | t2 | $^1$H | 2048 | 6000 | 341 | 4.74 |  |  |  | 8192 | 0.7 |  |  |
| 3D HNHA | t1 | $^{15}$N | 35 | 2500 | 14 | 121.5 | 500 | H$_2$O | 25 | 128 | 19.5 |  | 41 |
|  | t2 | $^1$H | 80 | 3500 | 23 | 4.74 |  |  |  | 256 | 13.7 |  |  |
|  | t3 | $^1$H | 512 | 7000 | 73 | 4.74 |  |  |  | 512 | 13.7 |  |  |
| 3D HNHB | t1 | $^{15}$N | 24 [48] | 2500 | 9.6 | 119.1 | 600 | H$_2$O | 25 | 128 | 19.5 |  | 60 |
|  | t2 | $^1$H | 90 | 8000 | 11.3 | 4.74 |  |  |  | 256 | 31.3 |  |  |
|  | t3 | $^1$H | 512 | 8000 | 64 | 4.74 |  |  |  | 1024 | 7.8 |  |  |
| 3D HN(CO)HB | t1 | $^{15}$N | 28 [48] | 1800 | 15.6 | 118.9 | 600 | H$_2$O | 25 | 128 | 14.1 |  | 108 |
|  | t2 | $^1$H | 128 | 8000 | 16 | 4.74 |  |  |  | 512 | 15.6 |  |  |
|  | t3 | $^1$H | 512 | 8000 | 64 | 4.74 |  |  |  | 512 | 15.6 |  |  |
| 2D [$^{15}$N]-[$^{13}$Cγ] Spin-echo HSQC | t1 | $^{15}$N | 80 | 1800 | 44.4 | 118.9 | 600 | H$_2$O | 25 | 256 | 7.0 |  | 13 |
|  | t2 | $^1$H | 1312 | 8000 | 149 | 4.74 |  |  |  | 2048 | 3.9 |  |  |
| 2D [$^{13}$C]-[$^{13}$Cγ] Spin-echo HSQC | t1 | $^{15}$N | 78 | 1800 | 43.3 | 118.9 | 600 | H$_2$O | 25 | 256 | 7.0 |  | 26 |
|  | t2 | $^1$H | 1216 | 8000 | 152 | 4.74 |  |  |  | 2048 | 3.9 |  |  |
| 3D LRCH | t1 | $^{13}$C | 34 | 3017 | 11.3 | 17.9 | 600 | D$_2$O | 25 | 256 | 11.8 |  | 84 |
|  | t2 | $^1$H | 57 | 4800 | 11.9 | 2.25 |  |  |  | 256 | 18.8 |  |  |
|  | t3 | $^1$H | 384 | 4000 | 96 | 2.25 |  |  |  | 1024 | 3.9 |  |  |
| 2D TOCSY | t1 | $^1$H | 360 | 8000 | 45 | 4.74 | 600 | H$_2$O | 25 | 1024 | 7.8 | 66 | 18 |
|  | t2 | $^1$H | 2048 | 8000 | 256 | 4.74 |  |  |  | 2048 | 3.9 |  |  |
| 2D [$^{15}$N]-HSQC | t1 | $^{15}$N | 360 | 4400 | 82 | 119.6 | 600 | H$_2$O | 25 | 2048 | 2.1 |  | 14 |
|  | t2 | $^1$H | 1216 | 8000 | 152 | 4.74 |  |  |  | 4096 | 2.0 |  |  |
| 2D [$^{13}$C]-HSQC | t1 | $^{13}$C | 400 | 12000 | 33.3 | 41.3 | 600 | H$_2$O | 25 | 1024 | 11.7 |  | 2.7 |
|  | t2 | $^1$H | 1216 | 8000 | 152 | 4.74 |  |  |  | 4096 | 2.0 |  |  |
| 3D [$^{15}$N]-TOCSY-HSQ | t1 | $^{15}$N | 38 [64] | 2500 | 15.2 | 119.0 | 600 | H$^2$O | 25 | 128 | 19.5 | 56 | 43 |
|  | t2 | $^1$H | 180 | 8000 | 22.5 | 4.74 |  |  |  | 512 | 15.6 |  |  |
|  | t3 | $^1$H | 512 | 8000 | 64 | 4.74 |  |  |  | 512 | 15.6 |  |  |
| 3D HCCH-TOCSY | t1 | $^1$H | 134 | 5500 | 24.4 | 4.74 | 500 | D$_2$O | 25 | 512 | 10.7 | 17 | 65 |
|  | t2 | $^{13}$C | 128 | 8049 | 15.9 | 41.9 |  |  |  | 512 | 15.7 |  |  |
|  | t3 | $^1$H | 416 | 5500 | 76 | 4.74 |  |  |  | 512 | 10.7 |  |  |
| 3D CBCA(CO)NH | t1 | $^{13}$C | 38 [64] | 10000 | 3.8 | 41.3 | 600 | H$_2$O | 25 | 128 | 78.1 |  | 21 |
|  | t2 | $^{15}$N | 26 [36] | 1800 | 14.4 | 118.9 |  |  |  | 128 | 14.1 |  |  |
|  | t3 | $^1$H | 512 | 8000 | 64 | 4.74 |  |  |  | 512 | 15.6 |  |  |
| 3D CBCANH | t1 | $^{13}$C | 63 [128] | 10000 | 6.3 | 41.3 | 600 | H$_2$O | 25 | 512 | 19.5 |  | 5 |
|  | t2 | $^{15}$N | 26 [52] | 1800 | 14.4 | 118.9 |  |  |  | 128 | 14.1 |  |  |
|  | t3 | $^1$H | 512 | 8000 | 64 | 4.74 |  |  |  | 256 | 31.3 |  |  |
| 3D HNCO | t1 | $^{15}$N | 32 [48] | 1800 | 17.8 | 118.9 | 600 | H$_2$O | 25 | 128 | 14.1 |  | 43 |
|  | t2 | $^{13}$C | 64 | 1811 | 35.3 | 176.0 |  |  |  | 256 | 7.1 |  |  |
|  | t3 | $^1$H | 512 | 8000 | 64 | 4.74 |  |  |  | 512 | 15.6 |  |  |

TABLE B

```
! merozoite surface protein-1 (MSP-l) P. falciparum C-terminal fragment
! X-PLOR format
! 09-11-98
!    noes + roes         approximate - 570 total
!    long-range          185
!    medium-range        90
!    sequential          222
!    intraresidue        73
!    hydrogen_bonds      10 (20 restraints)
! pseudoatom corrections not used - for R-6 averaging/summation
! AVERAGING:
! class rt6s SUM
! class nsam SUM
! class sing
! class hbnd
! types:
!    arom_               aromatic pair
!    meth_               methyl
!    dgnm_               degenerate methylene
!    nsam_               non-stereospecifically-assigned methylene
!    sing_               single proton
!    _l                  long-range     (j−i > 4)
!    _m                  medium-range   (j−i =2–4)
!    _s                  sequential     (j−i = 1)
!    _i                  intraresidue
!    hbnd                hydrogen_bonds
!    <residue-atom 1>        <residue-atom 2>        <dist-minus-plus>           <type>
class rt6s
assign (resid 5 and name hb#)     (resid 19 and name hd#)    3.6  3.6  0.0    !arom_l
assign (resid 5 and name hb#)     (resid 19 and name he#)    3.6  3.6  0.0    !arom_l
assign (resid 15 and name ha)     (resid 34 and name hd#)    3.6  3.6  0.0    !arom_l
assign (resid 15 and name ha)     (resid 34 and name he#)    3.6  3.6  0.0    !arom_l
assign (resid 17 and name ha#)    (resid 87 and name hd#)    5.5  5.5  0.0    !arom_l
assign (resid 17 and name ha#)    (resid 87 and name he#)    5.5  5.5  0.0    !arom_l
assign (resid 19 and name hd#)    (resid 20 and name hn)     5.5  5.5  0.0    !arom_s
assign (resid 19 and name hd#)    (resid 21 and name hn)     5.5  5.5  0.0    !arom_s
assign (resid 19 and name hd#)    (resid 21 and name hd2)    3.6  3.6  0.0    !arom_m
assign (resid 19 and name hd#)    (resid 22 and name hd#)    3.6  3.6  0.0    !arom_m
assign (resid 19 and name hd#)    (resid 86 and name hg)     5.5  5.5  0.0    !arom_l
assign (resid 19 and name hd#)    (resid 91 and name hb#)    3.6  3.6  0.0    !arom_l
assign (resid 19 and name hd#)    (resid 91 and name hd#)    3.6  3.6  0.0    !arom_l
assign (resid 19 and name hd#)    (resid 91 and name he#)    5.5  5.5  0.0    !arom_l
assign (resid 19 and name he#)    (resid 21 and name hd2)    5.5  5.5  0.0    !arom_m
assign (resid 19 and name he#)    (resid 22 and name hd#)    3.6  3.6  0.0    !arom_m
assign (resid 19 and name he#)    (resid 86 and name hg)     5.5  5.5  0.0    !arom_l
assign (resid 19 and name he#)    (resid 91 and name hb#)    3.6  3.6  0.0    !arom_l
assign (resid 19 and name he#)    (resid 91 and name hd#)    5.5  5.5  0.0    !arom_l
assign (resid 31 and name hn)     (resid 34 and name hd#)    3.6  3.6  0.0    !arom_m
assign (resid 31 and name hg)     (resid 34 and name hd#)    5.5  5.5  0.0    !arom_m
assign (resid 31 and name hg)     (resid 34 and name hd#)    5.5  5.5  0.0    !arom_m
assign (resid 31 and name hd1#)   (resid 34 and name he#)    5.5  5.5  0.0    !arom_m
assign (resid 31 and name hd2#)   (resid 87 and name hd#)    2.8  2.8  0.0    !arom_l
assign (resid 32 and name hn)     (resid 34 and name hd#)    5.5  5.5  0.0    !arom_m
assign (resid 34 and name hn)     (resid 34 and name hd#)    3.6  3.6  0.0    !arom_i
assign (resid 34 and name ha)     (resid 34 and name hd#)    3.6  3.6  0.0    !arom_i
assign (resid 34 and name hd#)    (resid 35 and name hn)     3.6  3.6  0.0    !arom_s
assign (resid 34 and name hd#)    (resid 42 and name hn)     5.5  5.5  0.0    !arom_l
assign (resid 34 and name hd#)    (resid 42 and name ha)     3.6  3.6  0.0    !arom_l
assign (resid 34 and name hd#)    (resid 43 and name hn)     5.5  5.5  0.0    !arom_l
assign (resid 34 and name hd#)    (resid 43 and name hb#)    5.5  5.5  0.0    !arom_l
assign (resid 34 and name he#)    (resid 42 and name hn)     5.5  5.5  0.0    !arom_l
assign (resid 34 and name he#)    (resid 42 and name ha)     5.5  5.5  0.0    !arom_l
assign (resid 34 and name he#)    (resid 43 and name hb#)    5.5  5.5  0.0    !arom_l
assign (resid 34 and name he#)    (resid 43 and name hg#)    3.6  3.6  0.0    !arom_l
assign (resid 83 and name hn)     (resid 84 and name hd#)    3.6  3.6  0.0    !arom_s
assign (resid 86 and name hn)     (resid 91 and name hd#)    5.5  5.5  0.0    !arom_l
assign (resid 86 and name hb#)    (resid 87 and name hd#)    2.8  2.8  0.0    !arom_s
assign (resid 86 and name hb#)    (resid 87 and name he#)    3.6  3.6  0.0    !arom_s
assign (resid 86 and name hd#)    (resid 87 and name hd#)    3.6  3.6  0.0    !arom_s
assign (resid 86 and name hd#)    (resid 87 and name he#)    3.6  3.6  0.0    !arom_s
assign (resid 87 and name ha)     (resid 87 and name hd#)    2.8  2.8  0.0    !arom_i
assign (resid 87 and name hd#)    (resid 90 and name hb)     5.5  5.5  0.0    !arom_m
assign (resid 87 and name hd#)    (resid 90 and name hg2#)   5.5  5.5  0.0    !arom_m
assign (resid 87 and name hd#)    (resid 90 and name hd#)    3.6  3.6  0.0    !arom_m
assign (resid 87 and name hd#)    (resid 91 and name hb#)    3.6  3.6  0.0    !arom_m
assign (resid 87 and name hd#)    (resid 91 and name hd#)    2.8  2.8  0.0    !arom_m
assign (resid 87 and name hd#)    (resid 91 and name he#)    3.6  3.6  0.0    !arom_m
assign (resid 87 and name he#)    (resid 91 and name hd#)    5.5  5.5  0.0    !arom_m
assign (resid 87 and name he#)    (resid 91 and name he#)    5.5  5.5  0.0    !arom_m
```

TABLE B-continued

| | | | | | |
|---|---|---|---|---|---|
| assign (resid 91 and name hn) | (resid 91 and name hd#) | 3.6 | 3.6 | 0.0 | !arom_i |
| assign (resid 91 and name hd#) | (resid 92 and name hn) | 5.5 | 5.5 | 0.0 | !arom_s |
| assign (resid 2 and name hd#) | (resid 86 and name hd#) | 5.5 | 5.5 | 0.0 | !meth_l |
| assign (resid 5 and name hb#) | (resid 86 and name hd#) | 5.5 | 5.5 | 0.0 | !meth_l |
| assign (resid 17 and name hn) | (resid 90 and name hd#) | 4.1 | 4.1 | 0.0 | !meth_l |
| assign (resid 17 and name ha) | (resid 90 and name hd#) | 5.5 | 5.5 | 0.0 | !meth_l |
| assign (resid 29 and name hb#) | (resid 90 and name hd#) | 5.5 | 5.5 | 0.0 | !meth_l |
| assign (resid 29 and name hg#) | (resid 90 and name hd#) | 5.5 | 5.5 | 0.0 | !meth_l |
| assign (resid 29 and name hd#) | (resid 90 and name hd#) | 5.5 | 5.5 | 0.0 | !meth_l |
| assign (resid 29 and name he#) | (resid 90 and name hd#) | 5.5 | 5.5 | 0.0 | !meth_l |
| assign (resid 31 and name hn) | (resid 90 and name hd#) | 5.5 | 5.5 | 0.0 | !meth_l |
| assign (resid 31 and name ha) | (resid 90 and name hg2#) | 5.5 | 5.5 | 0.0 | !meth_l |
| assign (resid 31 and name ha) | (resid 90 and name hd#) | 5.5 | 5.5 | 0.0 | !meth_l |
| assign (resid 32 and name ha) | (resid 90 and name hg2#) | 5.5 | 5.5 | 0.0 | !meth_l |
| assign (resid 32 and name hb#) | (resid 90 and name hg2#) | 5.5 | 5.5 | 0.0 | !meth_l |
| assign (resid 32 and name hg) | (resid 90 and name hg2#) | 5.5 | 5.5 | 0.0 | !meth_l |
| assign (resid 40 and name hn) | (resid 40 and name he#) | 5.5 | 5.5 | 0.0 | !meth_i |
| assign (resid 47 and name ha) | (resid 48 and name hg2#) | 5.5 | 5.5 | 0.0 | !meth_s |
| assign (resid 47 and name hb1#) | (resid 74 and name hd#) | 5.5 | 5.5 | 0.0 | !meth_l |
| assign (resid 47 and name hg#) | (resid 74 and name hd#) | 5.5 | 5.5 | 0.0 | !meth_l |
| assign (resid 48 and name hn) | (resid 48 and name hg2#) | 3.6 | 3.6 | 0.0 | !meth_i |
| assign (resid 48 and name hn) | (resid 74 and name hd#) | 5.5 | 5.5 | 0.0 | !meth_l |
| assign (resid 48 and name ha) | (resid 74 and name hd#) | 3.6 | 3.6 | 0.0 | !meth_l |
| assign (resid 48 and name hg2#) | (resid 49 and name hn) | 5.5 | 5.5 | 0.0 | !meth_s |
| assign (resid 48 and name hg2#) | (resid 50 and name hn) | 3.6 | 3.6 | 0.0 | !meth_m |
| assign (resid 48 and name hg2#) | (resid 50 and name hb1#) | 5.5 | 5.5 | 0.0 | !meth_m |
| assign (resid 48 and name hg2#) | (resid 51 and name hn) | 3.1 | 3.1 | 0.0 | !meth_m |
| assign (resid 48 and name hg2#) | (resid 51 and name ha) | 3.6 | 3.6 | 0.0 | !meth_m |
| assign (resid 48 and name hg2#) | (resid 51 and name hb#) | 3.6 | 3.6 | 0.0 | !meth_m |
| assign (resid 48 and name hg2#) | (resid 51 and name hg#) | 5.5 | 5.5 | 0.0 | !meth_m |
| assign (resid 48 and name hg2#) | (resid 74 and name hd#) | 5.5 | 5.5 | 0.0 | !meth_l |
| assign (resid 49 and name hn) | (resid 74 and name hd#) | 5.5 | 5.5 | 0.0 | !meth_l |
| assign (resid 49 and name ha) | (resid 74 and name hd#) | 5.5 | 5.5 | 0.0 | !meth_l |
| assign (resid 54 and name hn) | (resid 74 and name hd#) | 5.5 | 5.5 | 0.0 | !meth_l |
| assign (resid 54 and name ha#) | (resid 74 and name hg2#) | 5.5 | 5.5 | 0.0 | !meth_l |
| assign (resid 54 and name ha#) | (resid 74 and name hd#) | 5.5 | 5.5 | 0.0 | !meth_l |
| assign (resid 56 and name hn) | (resid 60 and name hb#) | 5.5 | 5.5 | 0.0 | !meth_m |
| assign (resid 56 and name hn) | (resid 74 and name hg2#) | 5.5 | 5.5 | 0.0 | !meth_l |
| assign (resid 56 and name ha) | (resid 60 and name hb#) | 5.5 | 5.5 | 0.0 | !meth_m |
| assign (resid 56 and name ha) | (resid 90 and name hg2#) | 5.5 | 5.5 | 0.0 | !meth_l |
| assign (resid 56 and name hb1) | (resid 60 and name hb#) | 3.6 | 3.6 | 0.0 | !meth_m |
| assign (resid 57 and name hn) | (resid 60 and name hb#) | 3.6 | 3.6 | 0.0 | !meth_m |
| assign (resid 57 and name ha) | (resid 60 and name hb#) | 5.5 | 5.5 | 0.0 | !meth_m |
| assign (resid 57 and name hb#) | (resid 60 and name hb#) | 5.5 | 5.5 | 0.0 | !meth_m |
| assign (resid 58 and name hb#) | (resid 59 and name hn) | 3.6 | 3.6 | 0.0 | !meth_s |
| assign (resid 58 and name hb#) | (resid 60 and name hn) | 5.5 | 5.5 | 0.0 | !meth_m |
| assign (resid 59 and name hn) | (resid 60 and name hb#) | 5.5 | 5.5 | 0.0 | !meth_s |
| assign (resid 60 and name hb#) | (resid 61 and name hn) | 3.6 | 3.6 | 0.0 | !meth_s |
| assign (resid 60 and name hb#) | (resid 76 and name ha) | 5.5 | 5.5 | 0.0 | !meth_l |
| assign (resid 60 and name hb#) | (resid 76 and name hb1) | 5.5 | 5.5 | 0.0 | !meth_l |
| assign (resid 60 and name hb#) | (resid 77 and name hn) | 3.6 | 3.6 | 0.0 | !meth_l |
| assign (resid 60 and name hb#) | (resid 77 and name ha) | 5.5 | 5.5 | 0.0 | !meth_l |
| assign (resid 60 and name hb#) | (resid 78 and name hn) | 5.5 | 5.5 | 0.0 | !meth_l |
| assign (resid 60 and name hb#) | (resid 78 and name hb1) | 5.5 | 5.5 | 0.0 | !meth_l |
| assign (resid 62 and name ha) | (resid 74 and name hg2#) | 5.5 | 5.5 | 0.0 | !meth_l |
| assign (resid 63 and name hn) | (resid 74 and name hg2#) | 4.1 | 4.1 | 0.0 | !meth_l |
| assign (resid 63 and name hn) | (resid 74 and name hd#) | 3.6 | 3.6 | 0.0 | !meth_l |
| assign (resid 63 and name hg2#) | (resid 64 and name hn) | 3.6 | 3.6 | 0.0 | !meth_s |
| assign (resid 64 and name ha) | (resid 74 and name hg2#) | 5.5 | 5.5 | 0.0 | !meth_l |
| assign (resid 64 and name ha) | (resid 74 and name hd#) | 5.5 | 5.5 | 0.0 | !meth_l |
| assign (resid 64 and name hb#) | (resid 74 and name hd#) | 5.5 | 5.5 | 0.0 | !meth_l |
| assign (resid 64 and name hg#) | (resid 74 and name hd#) | 5.5 | 5.5 | 0.0 | !meth_l |
| assign (resid 72 and name hn) | (resid 72 and name he#) | 3.6 | 3.6 | 0.0 | !meth_i |
| assign (resid 72 and name hb#) | (resid 74 and name hd#) | 5.5 | 5.5 | 0.0 | !meth_m |
| assign (resid 73 and name hn) | (resid 74 and name hd#) | 5.5 | 5.5 | 0.0 | !meth_s |
| assign (resid 74 and name hn) | (resid 74 and name hg2#) | 3.6 | 3.6 | 0.0 | !meth_i |
| assign (resid 74 and name ha) | (resid 74 and name hg2#) | 3.6 | 3.6 | 0.0 | !meth_i |
| assign (resid 74 and name ha) | (resid 74 and name hd#) | 3.6 | 3.6 | 0.0 | !meth_i |
| assign (resid 74 and name hg2#) | (resid 75 and name ha) | 5.5 | 5.5 | 0.0 | !meth_s |
| assign (resid 75 and name hg2#) | (resid 76 and name hn) | 3.6 | 3.6 | 0.0 | !meth_s |
| assign (resid 79 and name hn) | (resid 79 and name hg2#) | 3.6 | 3.6 | 0.0 | !meth_i |
| assign (resid 79 and name hg2#) | (resid 80 and name hn) | 3.6 | 3.6 | 0.0 | !meth_s |
| assign (resid 85 and name ha) | (resid 86 and name hd#) | 5.5 | 5.5 | 0.0 | !meth_s |
| assign (resid 86 and name hd#) | (resid 87 and name hn) | 5.5 | 5.5 | 0.0 | !meth_s |
| assign (resid 86 and name hd#) | (resid 91 and name hb#) | 5.5 | 5.5 | 0.0 | !meth_l |
| assign (resid 86 and name hd#) | (resid 92 and name ha) | 5.5 | 5.5 | 0.0 | !meth_l |
| assign (resid 87 and name ha) | (resid 90 and name hd#) | 5.5 | 5.5 | 0.0 | !meth_m |
| assign (resid 87 and name hb#) | (resid 90 and name hg2#) | 5.5 | 5.5 | 0.0 | !meth_m |
| assign (resid 87 and name hb#) | (resid 90 and name hd#) | 5.5 | 5.5 | 0.0 | !meth_m |

TABLE B-continued

| | | | | |
|---|---|---|---|---|
| assign (resid 89 and name hn) | (resid 90 and name hg2#) | 5.5 | 5.5 | 0.0 | !meth_s |
| assign (resid 90 and name hn) | (resid 90 and name hg2#) | 3.6 | 3.6 | 0.0 | !meth_i |
| assign (resid 90 and name ha) | (resid 90 and name hg2#) | 3.6 | 3.6 | 0.0 | !meth_i |
| assign (resid 90 and name hg2#) | (resid 91 and name hn) | 5.5 | 5.5 | 0.0 | !meth_s |
| assign (resid 90 and name hd#) | (resid 91 and name hn) | 5.5 | 5.5 | 0.0 | !meth_s |
| assign (resid 6 and name ha) | (resid 6 and name hg#) | 2.8 | 2.8 | 0.0 | !dgnm_i |
| assign (resid 10 and name he#) | (resid 19 and name hn) | 3.6 | 3.6 | 0.0 | !dgnm_l |
| assign (resid 10 and name he#) | (resid 28 and name hn) | 3.6 | 3.6 | 0.0 | !dgnm_l |
| assign (resid 14 and name hn) | (resid 14 and name hg#) | 3.6 | 3.6 | 0.0 | !dgnm_i |
| assign (resid 14 and name hb#) | (resid 15 and name hn) | 4.1 | 4.1 | 0.0 | !dgnm_s |
| assign (resid 24 and name hn) | (resid 24 and name hg#) | 3.6 | 3.6 | 0.0 | !dgnm_i |
| assign (resid 24 and name ha) | (resid 24 and name hg#) | 2.8 | 2.8 | 0.0 | !dgnm_i |
| assign (resid 24 and name hg#) | (resid 25 and name hn) | 5.5 | 5.5 | 0.0 | !dgnm_s |
| assign (resid 25 and name hn) | (resid 25 and name hd#) | 5.5 | 5.5 | 0.0 | !dgnm_i |
| assign (resid 26 and name hn) | (resid 26 and name hb#) | 2.8 | 2.8 | 0.0 | !dgnm_i |
| assign (resid 29 and name hn) | (resid 29 and name hd#) | 3.6 | 3.6 | 0.0 | !dgnm_i |
| assign (resid 29 and name hb#) | (resid 30 and name hn) | 3.6 | 3.6 | 0.0 | !dgnm_s |
| assign (resid 33 and name hn) | (resid 47 and name hg#) | 5.5 | 5.5 | 0.0 | !dgnm_l |
| assign (resid 35 and name hn) | (resid 35 and name hg#) | 3.6 | 3.6 | 0.0 | !dgnm_i |
| assign (resid 35 and name ha) | (resid 35 and name hd#) | 3.6 | 3.6 | 0.0 | !dgnm_i |
| assign (resid 35 and name hg#) | (resid 36 and name hn) | 3.6 | 3.6 | 0.0 | !dgnm_s |
| assign (resid 35 and name hg#) | (resid 42 and name hn) | 5.5 | 5.5 | 0.0 | !dgnm_l |
| assign (resid 35 and name hg#) | (resid 44 and name ha) | 3.6 | 3.6 | 0.0 | !dgnm_l |
| assign (resid 35 and name hg#) | (resid 44 and name hb#) | 3.6 | 3.6 | 0.0 | !dgnm_l |
| assign (resid 36 and name hn) | (resid 36 and name hg#) | 3.6 | 3.6 | 0.0 | !dgnm_i |
| assign (resid 36 and name ha) | (resid 36 and name hg#) | 2.8 | 2.8 | 0.0 | !dgnm_i |
| assign (resid 36 and name hb#) | (resid 37 and name hn) | 5.5 | 5.5 | 0.0 | !dgnm_s |
| assign (resid 36 and name hg#) | (resid 37 and name hn) | 3.6 | 3.6 | 0.0 | !dgnm_s |
| assign (resid 36 and name hg#) | (resid 40 and name hn) | 5.5 | 5.5 | 0.0 | !dgnm_m |
| assign (resid 37 and name ha) | (resid 37 and name hg#) | 3.6 | 3.6 | 0.0 | !dgnm_i |
| assign (resid 37 and name hg#) | (resid 38 and name hn) | 4.1 | 4.1 | 0.0 | !dgnm_s |
| assign (resid 40 and name hn) | (resid 40 and name hg#) | 3.6 | 3.6 | 0.0 | !dgnm_i |
| assign (resid 40 and name hn) | (resid 40 and name hd#) | 5.5 | 5.5 | 0.0 | !dgnm_i |
| assign (resid 44 and name ha) | (resid 45 and name hg#) | 3.6 | 3.6 | 0.0 | !dgnm_s |
| assign (resid 45 and name hg#) | (resid 46 and name hn) | 3.6 | 3.6 | 0.0 | !dgnm_s |
| assign (resid 47 and name hg#) | (resid 48 and name hn) | 5.5 | 5.5 | 0.0 | !dgnm_s |
| assign (resid 49 and name hn) | (resid 51 and name hg#) | 3.6 | 3.6 | 0.0 | !dgnm_m |
| assign (resid 49 and name hn) | (resid 64 and name hb#) | 5.5 | 5.5 | 0.0 | !dgnm_l |
| assign (resid 49 and name hn) | (resid 64 and name hg#) | 5.5 | 5.5 | 0.0 | !dgnm_l |
| assign (resid 51 and name hn) | (resid 51 and name hg#) | 3.6 | 3.6 | 0.0 | !dgnm_i |
| assign (resid 51 and name hg#) | (resid 52 and name hd22) | 5.5 | 5.5 | 0.0 | !dgnm_s |
| assign (resid 61 and name hn) | (resid 61 and name hb#) | 2.8 | 2.8 | 0.0 | !dgnm_i |
| assign (resid 61 and name hb#) | (resid 62 and name hn) | 3.6 | 3.6 | 0.0 | !dgnm_s |
| assign (resid 64 and name hn) | (resid 64 and name hb#) | 2.8 | 2.8 | 0.0 | !dgnm_i |
| assign (resid 64 and name hn) | (resid 64 and name hg#) | 2.8 | 2.8 | 0.0 | !dgnm_i |
| assign (resid 64 and name hn) | (resid 65 and name hg#) | 2.8 | 2.8 | 0.0 | !dgnm_s |
| assign (resid 64 and name ha) | (resid 64 and name hg#) | 3.6 | 3.6 | 0.0 | !dgnm_i |
| assign (resid 64 and name hb#) | (resid 74 and name ha) | 3.6 | 3.6 | 0.0 | !dgnm_l |
| assign (resid 65 and name hn) | (resid 65 and name hg#) | 3.6 | 3.6 | 0.0 | !dgnm_i |
| assign (resid 69 and name hb#) | (resid 70 and name hn) | 2.8 | 2.8 | 0.0 | !dgnm_s |
| assign (resid 71 and name ha#) | (resid 72 and name hn) | 2.6 | 2.6 | 0.0 | !dgnm_s |
| assign (resid 72 and name hn) | (resid 72 and name hd#) | 3.6 | 3.6 | 0.0 | !dgnm_i |
| assign (resid 73 and name hn) | (resid 73 and name hb#) | 2.8 | 2.8 | 0.0 | !dgnm_i |
| assign (resid 73 and name hb#) | (resid 74 and name hn) | 3.6 | 3.6 | 0.0 | !dgnm_s |
| assign (resid 80 and name hn) | (resid 80 and name hb#) | 2.8 | 2.8 | 0.0 | !dgnm_i |
| assign (resid 80 and name hb#) | (resid 81 and name hd#) | 2.8 | 2.8 | 0.0 | !dgnm_s |
| assign (resid 80 and name hb#) | (resid 83 and name hn) | 3.6 | 3.6 | 0.0 | !dgnm_m |
| assign (resid 80 and name hb#) | (resid 83 and name hn) | 2.8 | 2.8 | 0.0 | !dgnm_m |
| assign (resid 84 and name ha) | (resid 85 and name hg#) | 3.6 | 3.6 | 0.0 | !dgnm_s |
| assign (resid 84 and name ha) | (resid 85 and name hd#) | 2.8 | 2.8 | 0.0 | !dgnm_s |
| assign (resid 85 and name hg#) | (resid 89 and name hn) | 5.5 | 5.5 | 0.0 | !dgnm_m |
| assign (resid 86 and name hb#) | (resid 87 and name hn) | 3.6 | 3.6 | 0.0 | !dgnm_s |
| assign (resid 86 and name hb#) | (resid 91 and name hb#) | 3.6 | 3.6 | 0.0 | !dgnm_l |
| class nsam | | | | | |
| assign (resid 8 and name ha) | (resid 8 and name hg#) | 3.6 | 3.6 | 0.0 | !meth_i |
| assign (resid 8 and name hg#) | (resid 20 and name hd#) | 5.5 | 5.5 | 0.0 | !meth_l |
| assign (resid 8 and name hg#) | (resid 20 and name he) | 5.5 | 5.5 | 0.0 | !meth_l |
| assign (resid 15 and name ha) | (resid 31 and name hd1#) | 3.6 | 3.6 | 0.0 | !meth_l |
| assign (resid 15 and name hb#) | (resid 31 and name hd1#) | 5.5 | 5.5 | 0.0 | !meth_l |
| assign (resid 16 and name hn) | (resid 31 and name hd1#) | 5.5 | 5.5 | 0.0 | !meth_l |
| assign (resid 16 and name ha) | (resid 31 and name hd#) | 5.5 | 5.5 | 0.0 | !meth_l |
| assign (resid 17 and name hn) | (resid 31 and name hd2#) | 4.1 | 4.1 | 0.0 | !meth_l |
| assign (resid 17 and name ha#) | (resid 31 and name hd2#) | 5.5 | 5.5 | 0.0 | !meth_l |
| assign (resid 19 and name hz) | (resid 22 and name hd#) | 3.6 | 3.6 | 0.0 | !meth_m |
| assign (resid 22 and name hd#) | (resid 23 and name hn) | 5.5 | 5.5 | 0.0 | !meth_s |
| assign (resid 30 and name ha) | (resid 31 and name hd#) | 5.5 | 5.5 | 0.0 | !meth_s |
| assign (resid 31 and name ha) | (resid 31 and name hd2#) | 3.6 | 3.6 | 0.0 | !meth_i |
| assign (resid 31 and name hd2#) | (resid 87 and name hb#) | 5.5 | 5.5 | 0.0 | !meth_l |
| assign (resid 31 and name hd2#) | (resid 87 and name hz) | 3.6 | 3.6 | 0.0 | !meth_l |

TABLE B-continued

| | | | | | |
|---|---|---|---|---|---|
| assign (resid 31 and name hd2#) | (resid 90 and name hg2#) | 5.5 | 5.5 | 0.0 | !meth_l |
| assign (resid 31 and name hd2#) | (resid 90 and name hd#) | 5.5 | 5.5 | 0.0 | !meth_l |
| assign (resid 32 and name ha) | (resid 32 and name hd2#) | 3.6 | 3.6 | 0.0 | !meth_i |
| assign (resid 32 and name hd2#) | (resid 33 and name hn) | 3.6 | 3.6 | 0.0 | !meth_s |
| assign (resid 32 and name hd2#) | (resid 55 and name ha#) | 5.5 | 5.5 | 0.0 | !meth_l |
| assign (resid 32 and name hd2#) | (resid 56 and name hn) | 5.5 | 5.5 | 0.0 | !meth_l |
| assign (resid 32 and name hd2#) | (resid 56 and name ha) | 5.5 | 5.5 | 0.0 | !meth_l |
| assign (resid 32 and name hd2#) | (resid 74 and name hb) | 5.5 | 5.5 | 0.0 | !meth_l |
| assign (resid 32 and name hd2#) | (resid 74 and name hg2#) | 5.5 | 5.5 | 0.0 | !meth_l |
| assign (resid 32 and name hd2#) | (resid 90 and name ha) | 5.5 | 5.5 | 0.0 | !meth_l |
| assign (resid 32 and name hd2#) | (resid 90 and name hg2#) | 3.6 | 3.6 | 0.0 | !meth_l |
| assign (resid 32 and name hd1#) | (resid 88 and name hb#) | 5.5 | 5.5 | 0.0 | !meth_l |
| assign (resid 35 and name hn) | (resid 42 and name hg2#) | 5.5 | 5.5 | 0.0 | !meth_l |
| assign (resid 35 and name hb2) | (resid 42 and name hg1#) | 5.5 | 5.5 | 0.0 | !meth_l |
| assign (resid 35 and name hg#) | (resid 42 and name hg2#) | 5.5 | 5.5 | 0.0 | !meth_l |
| assign (resid 37 and name hn) | (resid 42 and name hg1#) | 5.5 | 5.5 | 0.0 | !meth_l |
| assign (resid 37 and name hn) | (resid 42 and name hg2#) | 5.5 | 5.5 | 0.0 | !meth_l |
| assign (resid 37 and name ha) | (resid 42 and name hg2#) | 5.5 | 5.5 | 0.0 | !meth_l |
| assign (resid 37 and name hb#) | (resid 42 and name hg1#) | 5.5 | 5.5 | 0.0 | !meth_l |
| assign (resid 37 and name hb#) | (resid 42 and name hg2#) | 5.5 | 5.5 | 0.0 | !meth_l |
| assign (resid 37 and name hg#) | (resid 42 and name hg1#) | 5.5 | 5.5 | 0.0 | !meth_l |
| assign (resid 37 and name hg#) | (resid 42 and name hg2#) | 5.5 | 5.5 | 0.0 | !meth_l |
| assign (resid 40 and name hn) | (resid 42 and name hg1#) | 5.5 | 5.5 | 0.0 | !meth_m |
| assign (resid 40 and name hg#) | (resid 42 and name hg1#) | 5.5 | 5.5 | 0.0 | !meth_m |
| assign (resid 41 and name ha) | (resid 42 and name hg1#) | 5.5 | 5.5 | 0.0 | !meth_s |
| assign (resid 41 and name ha) | (resid 42 and name hg2#) | 5.5 | 5.5 | 0.0 | !meth_s |
| assign (resid 41 and name hb#) | (resid 42 and name hg#) | 5.5 | 5.5 | 0.0 | !meth_s |
| assign (resid 42 and name hg1#) | (resid 43 and name hn) | 3.6 | 3.6 | 0.0 | !meth_s |
| assign (resid 42 and name hg2#) | (resid 43 and name hn) | 3.6 | 3.6 | 0.0 | !meth_s |
| assign (resid 5 and name ha) | (resid 20 and name hb#) | 3.6 | 3.6 | 0.0 | !nsam_l |
| assign (resid 7 and name ha) | (resid 20 and name hb#) | 3.6 | 3.6 | 0.0 | !nsam_l |
| assign (resid 7 and name ha) | (resid 20 and name hd#) | 3.6 | 3.6 | 0.0 | !nsam_l |
| assign (resid 10 and name ha) | (resid 10 and name hg#) | 3.6 | 3.6 | 0.0 | !nsam_i |
| assign (resid 12 and name ha) | (resid 13 and name hd#) | 2.8 | 2.8 | 0.0 | !nsam_s |
| assign (resid 12 and name hb#) | (resid 13 and name hd#) | 3.6 | 3.6 | 0.0 | !nsam_s |
| assign (resid 12 and name hb#) | (resid 28 and name hb#) | 3.6 | 3.6 | 0.0 | !nsam_l |
| assign (resid 13 and name hb2) | (resid 14 and name hn) | 3.6 | 3.6 | 0.0 | !sing_s |
| assign (resid 13 and name hg#) | (resid 16 and name hb#) | 3.6 | 3.6 | 0.0 | !nsam_m |
| assign (resid 13 and name hd4#) | (resid 28 and name hb#) | 3.6 | 3.6 | 0.0 | !nsam_l |
| assign (resid 15 and name hb2) | (resid 41 and name hb2) | 3.6 | 3.6 | 0.0 | !sing_l |
| assign (resid 16 and name ha) | (resid 30 and name hb#) | 3.6 | 3.6 | 0.0 | !nsam_l |
| assign (resid 16 and name hb1#) | (resid 30 and name ha) | 3.6 | 3.6 | 0.0 | !nsam_l |
| assign (resid 16 and name hb#) | (resid 31 and name hn) | 3.6 | 3.6 | 0.0 | !nsam_l |
| assign (resid 17 and name ha#) | (resid 87 and name hz) | 3.6 | 3.6 | 0.0 | !nsam_l |
| assign (resid 20 and name ha) | (resid 20 and name hg#) | 3.6 | 3.6 | 0.0 | !nsam_i |
| assign (resid 20 and name ha) | (resid 26 and name hg#) | 3.6 | 3.6 | 0.0 | !nsam_l |
| assign (resid 20 and name hb#) | (resid 20 and name hd#) | 3.6 | 3.6 | 0.0 | !nsam_i |
| assign (resid 20 and name hg#) | (resid 21 and name hn) | 3.6 | 3.6 | 0.0 | !nsam_s |
| assign (resid 20 and name hg#) | (resid 24 and name ha) | 3.6 | 3.6 | 0.0 | !nsam_m |
| assign (resid 21 and name hb#) | (resid 22 and name hn) | 5.5 | 5.5 | 0.0 | !nsam_s |
| assign (resid 21 and name hb#) | (resid 23 and name hn) | 5.5 | 5.5 | 0.0 | !nsam_m |
| assign (resid 22 and name hb2) | (resid 23 and name hn) | 3.6 | 3.6 | 0.0 | !sing_s |
| assign (resid 24 and name hb#) | (resid 25 and name hn) | 5.5 | 5.5 | 0.0 | !nsam_s |
| assign (resid 25 and name hn) | (resid 25 and name hg#) | 3.6 | 3.6 | 0.0 | !nsam_i |
| assign (resid 25 and name hn) | (resid 26 and name hn) | 3.6 | 3.6 | 0.0 | !nsam_s |
| assign (resid 26 and name hn) | (resid 26 and name hg#) | 3.6 | 3.6 | 0.0 | !nsam_i |
| assign (resid 26 and name ha) | (resid 26 and name hg#) | 3.6 | 3.6 | 0.0 | !nsam_i |
| assign (resid 27 and name ha) | (resid 27 and name hg#) | 2.8 | 2.8 | 0.0 | !nsam_i |
| assign (resid 27 and name hb#) | (resid 28 and name hn) | 2.8 | 2.8 | 0.0 | !nsam_s |
| assign (resid 27 and name hg#) | (resid 28 and name hn) | 2.8 | 2.8 | 0.0 | !nsam_s |
| assign (resid 28 and name hn) | (resid 28 and name hb#) | 2.8 | 2.8 | 0.0 | !nsam_i |
| assign (resid 29 and name hg#) | (resid 30 and name hn) | 2.8 | 2.8 | 0.0 | !nsam_s |
| assign (resid 29 and name hd#) | (resid 90 and name hb) | 3.6 | 3.6 | 0.0 | !nsam_l |
| assign (resid 30 and name hn) | (resid 30 and name hb#) | 2.8 | 2.8 | 0.0 | !nsam_i |
| assign (resid 30 and name hb1) | (resid 31 and name hn) | 3.6 | 3.6 | 0.0 | !sing_s |
| assign (resid 30 and name hb#) | (resid 34 and name hn) | 5.5 | 5.5 | 0.0 | !nsam_m |
| assign (resid 30 and name hb2) | (resid 34 and name hb2) | 3.6 | 3.6 | 0.0 | !sing_m |
| assign (resid 30 and name hb#) | (resid 35 and name ha) | 3.6 | 3.6 | 0.0 | !nsam_l |
| assign (resid 31 and name hn) | (resid 31 and name hb#) | 3.6 | 3.6 | 0.0 | !nsam_i |
| assign (resid 31 and name hn) | (resid 34 and name hb2) | 3.6 | 3.6 | 0.0 | !sing_m |
| assign (resid 32 and name hb1) | (resid 33 and name hn) | 3.6 | 3.6 | 0.0 | !sing_s |
| assign (resid 33 and name ha) | (resid 44 and name hb#) | 3.6 | 3.6 | 0.0 | !nsam_l |
| assign (resid 33 and name ha) | (resid 47 and name hb1) | 3.6 | 3.6 | 0.0 | !sing_l |
| assign (resid 33 and name hb2) | (resid 34 and name hn) | 5.5 | 5.5 | 0.0 | !sing_s |
| assign (resid 34 and name ha) | (resid 44 and name hb#) | 3.6 | 3.6 | 0.0 | !nsam_l |
| assign (resid 34 and name hb1) | (resid 35 and name hn) | 4.1 | 4.1 | 0.0 | !sing_s |
| assign (resid 35 and name hb#) | (resid 35 and name hd#) | 2.8 | 2.8 | 0.0 | !nsam_i |
| assign (resid 35 and name hb2) | (resid 36 and name hn) | 3.6 | 3.6 | 0.0 | !sing_s |
| assign (resid 35 and name hb#) | (resid 44 and name hb#) | 3.6 | 3.6 | 0.0 | !nsam_l |

TABLE B-continued

| | | | | | |
|---|---|---|---|---|---|
| assign (resid 35 and name hd#) | (resid 44 and name ha) | 3.6 | 3.6 | 0.0 | !nsam_l |
| assign (resid 37 and name hn) | (resid 40 and name hb#) | 5.5 | 5.5 | 0.0 | !nsam_m |
| assign (resid 38 and name ha#) | (resid 39 and name hn) | 3.1 | 3.1 | 0.0 | !nsam_s |
| assign (resid 38 and name ha#) | (resid 40 and name hn) | 5.5 | 5.5 | 0.0 | !nsam_m |
| assign (resid 39 and name hb#) | (resid 40 and name hn) | 3.6 | 3.6 | 0.0 | !nsam_s |
| assign (resid 41 and name hb1) | (resid 42 and name hn) | 3.6 | 3.6 | 0.0 | !sing_s |
| assign (resid 43 and name hn) | (resid 43 and name hb#) | 2.8 | 2.8 | 0.0 | !nsam_i |
| assign (resid 43 and name ha) | (resid 43 and name hg#) | 2.8 | 2.8 | 0.0 | !nsam_i |
| assign (resid 43 and name hb#) | (resid 44 and name hn) | 3.6 | 3.6 | 0.0 | !nsam_s |
| assign (resid 43 and name hg#) | (resid 44 and name hn) | 3.6 | 3.6 | 0.0 | !nsam_s |
| assign (resid 44 and name hn) | (resid 45 and name hd#) | 5.5 | 5.5 | 0.0 | !nsam_s |
| assign (resid 44 and name ha) | (resid 45 and name hd#) | 2.8 | 2.8 | 0.0 | !nsam_s |
| assign (resid 45 and name hb2) | (resid 46 and name hn) | 3.6 | 3.6 | 0.0 | !sing_s |
| assign (resid 46 and name hn) | (resid 46 and name hb#) | 3.6 | 3.6 | 0.0 | !nsam_i |
| assign (resid 46 and name hn) | (resid 47 and name hd#) | 3.6 | 3.6 | 0.0 | !nsam_s |
| assign (resid 46 and name ha) | (resid 47 and name hd#) | 3.6 | 3.6 | 0.0 | !nsam_s |
| assign (resid 47 and name hb2) | (resid 48 and name hn) | 4.1 | 4.1 | 0.0 | !sing_s |
| assign (resid 47 and name hb2) | (resid 74 and name hg1#) | 3.6 | 3.6 | 0.0 | !nsam_l |
| assign (resid 47 and name hg#) | (resid 74 and name hg1#) | 3.6 | 3.6 | 0.0 | !nsam_l |
| assign (resid 48 and name hn) | (resid 54 and name ha#) | 4.1 | 4.1 | 0.0 | !nsam_l |
| assign (resid 48 and name hn) | (resid 74 and name hg1#) | 5.5 | 5.5 | 0.0 | !nsam_l |
| assign (resid 49 and name ha) | (resid 54 and name ha#) | 3.6 | 3.6 | 0.0 | !nsam_l |
| assign (resid 49 and name ha) | (resid 62 and name hb1) | 5.5 | 5.5 | 0.0 | !sing_l |
| assign (resid 50 and name hb1) | (resid 51 and name hn) | 3.6 | 3.6 | 0.0 | !sing_s |
| assign (resid 53 and name hb#) | (resid 56 and name hn) | 5.5 | 5.5 | 0.0 | !nsam_m |
| assign (resid 53 and name hb1) | (resid 58 and name ha) | 3.6 | 3.6 | 0.0 | !sing_l |
| assign (resid 53 and name hd22) | (resid 56 and name hn) | 5.5 | 5.5 | 0.0 | !sing_m |
| assign (resid 53 and name hd21) | (resid 60 and name hn) | 5.5 | 5.5 | 0.0 | !sing_l |
| assign (resid 54 and name ha#) | (resid 55 and name hn) | 3.6 | 3.6 | 0.0 | !nsam_s |
| assign (resid 54 and name ha#) | (resid 56 and name hn) | 3.6 | 3.6 | 0.0 | !nsam_m |
| assign (resid 55 and name ha#) | (resid 56 and name hn) | 3.6 | 3.6 | 0.0 | !nsam_s |
| assign (resid 56 and name hb1) | (resid 57 and name hn) | 4.1 | 4.1 | 0.0 | !sing_s |
| assign (resid 56 and name hb2) | (resid 62 and name hn) | 5.5 | 5.5 | 0.0 | !sing_l |
| assign (resid 56 and name hb2) | (resid 62 and name ha) | 3.6 | 3.6 | 0.0 | !sing_l |
| assign (resid 57 and name hb#) | (resid 58 and name hn) | 3.6 | 3.6 | 0.0 | !nsam_s |
| assign (resid 57 and name hb#) | (resid 59 and name hn) | 4.1 | 4.1 | 0.0 | !nsam_m |
| assign (resid 57 and name hb#) | (resid 60 and name hn) | 4.1 | 4.1 | 0.0 | !nsam_m |
| assign (resid 57 and name hb#) | (resid 91 and name ha) | 2.8 | 2.8 | 0.0 | !nsam_l |
| assign (resid 57 and name hb#) | (resid 92 and name hn) | 5.5 | 5.5 | 0.0 | !nsam_l |
| assign (resid 58 and name hn) | (resid 59 and name hb#) | 5.5 | 5.5 | 0.0 | !nsam_s |
| assign (resid 59 and name hb#) | (resid 80 and name hg#) | 3.6 | 3.6 | 0.0 | !nsam_l |
| assign (resid 59 and name hb#) | (resid 60 and name hn) | 3.6 | 3.6 | 0.0 | !nsam_s |
| assign (resid 60 and name ha) | (resid 78 and name hb#) | 3.6 | 3.6 | 0.0 | !nsam_l |
| assign (resid 61 and name hn) | (resid 61 and name hg#) | 3.6 | 3.6 | 0.0 | !nsam_i |
| assign (resid 65 and name hn) | (resid 65 and name hb#) | 2.8 | 2.8 | 0.0 | !nsam_i |
| assign (resid 66 and name hn) | (resid 66 and name hb#) | 2.8 | 2.8 | 0.0 | !nsam_i |
| assign (resid 66 and name hb#) | (resid 67 and name hn) | 3.6 | 3.6 | 0.0 | !nsam_s |
| assign (resid 67 and name hb#) | (resid 73 and name hb#) | 3.6 | 3.6 | 0.0 | !nsam_l |
| assign (resid 68 and name ha#) | (resid 69 and name hn) | 3.6 | 3.6 | 0.0 | !nsam_s |
| assign (resid 72 and name hn) | (resid 72 and name hg#) | 3.6 | 3.6 | 0.0 | !nsam_i |
| assign (resid 74 and name hn) | (resid 74 and name hg1#) | 3.6 | 3.6 | 0.0 | !nsam_i |
| assign (resid 74 and name ha) | (resid 74 and name hg1#) | 3.6 | 3.6 | 0.0 | !nsam_i |
| assign (resid 76 and name hn) | (resid 76 and name hb#) | 2.8 | 2.8 | 0.0 | !nsam_i |
| assign (resid 76 and name hb1) | (resid 77 and name hn) | 5.5 | 5.5 | 0.0 | !sing_s |
| assign (resid 76 and name hb1) | (resid 89 and name ha#) | 3.6 | 3.6 | 0.0 | !nsam_l |
| assign (resid 78 and name hb1) | (resid 79 and name hn) | 5.5 | 5.5 | 0.0 | !sing_s |
| assign (resid 78 and name hb#) | (resid 92 and name hb#) | 3.6 | 3.6 | 0.0 | !nsam_l |
| assign (resid 78 and name hb#) | (resid 80 and name hn) | 5.5 | 5.5 | 0.0 | !nsam_m |
| assign (resid 78 and name hb#) | (resid 83 and name hb#) | 3.6 | 3.6 | 0.0 | !nsam_l |
| assign (resid 80 and name hn) | (resid 80 and name hg#) | 3.6 | 3.6 | 0.0 | !nsam_i |
| assign (resid 80 and name hn) | (resid 81 and name hd#) | 5.5 | 5.5 | 0.0 | !nsam_s |
| assign (resid 80 and name hn) | (resid 83 and name hb#) | 3.6 | 3.6 | 0.0 | !nsam_m |
| assign (resid 80 and name ha) | (resid 80 and name hg#) | 3.6 | 3.6 | 0.0 | !nsam_i |
| assign (resid 80 and name ha) | (resid 81 and name hd#) | 2.8 | 2.8 | 0.0 | !nsam_s |
| assign (resid 80 and name hg#) | (resid 81 and name hd#) | 3.6 | 3.6 | 0.0 | !nsam_s |
| assign (resid 81 and name hb2) | (resid 82 and name hn) | 3.6 | 3.6 | 0.0 | !sing_s |
| assign (resid 81 and name hd#) | (resid 82 and name hn) | 5.5 | 5.5 | 0.0 | !nsam_s |
| assign (resid 82 and name hb#) | (resid 83 and name hn) | 3.6 | 3.6 | 0.0 | !nsam_s |
| assign (resid 85 and name ha) | (resid 89 and name ha#) | 3.6 | 3.6 | 0.0 | !nsam_m |
| assign (resid 85 and name hb#) | (resid 88 and name ha) | 3.6 | 3.6 | 0.0 | !nsam_m |
| assign (resid 85 and name hb#) | (resid 89 and name hn) | 3.6 | 3.6 | 0.0 | !nsam_m |
| assign (resid 85 and name hb#) | (resid 86 and name hn) | 3.6 | 3.6 | 0.0 | !nsam_s |
| assign (resid 86 and name hn) | (resid 89 and name ha#) | 5.5 | 5.5 | 0.0 | !nsam_m |
| assign (resid 87 and name hb#) | (resid 90 and name hn) | 3.6 | 3.6 | 0.0 | !nsam_m |
| assign (resid 87 and name hb#) | (resid 90 and name hg1#) | 5.5 | 5.5 | 0.0 | !nsam_m |
| assign (resid 89 and name ha#) | (resid 90 and name hn) | 3.6 | 3.6 | 0.0 | !nsam_s |
| assign (resid 90 and name hg1#) | (resid 91 and name hn) | 4.1 | 4.1 | 0.0 | !nsam_s |
| class sing | | | | | |
| assign (resid 2 and name hn) | (resid 3 and name hn) | 5.5 | 5.5 | 0.0 | !sing_s |

TABLE B-continued

| | | | | | |
|---|---|---|---|---|---|
| assign (resid 4 and name hn) | (resid 5 and name hn) | 5.5 | 5.5 | 0.0 | !sing_s |
| assign (resid 5 and name hn) | (resid 6 and name hn) | 3.6 | 3.6 | 0.0 | !sing_s |
| assign (resid 5 and name ha) | (resid 20 and name hn) | 5.5 | 5.5 | 0.0 | !sing_l |
| assign (resid 6 and name hn) | (resid 7 and name hn) | 5.5 | 5.5 | 0.0 | !sing_s |
| assign (resid 7 and name hn) | (resid 8 and name hn) | 5.5 | 5.5 | 0.0 | !sing_s |
| assign (resid 8 and name hn) | (resid 9 and name hn) | 5.5 | 5.5 | 0.0 | !sing_s |
| assign (resid 9 and name hn) | (resid 10 and name hn) | 3.6 | 3.6 | 0.0 | !sing_s |
| assign (resid 13 and name ha) | (resid 14 and name hn) | 2.6 | 2.6 | 0.0 | !sing_s |
| assign (resid 14 and name hn) | (resid 15 and name hn) | 5.5 | 5.5 | 0.0 | !sing_s |
| assign (resid 14 and name ha) | (resid 15 and name hn) | 2.6 | 2.6 | 0.0 | !sing_m |
| assign (resid 15 and name hn) | (resid 16 and name hn) | 3.6 | 3.6 | 0.0 | !sing_s |
| assign (resid 15 and name ha) | (resid 16 and name hn) | 3.6 | 3.6 | 0.0 | !sing_s |
| assign (resid 15 and name ha) | (resid 31 and name hg) | 3.6 | 3.6 | 0.0 | !sing_l |
| assign (resid 16 and name hn) | (resid 17 and name hn) | 5.5 | 5.5 | 0.0 | !sing_s |
| assign (resid 16 and name hn) | (resid 31 and name hn) | 5.5 | 5.5 | 0.0 | !sing_l |
| assign (resid 16 and name hn) | (resid 31 and name hg) | 5.5 | 5.5 | 0.0 | !sing_l |
| assign (resid 16 and name ha) | (resid 30 and name ha) | 2.8 | 2.8 | 0.0 | !sing_l |
| assign (resid 16 and name ha) | (resid 31 and name hn) | 3.6 | 3.6 | 0.0 | !sing_l |
| assign (resid 16 and name ha) | (resid 31 and name hg) | 3.6 | 3.6 | 0.0 | !sing_l |
| assign (resid 17 and name hn) | (resid 31 and name hn) | 5.5 | 5.5 | 0.0 | !sing_l |
| assign (resid 18 and name ha) | (resid 19 and name hn) | 2.6 | 2.6 | 0.0 | !sing_s |
| assign (resid 18 and name ha) | (resid 28 and name ha) | 2.8 | 2.8 | 0.0 | !sing_l |
| assign (resid 19 and name hn) | (resid 20 and name hn) | 5.5 | 5.5 | 0.0 | !sing_s |
| assign (resid 19 and name hn) | (resid 21 and name hd2) | 5.5 | 5.5 | 0.0 | !sing_m |
| assign (resid 19 and name hn) | (resid 28 and name ha) | 5.5 | 5.5 | 0.0 | !sing_l |
| assign (resid 19 and name ha) | (resid 20 and name hn) | 3.1 | 3.1 | 0.0 | !sing_s |
| assign (resid 19 and name hz) | (resid 60 and name hn) | 5.5 | 5.5 | 0.0 | !sing_l |
| assign (resid 20 and name ha) | (resid 21 and name hn) | 3.1 | 3.1 | 0.0 | !sing_s |
| assign (resid 20 and name ha) | (resid 26 and name ha) | 3.6 | 3.6 | 0.0 | !sing_l |
| assign (resid 21 and name hn) | (resid 21 and name hd2) | 3.6 | 3.6 | 0.0 | !sing_i |
| assign (resid 21 and name hn) | (resid 25 and name hn) | 5.5 | 5.5 | 0.0 | !sing_m |
| assign (resid 21 and name ha) | (resid 22 and name hn) | 3.6 | 3.6 | 0.0 | !sing_s |
| assign (resid 21 and name ha) | (resid 23 and name hn) | 3.6 | 3.6 | 0.0 | !sing_m |
| assign (resid 22 and name hn) | (resid 22 and name hg) | 5.5 | 5.5 | 0.0 | !sing_i |
| assign (resid 22 and name hn) | (resid 23 and name hn) | 5.5 | 5.5 | 0.0 | !sing_s |
| assign (resid 22 and name hn) | (resid 25 and name hn) | 5.5 | 5.5 | 0.0 | !sing_m |
| assign (resid 22 and name ha) | (resid 23 and name hn) | 4.1 | 4.1 | 0.0 | !sing_s |
| assign (resid 22 and name ha) | (resid 24 and name hn) | 4.1 | 4.1 | 0.0 | !sing_m |
| assign (resid 22 and name hg) | (resid 23 and name hn) | 5.5 | 5.5 | 0.0 | !sing_s |
| assign (resid 23 and name hn) | (resid 24 and name hn) | 4.1 | 4.1 | 0.0 | !sing_s |
| assign (resid 23 and name hn) | (resid 24 and name ha) | 5.5 | 5.5 | 0.0 | !sing_s |
| assign (resid 23 and name ha) | (resid 24 and name hn) | 4.1 | 4.1 | 0.0 | !sing_s |
| assign (resid 23 and name ha) | (resid 25 and name hn) | 5.5 | 5.5 | 0.0 | !sing_m |
| assign (resid 24 and name ha) | (resid 25 and name hn) | 5.5 | 5.5 | 0.0 | !sing_s |
| assign (resid 25 and name hn) | (resid 26 and name hn) | 5.5 | 5.5 | 0.0 | !sing_s |
| assign (resid 25 and name ha) | (resid 26 and name hn) | 2.6 | 2.6 | 0.0 | !sing_s |
| assign (resid 26 and name hn) | (resid 27 and name hn) | 5.5 | 5.5 | 0.0 | !sing_s |
| assign (resid 26 and name ha) | (resid 27 and name hn) | 3.6 | 3.6 | 0.0 | !sing_s |
| assign (resid 27 and name ha) | (resid 28 and name hn) | 2.6 | 2.6 | 0.0 | !sing_s |
| assign (resid 28 and name ha) | (resid 29 and name hn) | 3.1 | 3.1 | 0.0 | !sing_s |
| assign (resid 29 and name ha) | (resid 30 and name hn) | 2.6 | 2.6 | 0.0 | !sing_s |
| assign (resid 30 and name hn) | (resid 31 and name hn) | 5.5 | 5.5 | 0.0 | !sing_s |
| assign (resid 30 and name ha) | (resid 31 and name hn) | 3.1 | 3.1 | 0.0 | !sing_s |
| assign (resid 31 and name hn) | (resid 31 and name hg) | 3.6 | 3.6 | 0.0 | !sing_i |
| assign (resid 31 and name hn) | (resid 32 and name hn) | 5.5 | 5.5 | 0.0 | !sing_s |
| assign (resid 31 and name ha) | (resid 32 and name hn) | 3.1 | 3.1 | 0.0 | !sing_s |
| assign (resid 31 and name ha) | (resid 31 and name hg) | 3.6 | 3.6 | 0.0 | !sing_i |
| assign (resid 32 and name hn) | (resid 32 and name hg) | 3.6 | 3.6 | 0.0 | !sing_i |
| assign (resid 32 and name ha) | (resid 33 and name hn) | 2.6 | 2.6 | 0.0 | !sing_s |
| assign (resid 32 and name ha) | (resid 34 and name hn) | 3.6 | 3.6 | 0.0 | !sing_m |
| assign (resid 33 and name hn) | (resid 34 and name hn) | 3.6 | 3.6 | 0.0 | !sing_s |
| assign (resid 33 and name ha) | (resid 34 and name hn) | 3.1 | 3.1 | 0.0 | !sing_s |
| assign (resid 34 and name hn) | (resid 35 and name hn) | 5.5 | 5.5 | 0.0 | !sing_s |
| assign (resid 34 and name hn) | (resid 44 and name hn) | 5.5 | 5.5 | 0.0 | !sing_l |
| assign (resid 34 and name ha) | (resid 35 and name hn) | 3.1 | 3.1 | 0.0 | !sing_s |
| assign (resid 34 and name ha) | (resid 43 and name ha) | 2.8 | 2.8 | 0.0 | !sing_l |
| assign (resid 34 and name ha) | (resid 44 and name hn) | 3.1 | 3.1 | 0.0 | !sing_l |
| assign (resid 35 and name hn) | (resid 36 and name hn) | 5.5 | 5.5 | 0.0 | !sing_s |
| assign (resid 35 and name hn) | (resid 41 and name ha) | 5.5 | 5.5 | 0.0 | !sing_l |
| assign (resid 35 and name hn) | (resid 42 and name hn) | 3.6 | 3.6 | 0.0 | !sing_l |
| assign (resid 35 and name hn) | (resid 43 and name ha) | 5.5 | 5.5 | 0.0 | !sing_l |
| assign (resid 35 and name hn) | (resid 44 and name hn) | 5.5 | 5.5 | 0.0 | !sing_l |
| assign (resid 35 and name hn) | (resid 44 and name ha) | 5.5 | 5.5 | 0.0 | !sing_l |
| assign (resid 35 and name ha) | (resid 36 and name hn) | 2.6 | 2.6 | 0.0 | !sing_s |
| assign (resid 36 and name hn) | (resid 37 and name hn) | 5.5 | 5.5 | 0.0 | !sing_s |
| assign (resid 36 and name ha) | (resid 37 and name hn) | 2.6 | 2.6 | 0.0 | !sing_s |
| assign (resid 36 and name ha) | (resid 41 and name ha) | 2.8 | 2.8 | 0.0 | !sing_l |
| assign (resid 36 and name ha) | (resid 42 and name hn) | 3.6 | 3.6 | 0.0 | !sing_l |
| assign (resid 37 and name hn) | (resid 40 and name hn) | 3.6 | 3.6 | 0.0 | !sing_m |

TABLE B-continued

| | | | | | |
|---|---|---|---|---|---|
| assign (resid 37 and name hn) | (resid 41 and name ha) | 3.5 | 3.6 | 0.0 | !sing_m |
| assign (resid 37 and name hn) | (resid 42 and name hn) | 5.5 | 5.5 | 0.0 | !sing_l |
| assign (resid 37 and name ha) | (resid 38 and name hn) | 2.6 | 2.6 | 0.0 | !sing_s |
| assign (resid 38 and name hn) | (resid 39 and name hn) | 5.5 | 5.5 | 0.0 | !sing_s |
| assign (resid 39 and name hn) | (resid 40 and name hn) | 3.6 | 3.6 | 0.0 | !sing_s |
| assign (resid 40 and name hn) | (resid 41 and name hn) | 5.5 | 5.5 | 0.0 | !sing_s |
| assign (resid 40 and name ha) | (resid 41 and name hn) | 2.6 | 2.6 | 0.0 | !sing_s |
| assign (resid 41 and name hn) | (resid 42 and name hn) | 5.5 | 5.5 | 0.0 | !sing_s |
| assign (resid 41 and name ha) | (resid 42 and name hn) | 2.6 | 2.6 | 0.0 | !sing_s |
| assign (resid 42 and name ha) | (resid 43 and name hn) | 2.6 | 2.6 | 0.0 | !sing_s |
| assign (resid 42 and name hb) | (resid 43 and name hn) | 3.1 | 3.1 | 0.0 | !sing_s |
| assign (resid 43 and name hn) | (resid 44 and name hn) | 5.5 | 5.5 | 0.0 | !sing_s |
| assign (resid 43 and name ha) | (resid 44 and name hn) | 2.6 | 2.6 | 0.0 | !sing_s |
| assign (resid 44 and name ha) | (resid 46 and name hn) | 3.6 | 3.6 | 0.0 | !sing_m |
| assign (resid 45 and name ha) | (resid 46 and name hn) | 3.6 | 3.6 | 0.0 | !sing_s |
| assign (resid 46 and name ha) | (resid 72 and name hn) | 5.5 | 5.5 | 0.0 | !sing_l |
| assign (resid 47 and name ha) | (resid 48 and name hn) | 2.6 | 2.6 | 0.0 | !sing_s |
| assign (resid 48 and name hn) | (resid 49 and name hn) | 5.5 | 5.5 | 0.0 | !sing_s |
| assign (resid 48 and name hn) | (resid 51 and name hn) | 5.5 | 5.5 | 0.0 | !sing_m |
| assign (resid 48 and name ha) | (resid 49 and name hn) | 3.1 | 3.1 | 0.0 | !sing_s |
| assign (resid 48 and name ha) | (resid 50 and name hn) | 5.5 | 5.5 | 0.0 | !sing_m |
| assign (resid 48 and name hb) | (resid 49 and name hn) | 3.6 | 3.6 | 0.0 | !sing_s |
| assign (resid 48 and name hb) | (resid 50 and name hn) | 5.5 | 5.5 | 0.0 | !sing_m |
| assign (resid 49 and name hn) | (resid 50 and name hn) | 3.6 | 3.6 | 0.0 | !sing_s |
| assign (resid 49 and name hn) | (resid 51 and name hn) | 5.5 | 5.5 | 0.0 | !sing_m |
| assign (resid 49 and name ha) | (resid 50 and name hn) | 3.6 | 3.6 | 0.0 | !sing_s |
| assign (resid 49 and name ha) | (resid 52 and name hn) | 4.1 | 4.1 | 0.0 | !sing_m |
| assign (resid 49 and name ha) | (resid 53 and name ha) | 3.6 | 3.6 | 0.0 | !sing_m |
| assign (resid 49 and name ha) | (resid 54 and name hn) | 3.6 | 3.6 | 0.0 | !sing_l |
| assign (resid 50 and name hn) | (resid 51 and name hn) | 3.6 | 3.6 | 0.0 | !sing_s |
| assign (resid 51 and name hn) | (resid 52 and name hn) | 5.5 | 5.5 | 0.0 | !sing_s |
| assign (resid 51 and name hn) | (resid 53 and name hn) | 4.1 | 4.1 | 0.0 | !sing_m |
| assign (resid 51 and name hn) | (resid 54 and name hn) | 4.1 | 4.1 | 0.0 | !sing_m |
| assign (resid 51 and name ha) | (resid 52 and name hn) | 3.1 | 3.1 | 0.0 | !sing_s |
| assign (resid 52 and name hn) | (resid 53 and name hn) | 3.6 | 3.6 | 0.0 | !sing_s |
| assign (resid 52 and name ha) | (resid 53 and name hn) | 3.6 | 3.6 | 0.0 | !sing_s |
| assign (resid 53 and name hn) | (resid 54 and name hn) | 4.1 | 4.1 | 0.0 | !sing_s |
| assign (resid 53 and name ha) | (resid 54 and name hn) | 3.6 | 3.6 | 0.0 | !sing_s |
| assign (resid 53 and name ha) | (resid 56 and name hn) | 2.8 | 2.8 | 0.0 | !sing_m |
| assign (resid 54 and name hn) | (resid 55 and name hn) | 3.6 | 3.6 | 0.0 | !sing_s |
| assign (resid 55 and name hn) | (resid 56 and name hn) | 3.1 | 3.1 | 0.0 | !sing_s |
| assign (resid 56 and name hn) | (resid 57 and name hn) | 5.5 | 5.5 | 0.0 | !sing_s |
| assign (resid 56 and name ha) | (resid 57 and name hn) | 3.6 | 3.6 | 0.0 | !sing_s |
| assign (resid 57 and name hn) | (resid 59 and name hn) | 5.5 | 5.5 | 0.0 | !sing_m |
| assign (resid 57 and name hn) | (resid 60 and name hn) | 5.5 | 5.5 | 0.0 | !sing_m |
| assign (resid 57 and name hn) | (resid 90 and name hn) | 5.5 | 5.5 | 0.0 | !sing_l |
| assign (resid 57 and name hn) | (resid 90 and name ha) | 2.6 | 2.6 | 0.0 | !sing_l |
| assign (resid 57 and name hn) | (resid 91 and name ha) | 5.5 | 5.5 | 0.0 | !sing_l |
| assign (resid 57 and name hn) | (resid 91 and name hn) | 5.5 | 5.5 | 0.0 | !sing_l |
| assign (resid 57 and name ha) | (resid 91 and name ha) | 3.6 | 3.6 | 0.0 | !sing_l |
| assign (resid 58 and name hn) | (resid 59 and name hn) | 3.6 | 3.6 | 0.0 | !sing_s |
| assign (resid 58 and name hn) | (resid 60 and name hn) | 5.5 | 5.5 | 0.0 | !sing_m |
| assign (resid 58 and name ha) | (resid 59 and name hn) | 3.6 | 3.6 | 0.0 | !sing_s |
| assign (resid 59 and name hn) | (resid 60 and name hn) | 3.6 | 3.6 | 0.0 | !sing_s |
| assign (resid 59 and name ha) | (resid 60 and name hn) | 3.6 | 3.6 | 0.0 | !sing_s |
| assign (resid 60 and name hn) | (resid 61 and name hn) | 5.5 | 5.5 | 0.0 | !sing_s |
| assign (resid 60 and name hn) | (resid 78 and name ha) | 5.5 | 5.5 | 0.0 | !sing_l |
| assign (resid 60 and name ha) | (resid 61 and name hn) | 2.6 | 2.6 | 0.0 | !sing_s |
| assign (resid 60 and name ha) | (resid 77 and name hn) | 5.5 | 5.5 | 0.0 | !sing_l |
| assign (resid 60 and name ha) | (resid 78 and name ha) | 2.8 | 2.8 | 0.0 | !sing_i |
| assign (resid 60 and name ha) | (resid 79 and name hn) | 3.6 | 3.6 | 0.0 | !sing_l |
| assign (resid 61 and name hn) | (resid 77 and name hn) | 3.6 | 3.6 | 0.0 | !sing_l |
| assign (resid 61 and name hn) | (resid 78 and name ha) | 3.6 | 3.6 | 0.0 | !sing_l |
| assign (resid 61 and name hn) | (resid 79 and name hn) | 5.5 | 5.5 | 0.0 | !sing_l |
| assign (resid 61 and name ha) | (resid 62 and name hn) | 2.6 | 2.6 | 0.0 | !sing_s |
| assign (resid 62 and name ha) | (resid 63 and name hn) | 2.6 | 2.6 | 0.0 | !sing_s |
| assign (resid 62 and name ha) | (resid 76 and name ha) | 2.8 | 2.8 | 0.0 | !sing_l |
| assign (resid 63 and name hn) | (resid 63 and name hb) | 3.6 | 3.6 | 0.0 | !sing_i |
| assign (resid 63 and name hn) | (resid 64 and name hn) | 5.5 | 5.5 | 0.0 | !sing_s |
| assign (resid 63 and name hn) | (resid 75 and name hn) | 3.6 | 3.6 | 0.0 | !sing_l |
| assign (resid 63 and name hn) | (resid 76 and name ha) | 5.5 | 5.5 | 0.0 | !sing_l |
| assign (resid 63 and name ha) | (resid 64 and name hn) | 2.6 | 2.6 | 0.0 | !sing_s |
| assign (resid 63 and name hb) | (resid 64 and name hn) | 3.1 | 3.1 | 0.0 | !sing_s |
| assign (resid 64 and name ha) | (resid 74 and name ha) | 2.8 | 2.8 | 0.0 | !sing_l |
| assign (resid 65 and name ha) | (resid 66 and name hn) | 2.6 | 2.6 | 0.0 | !sing_s |
| assign (resid 66 and name hn) | (resid 67 and name hn) | 5.5 | 5.5 | 0.0 | !sing_s |
| assign (resid 67 and name hn) | (resid 68 and name lan) | 5.5 | 5.5 | 0.0 | !sing_s |
| assign (resid 67 and name ha) | (resid 68 and name hn) | 3.6 | 3.6 | 0.0 | !sing_s |
| assign (resid 70 and name hn) | (resid 71 and name hn) | 3.1 | 3.1 | 0.0 | !sing_s |

TABLE B-continued

| | | | | | |
|---|---|---|---|---|---|
| assign (resid 70 and name ha) | (resid 71 and name hn) | 3.6 | 3.6 | 0.0 | !sing_s |
| assign (resid 71 and name hn) | (resid 72 and name hn) | 3.6 | 3.6 | 0.0 | !sing_s |
| assign (resid 72 and name hn) | (resid 73 and name hn) | 5.5 | 5.5 | 0.0 | !sing_s |
| assign (resid 72 and name ha) | (resid 73 and name hn) | 2.6 | 2.6 | 0.0 | !sing_s |
| assign (resid 73 and name hn) | (resid 74 and name hn) | 5.5 | 5.5 | 0.0 | !sing_s |
| assign (resid 73 and name ha) | (resid 74 and name hn) | 2.6 | 2.6 | 0.0 | !sing_s |
| assign (resid 74 and name hn) | (resid 74 and name hb) | 3.1 | 3.1 | 0.0 | !sing_i |
| assign (resid 74 and name ha) | (resid 75 and name hn) | 2.6 | 2.6 | 0.0 | !sing_s |
| assign (resid 75 and name hn) | (resid 75 and name hb) | 3.1 | 3.1 | 0.0 | !sing_i |
| assign (resid 75 and name ha) | (resid 76 and name hn) | 2.6 | 2.6 | 0.0 | !sing_s |
| assign (resid 75 and name hb) | (resid 76 and name hn) | 3.6 | 3.6 | 0.0 | !sing_s |
| assign (resid 76 and name ha) | (resid 77 and name hn) | 2.6 | 2.6 | 0.0 | !sing_s |
| assign (resid 77 and name hn) | (resid 78 and name hn) | 5.5 | 5.5 | 0.0 | !sing_s |
| assign (resid 77 and name ha) | (resid 78 and name hn) | 2.8 | 2.8 | 0.0 | !sing_s |
| assign (resid 78 and name hn) | (resid 79 and name hn) | 5.5 | 5.5 | 0.0 | !sing_s |
| assign (resid 78 and name ha) | (resid 79 and name hn) | 2.6 | 2.6 | 0.0 | !sing_s |
| assign (resid 79 and name hn) | (resid 79 and name hb) | 3.6 | 3.6 | 0.0 | !sing_i |
| assign (resid 79 and name hn) | (resid 80 and name hn) | 3.6 | 3.6 | 0.0 | !sing_s |
| assign (resid 79 and name hb) | (resid 80 and name hn) | 5.5 | 5.5 | 0.0 | !sing_s |
| assign (resid 81 and name ha) | (resid 82 and name hn) | 3.6 | 3.6 | 0.0 | !sing_s |
| assign (resid 81 and name ha) | (resid 83 and name hn) | 4.1 | 4.1 | 0.0 | !sing_m |
| assign (resid 82 and name hn) | (resid 83 and name hn) | 4.1 | 4.1 | 0.0 | !sing_s |
| assign (resid 82 and name ha) | (resid 83 and name hn) | 4.1 | 4.1 | 0.0 | !sing_s |
| assign (resid 83 and name hn) | (resid 84 and name hn) | 5.5 | 5.5 | 0.0 | !sing_s |
| assign (resid 83 and name ha) | (resid 84 and name hn) | 2.6 | 2.6 | 0.0 | !sing_s |
| assign (resid 84 and name hn) | (resid 92 and name hn) | 5.5 | 5.5 | 0.0 | !sing_l |
| assign (resid 84 and name hn) | (resid 93 and name hn) | 5.5 | 5.5 | 0.0 | !sing_l |
| assign (resid 85 and name ha) | (resid 86 and name hn) | 2.6 | 2.6 | 0.0 | !sing_s |
| assign (resid 85 and name ha) | (resid 92 and name ha) | 2.8 | 2.8 | 0.0 | !sing_l |
| assign (resid 86 and name hn) | (resid 86 and name hg) | 3.6 | 3.6 | 0.0 | !sing_i |
| assign (resid 86 and name hn) | (resid 87 and name hn) | 5.5 | 5.5 | 0.0 | !sing_s |
| assign (resid 86 and name hn) | (resid 89 and name hn) | 4.1 | 4.1 | 0.0 | !sing_m |
| assign (resid 86 and name hn) | (resid 90 and name hn) | 5.5 | 5.5 | 0.0 | !sing_m |
| assign (resid 86 and name hn) | (resid 91 and name hn) | 3.6 | 3.6 | 0.0 | !sing_l |
| assign (resid 86 and name ha) | (resid 87 and name hn) | 3.6 | 3.6 | 0.0 | !sing_s |
| assign (resid 87 and name hn) | (resid 88 and name hn) | 4.1 | 4.1 | 0.0 | !sing_s |
| assign (resid 87 and name ha) | (resid 88 and name hn) | 3.1 | 3.1 | 0.0 | !sing_s |
| assign (resid 88 and name hn) | (resid 89 and name hn) | 4.1 | 4.1 | 0.0 | !sing_s |
| assign (resid 88 and name hn) | (resid 90 and name hn) | 5.5 | 5.5 | 0.0 | !sing_m |
| assign (resid 88 and name ha) | (resid 89 and name hn) | 4.1 | 4.1 | 0.0 | !sing_s |
| assign (resid 89 and name hn) | (resid 90 and name hn) | 3.6 | 3.6 | 0.0 | !sing_s |
| assign (resid 90 and name hn) | (resid 90 and name hb) | 3.6 | 3.6 | 0.0 | !sing_i |
| assign (resid 90 and name hn) | (resid 91 and name hn) | 3.1 | 3.1 | 0.0 | !sing_s |
| assign (resid 90 and name hb) | (resid 91 and name hn) | 5.5 | 5.5 | 0.0 | !sing_s |
| assign (resid 91 and name hn) | (resid 92 and name hn) | 5.5 | 5.5 | 0.0 | !sing_s |
| assign (resid 91 and name ha) | (resid 92 and name hn) | 3.1 | 3.1 | 0.0 | !sing_s |
| assign (resid 92 and name ha) | (resid 93 and name hn) | 3.1 | 3.1 | 0.0 | !sing_s |
| class hbnd | | | | | |
| assign (resid 17 and name hn) | (resid 29 and name o) | 2.0 | 0.3 | 0.3 | !hbnd |
| assign (resid 17 and name n) | (resid 29 and name o) | 3.3 | 0.3 | 0.3 | !hbnd |
| assign (resid 17 and name o) | (resid 29 and name hn) | 2.0 | 0.3 | 0.3 | !hbnd |
| assign (resid 17 and name o) | (resid 29 and name n) | 3.3 | 0.3 | 0.3 | !hbnd |
| assign (resid 19 and name hn) | (resid 27 and name o) | 2.0 | 0.3 | 0.3 | !hbnd |
| assign (resid 19 and name n) | (resid 27 and name o) | 3.3 | 0.3 | 0.3 | !hbnd |
| assign (resid 19 and name o) | (resid 27 and name hn) | 2.0 | 0.3 | 0.3 | !hbnd |
| assign (resid 19 and name o) | (resid 27 and name n) | 3.3 | 0.3 | 0.3 | !hbnd |
| assign (resid 35 and name hn) | (resid 42 and name o) | 2.0 | 0.3 | 0.3 | !hbnd |
| assign (resid 35 and name n) | (resid 42 and name o) | 3.3 | 0.3 | 0.3 | !hbnd |
| assign (resid 35 and name o) | (resid 42 and name hn) | 2.0 | 0.3 | 0.3 | !hbnd |
| assign (resid 35 and name o) | (resid 42 and name n) | 3.3 | 0.3 | 0.3 | !hbnd |
| assign (resid 61 and name hn) | (resid 77 and name o) | 2.0 | 0.3 | 0.3 | !hbnd |
| assign (resid 61 and name n) | (resid 77 and name o) | 3.3 | 0.3 | 0.3 | !hbnd |
| assign (resid 61 and name o) | (resid 77 and name hn) | 2.0 | 0.3 | 0.3 | !hbnd |
| assign (resid 61 and name o) | (resid 77 and name n) | 3.3 | 0.3 | 0.3 | !hbnd |
| assign (resid 63 and name hn) | (resid 75 and name o) | 2.0 | 0.3 | 0.3 | !hbnd |
| assign (resid 63 and name n) | (resid 75 and name o) | 3.3 | 0.3 | 0.3 | !bbnd |
| assign (resid 63 and name o) | (resid 75 and name hn) | 2.0 | 0.3 | 0.3 | !hbnd |
| assign (resid 63 and name o) | (resid 75 and name n) | 3.3 | 0.3 | 0.3 | !hbnd |

! dihedral angle restraints    X-PLOR format
!
! chi-1    22 restraints
! phi    25 restraints
! psi    33 restraints
! chi-2    5 restraints
!<ENERGY>    <ANGLE> <RANGE> <EXPONENT>
! chi-1 restraints
assign    (resid 15 and name n ) (resid 15 and name ca)
        (resid 15 and name cb) (resid 15 and name cg)    1.0  −60.0    40.0    2

TABLE B-continued

| | | | | | | | |
|---|---|---|---|---|---|---|---|
| assign | (resid 19 and name n ) | (resid 19 and name ca) | | | | | |
| | (resid 19 and name cb) | (resid 19 and name cg) | 1.0 | 180.0 | 40.0 | 2 | |
| assign | (resid 22 and name n ) | (resid 22 and name ca) | | | | | |
| | (resid 22 and name cb) | (resid 22 and name cg) | 1.0 | −60.0 | 40.0 | 2 | |
| assign | (resid 23 and name n ) | (resid 23 and name ca) | | | | | |
| | (resid 23 and name cb) | (resid 23 and name cg) | 1.0 | 60.0 | 40.0 | 2 | |
| assign | (resid 30 and name n ) | (resid 30 and name ca) | | | | | |
| | (resid 30 and name cb) | (resid 30 and name sg) | 1.0 | −60.0 | 40.0 | 2 | |
| assign | (resid 31 and name n ) | (resid 31 and name ca) | | | | | |
| | (resid 31 and name cb) | (resid 31 and name cg) | 1.0 | −60.0 | 40.0 | 2 | |
| assign | (resid 32 and name n ) | (resid 32 and name ca) | | | | | |
| | (resid 32 and name cb) | (resid 32 and name cg) | 1.0 | −60.0 | 40.0 | 2 | |
| assign | (resid 33 and name n ) | (resid 33 and name ca) | | | | | |
| | (resid 33 and name cb) | (resid 33 and name cg) | 1.0 | −60.0 | 40.0 | 2 | |
| assign | (resid 34 and name n ) | (resid 34 and name ca) | | | | | |
| | (resid 34 and name cb) | (resid 34 and name cg) | 1.0 | −60.0 | 40.0 | 2 | |
| assign | (resid 35 and name n ) | (resid 35 and name ca) | | | | | |
| | (resid 35 and name cb) | (resid 35 and name cg) | 1.0 | 60.0 | 40.0 | 2 | |
| assign | (resid 41 and name n ) | (resid 41 and name ca) | | | | | |
| | (resid 41 and name cb) | (resid 41 and name sg) | 1.0 | −60.0 | 40.0 | 2 | |
| assign | (resid 42 and name n ) | (resid 42 and name ca) | | | | | |
| | (resid 42 and name cb) | (resid 42 and name cg1) | 1.0 | −60.0 | 40.0 | 2 | |
| assign | (resid 49 and name n ) | (resid 49 and name ca) | | | | | |
| | (resid 49 and name cb) | (resid 49 and name sg) | 1.0 | −60.0 | 40.0 | 2 | |
| assign | (resid 52 and name n ) | (resid 52 and name ca) | | | | | |
| | (resid 52 and name cb) | (resid 52 and name cg) | 1.0 | 60.0 | 40.0 | 2 | |
| assign | (resid 53 and name n ) | (resid 53 and name ca) | | | | | |
| | (resid 53 and name cb) | (resid 53 and name cg) | 1.0 | 180.0 | 40.0 | 2 | |
| assign | (resid 56 and name n ) | (resid 56 and name ca) | | | | | |
| | (resid 56 and name cb) | (resid 56 and name sg) | 1.0 | −60.0 | 40.0 | 2 | |
| assign | (resid 62 and name n ) | (resid 62 and name ca) | | | | | |
| | (resid 62 and name cb) | (resid 62 and name sg) | 1.0 | 180.0 | 40.0 | 2 | |
| assign | (resid 74 and name n ) | (resid 74 and name ca) | | | | | |
| | (resid 74 and name cb) | (resid 74 and name cg1) | 1.0 | −60.0 | 40.0 | 2 | |
| assign | (resid 76 and name n ) | (resid 76 and name ca) | | | | | |
| | (resid 76 and name cb) | (resid 76 and name sg) | 1.0 | −60.0 | 40.0 | 2 | |
| assign | (resid 78 and name n ) | (resid 78 and name ca) | | | | | |
| | (resid 78 and name cb) | (resid 78 and name sg) | 1.0 | −60.0 | 40.0 | 2 | |
| assign | (resid 87 and name n ) | (resid 87 and name ca) | | | | | |
| | (resid 87 and name cb) | (resid 87 and name cg) | 1.0 | −60.0 | 40.0 | 2 | |
| assign | (resid 92 and name n ) | (resid 92 and name ca) | | | | | |
| | (resid 92 and name cb) | (resid 92 and name sg) | 1.0 | −60.0 | 40.0 | 2 | |
| ! phi restraints | | | | | | | |
| assign | (resid 14 and name c ) | (resid 15 and name n ) | | | | | |
| | (resid 15 and name ca) | (resid 15 and name c) | 1.0 | 60.0 | 50.0 | 2 | !HN(CO)HB |
| assign | (resid 18 and name c ) | (resid 19 and name n ) | | | | | |
| | (resid 19 and name ca) | (resid 19 and name c) | 1.0 | −120.0 | 50.0 | 2 | !HNHA 8.9 Hz |
| assign | (resid 27 and name c ) | (resid 28 and name n ) | | | | | |
| | (resid 28 and name ca) | (resid 28 and name c) | 1.0 | −120.0 | 70.0 | 2 | !HNHA 7.6 Hz |
| assign | (resid 29 and name c ) | (resid 30 and name n ) | | | | | |
| | (resid 30 and name ca) | (resid 30 and name c) | 1.0 | −78.0 | 50.0 | 2 | |
| assign | (resid 31 and name c ) | (resid 32 and name n ) | | | | | |
| | (resid 32 and name ca) | (resid 32 and name c) | 1.0 | −84.0 | 50.0 | 2 | |
| assign | (resid 32 and name c ) | (resid 33 and name n ) | | | | | |
| | (resid 33 and name ca) | (resid 33 and name c) | 1.0 | 60.0 | 50.0 | 2 | !HN(CO)HB |
| assign | (resid 33 and name c ) | (resid 34 and name n ) | | | | | |
| | (resid 34 and name ca) | (resid 34 and name c) | 1.0 | −120.0 | 50.0 | 2 | !HNHA 8.2 Hz |
| assign | (resid 34 and name c ) | (resid 35 and name n ) | | | | | |
| | (resid 35 and name ca) | (resid 35 and name c) | 1.0 | −120.0 | 50.0 | 2 | !HNHA 8.45 Hz |
| assign | (resid 36 and name c ) | (resid 37 and name n ) | | | | | |
| | (resid 37 and name ca) | (resid 37 and name c) | 1.0 | −120.0 | 50.0 | 2 | !HNHA 8.6 Hz |
| assign | (resid 38 and name c ) | (resid 39 and name n ) | | | | | |
| | (resid 39 and name ca) | (resid 39 and name c) | 1.0 | −120.0 | 50.0 | 2 | !HNHA 8.6 Hz |
| assign | (resid 39 and name c ) | (resid 40 and name n ) | | | | | |
| | (resid 40 and name ca) | (resid 40 and name c) | 1.0 | −120.0 | 50.0 | 2 | !HNHA 8.3 Hz |
| assign | (resid 40 and name c ) | (resid 41 and name n ) | | | | | |
| | (resid 41 and name ca) | (resid 41 and name c) | 1.0 | −120.0 | 50.0 | 2 | !HNHA 8.8 Hz |
| assign | (resid 41 and name c ) | (resid 42 and name n ) | | | | | |
| | (resid 42 and name ca) | (resid 42 and name c) | 1.0 | −120.0 | 50.0 | 2 | !HNHA 8.5 Hz |
| assign | (resid 49 and name c ) | (resid 50 and name n ) | | | | | |
| | (resid 50 and name ca) | (resid 50 and name c) | 1.0 | −75.0 | 50.0 | 2 | |
| assign | (resid 50 and name c ) | (resid 51 and name n ) | | | | | |
| | (resid 51 and name ca) | (resid 51 and name c) | 1.0 | −120.0 | 50.0 | 2 | !HNHA 8.5 Hz |
| assign | (resid 52 and name c ) | (resid 53 and name n ) | | | | | |
| | (resid 53 and name ca) | (resid 53 and name c) | 1.0 | 60.0 | 50.0 | 2 | !HN(CO)HB |
| assign | (resid 55 and name c ) | (resid 56 and name n ) | | | | | |
| | (resid 56 and name ca) | (resid 56 and name c) | 1.0 | −60.0 | 50.0 | 2 | !HNHA 5.0 Hz |
| assign | (resid 58 and name c ) | (resid 59 and name n ) | | | | | |
| | (resid 59 and name ca) | (resid 59 and name c) | 1.0 | −120.0 | 50.0 | 2 | !HNHA 8.8 Hz |

TABLE B-continued

| | | | | | | | |
|---|---|---|---|---|---|---|---|
| assign | (resid 59 and name c ) | (resid 60 and name n ) | | | | | |
| | (resid 60 and name ca) | (resid 60 and name c) | 1.0 | −120.0 | 50.0 | 2 | !HNHA 8.2 Hz |
| assign | (resid 60 and name c ) | (resid 61 and name n ) | | | | | |
| | (resid 61 and name ca) | (resid 61 and name c) | 1.0 | −120.0 | 50.0 | 2 | !HNHA 8.1 Hz |
| assign | (resid 61 and name c ) | (resid 62 and name n ) | | | | | |
| | (resid 62 and name ca) | (resid 62 and name c) | 1.0 | −150.0 | 70.0 | 2 | !HNHA 7.9 Hz |
| assign | (resid 62 and name c ) | (resid 63 and name n ) | | | | | |
| | (resid 63 and name ca) | (resid 63 and name c) | 1.0 | −120.0 | 50.0 | 2 | !HNHA 8.7 Hz |
| assign | (resid 73 and name c ) | (resid 74 and name n ) | | | | | |
| | (resid 74 and name ca) | (resid 74 and name c) | 1.0 | −120.0 | 50.0 | 2 | |
| assign | (resid 74 and name c ) | (resid 75 and name n ) | | | | | |
| | (resid 75 and name ca) | (resid 75 and name c) | 1.0 | −120.0 | 50.0 | 2 | !HNHA 9.15 Hz |
| assign | (resid 76 and name c ) | (resid 77 and name n ) | | | | | |
| | (resid 77 and name ca) | (resid 77 and name c) | 1.0 | −120.0 | 50.0 | 2 | !HNHA 8.2 Hz |
| !psi restraints | | | | | | | |
| assign | (resid 15 and name n) | (resid 15 and name ca) | | | | | |
| | (resid 15 and name c) | (resid 16 and name n ) | 1.0 | 50.0 | 50.0 | 2 | |
| assign | (resid 19 and name n) | (resid 19 and name ca) | | | | | |
| | (resid 19 and name a) | (resid 20 and name n ) | 1.0 | 120.0 | 75.0 | 2 | |
| assign | (resid 25 and name n) | (resid 25 and name ca) | | | | | |
| | (resid 25 and name c) | (resid 26 and name n ) | 1.0 | 120.0 | 75.0 | 2 | |
| assign | (resid 27 and name n) | (resid 27 and name ca) | | | | | |
| | (resid 27 and name c) | (resid 28 and name n ) | 1.0 | 120.0 | 75.0 | 2 | |
| assign | (resid 28 and name n) | (resid 28 and name ca) | | | | | |
| | (resid 28 and name c) | (resid 29 and name n ) | 1.0 | 120.0 | 75.0 | 2 | |
| assign | (resid 29 and name n) | (resid 29 and name ca) | | | | | |
| | (resid 29 and name c) | (resid 30 and name n ) | 1.0 | 120.0 | 60.0 | 2 | |
| assign | (resid 30 and name n) | (resid 30 and name ca) | | | | | |
| | (resid 30 and name c) | (resid 31 and name n ) | 1.0 | 125.0 | 75.0 | 2 | |
| assign | (resid 31 and name n) | (resid 31 and name ca) | | | | | |
| | (resid 31 and name a) | (resid 32 and name n ) | 1.0 | 120.0 | 75.0 | 2 | |
| assign | (resid 32 and name n) | (resid 32 and name ca) | | | | | |
| | (resid 32 and name c) | (resid 33 and name n ) | 1.0 | 174.0 | 50.0 | 2 | |
| assign | (resid 33 and name n) | (resid 33 and name ca) | | | | | |
| | (resid 33 and name c) | (resid 34 and name n ) | 1.0 | 60.0 | 50.0 | 2 | |
| assign | (resid 34 and name n) | (resid 34 and name ca) | | | | | |
| | (resid 34 and name c) | (resid 35 and name n ) | 1.0 | 159.0 | 50.0 | 2 | |
| assign | (resid 35 and name n) | (resid 35 and name ca) | | | | | |
| | (resid 35 and name c) | (resid 36 and name n ) | 1.0 | 156.0 | 50.0 | 2 | |
| assign | (resid 36 and name n) | (resid 36 and name ca) | | | | | |
| | (resid 36 and name c) | (resid 37 and name n ) | 1.0 | 120.0 | 60.0 | 2 | |
| assign | (resid 37 and name n) | (resid 37 and name ca) | | | | | |
| | (resid 37 and name c) | (resid 38 and name n ) | 1.0 | 120.0 | 60.0 | 2 | |
| assign | (resid 40 and name n) | (resid 40 and name ca) | | | | | |
| | (resid 40 and name c) | (resid 41 and name n ) | 1.0 | 120.0 | 60.0 | 2 | |
| assign | (resid 41 and name n) | (resid 41 and name ca) | | | | | |
| | (resid 41 and name c) | (resid 42 and name n ) | 1.0 | 120.0 | 60.0 | 2 | |
| assign | (resid 42 and name n) | (resid 42 and name ca) | | | | | |
| | (resid 42 and name c) | (resid 43 and name n ) | 1.0 | 120.0 | 60.0 | 2 | |
| assign | (resid 43 and name n) | (resid 43 and name ca) | | | | | |
| | (resid 43 and name c) | (resid 44 and name n ) | 1.0 | 120.0 | 60.0 | 2 | |
| assign | (resid 45 and name n) | (resid 45 and name ca) | | | | | |
| | (resid 45 and name a) | (resid 46 and name n ) | 1.0 | −60.0 | 50.0 | 2 | !HNHB |
| assign | (resid 51 and name n) | (resid 51 and name ca) | | | | | |
| | (resid 51 and name c) | (resid 52 and name n ) | 1.0 | 120.0 | 75.0 | 2 | |
| assign | (resid 53 and name n ) | (resid 53 and name ca) | | | | | |
| | (resid 53 and name c) | (resid 54 and name n ) | 1.0 | 50.0 | 50.0 | 2 | |
| assign | (resid 58 and name n ) | (resid 58 and name ca) | | | | | |
| | (resid 58 and name c) | (resid 59 and name n ) | 1.0 | −60.0 | 50.0 | 2 | !HNHB |
| assign | (resid 59 and name n ) | (resid 59 and name ca) | | | | | |
| | (resid 59 and name c ) | (resid 60 and name n ) | 1.0 | 33.0 | 50.0 | 2 | |
| assign | (resid 60 and name n ) | (resid 60 and name ca) | | | | | |
| | (resid 60 and name c ) | (resid 61 and name n ) | 1.0 | 162.0 | 50.0 | 2 | |
| assign | (resid 61 and name n ) | (resid 61 and name ca) | | | | | |
| | (resid 61 and name c ) | (resid 62 and name n ) | 1.0 | 120.0 | 60.0 | 2 | |
| assign | (resid 62 and name n ) | (resid 62 and name ca) | | | | | |
| | (resid 62 and name c ) | (resid 63 and name n ) | 1.0 | 120.0 | 60.0 | 2 | |
| assign | (resid 63 and name n ) | (resid 63 and name ca) | | | | | |
| | (resid 63 and name c ) | (resid 64 and name n ) | 1.0 | 165.0 | 50.0 | 2 | |
| assign | (resid 74 and name n ) | (resid 74 and name ca) | | | | | |
| | (resid 74 and name c ) | (resid 75 and name n ) | 1.0 | 120.0 | 60.0 | 2 | |
| assign | (resid 75 and name n ) | (resid 75 and name ca) | | | | | |
| | (resid 75 and name c ) | (resid 76 and name n ) | 1.0 | 120.0 | 60.0 | 2 | |
| assign | (resid 76 and name n ) | (resid 76 and name ca) | | | | | |
| | (resid 76 and name c ) | (resid 77 and name n ) | 1.0 | 120.0 | 60.0 | 2 | |
| assign | (resid 78 and name n ) | (resid 78 and name ca) | | | | | |
| | (resid 78 and name c ) | (resid 79 and name n ) | 1.0 | 120.0 | 60.0 | 2 | |
| assign | (resid 83 and name n ) | (resid 83 and name ca) | | | | | |
| | (resid 83 and name c ) | (resid 84 and name n ) | 1.0 | 120.0 | 60.0 | 2 | |

TABLE B-continued

```
assign   (resid 92 and name n )   (resid 92 and name ca)
         (resid 92 and name c )   (resid 93 and name n )     1.0   120.0   75.0   2
!chi-2 restraints
assign   (resid 2 and name ca)    (resid 2 and name ob)
         (resid 2 and name cg1)   (resid 2 and name cd1)     1.0   -60.0   40.0   2   !LRCH
assign   (resid 31 and name ca)   (resid 31 and name cb)
         (resid 31 and name cg)   (resid 31 and name cd1)    1.0   180.0   40.0   2   !LRCH
assign   (resid 32 and name ca)   (resid 32 and name cb)
         (resid 32 and name cg)   (resid 32 and name cd1)    1.0   180.0   40.0   2   !LRCH
assign   (resid 74 and name ca)   (resid 74 and name cb)
         (resid 74 and name cg1)(resid 74 and name cd1)      1.0   -60.0   40.0   2   !LRCH
assign   (resid 90 and name ca)   (resid 90 and name cb)
         (resid 90 and name cg1)(resid 90 and name cd1)      1.0   180.0   40.0   2   !LRCH
```

EXAMPLE 3

Identification of Blocking Antibodies Using a Competitive Binding Assay and Immobilised Wild Type GST-MSP-$1_{19}$ In previous studies antibodies that blocked the action of the neutralising antibodies 12.8 and 12.10 had been defined either directly in the MSP-$1_{42}$ processing assay (Blackman et al., 1994) in a coupled erythrocyte invasion-MSP-$1_{42}$ processing assay (Guevara et al., 1997) or in a competitive radioimmunoassay with merozoite protein as the antigen (Guevara et al., 1997). These studies have been extended using recombinant MSP-1 and BIAcore analysis.

A recombinant fusion protein comprising wild type MSP-$1_{19}$ fused to GST was coupled to the sensor chip and competitor antibody was first allowed to bind to the antigen. Then a solution of either mAb 12.8 or 12.10 was passed over the chip and the amount of binding of this second antibody was quantified. If the first antibody interferes with the binding of the second antibody then this is reflected in a reduction in the amount of second antibody bound.

Methods

The wild type GST-MSP-$1_{19}$ was coupled to a CM5 sensor chip. The binding assays were performed with a constant flow rate of 5 µl min$^{-1}$ at 25° C. For binding, purified mAbs 1E1, 8A12 and 2F10 at 100 µg ml$^{-1}$ in HBS-EP buffer (10 mM HEPES pH7.4 containing 150 mM NaCl, 3 mM EDTA and 0.005% v/v polysorbate 20); mAbs 1E8, 9C8, 12D11, 111.2 and 111.4 in cell culture medium supernatant; mAbs 2.2, 7.5 and 89.1 at 1:10 dilution of ascitic fluid in HBS-EP buffer; and mouse α-GST antibody at 1:10 dilution serum in HBS-EP buffer were allowed to interact with immobilised wild type GST-MSP-$1_{19}$ for 10 min. After allowing 5 min for dissociation of low affinity interactions, either mAb 12.8 or 12.10 at 100 µg ml$^{-1}$ in HBS-EP buffer was added and allowed to bind for 10 min. After washing the chip for 5 min the binding of 12.8 or 12.10 was measured. The chip was regenerated by washing off bound antibody with 10 mM glycine-HCl, pH 2.4, or when required with 100 mM glycine-HCl, pH 1.8, for 3 min.

Results

The results are shown in FIG. 12. All the competitor antibodies bind to the GST-MSP-$1_{19}$ antigen, with the exception of mAb89.1 which is a negative control. As expected, mAbs 12.8 and 12.10 competed with each other (Guevara et al., 1997). The other antibodies which do not inhibit processing could to greater or lesser interfere with the binding of 12.8 and 12.10. As expected from previous studies mAbs 1E1, and 7.5 blocked both 12.8 and 12.10, whereas 2.2 and 111.4 blocked 12.8. Another particularly effective blocking antibody identified in this study was mAb9C8.

EXAMPLE 4

Immunization of Small Animals with Modified GST-MSP-$1_{19}$ and Analysis of the Antibodies Induced To determine whether or not the modified proteins were immunogenic, recombinant GST-MSP-$1_{19}$ fusion proteins were used to raise antibodies by immunisation.

Methods

Two modified proteins containing either 3[27+31+43] or 4[15+27+31+43] amino acid substitutions, respectively, were used to immunise rabbits and mice. The rabbits were immunised subcutaneously with MSP-$1_{19}$ protein in Freund's complete adjuvant and then boosted on three occasions with 200 µg of the protein in Freund's incomplete adjuvant 21, 42 and 63 days later, and serum samples were collected.

The presence and level of antibodies binding to the native MSP-1 protein in the parasite was assessed by indirect immunofluorescence using acetone fixed smears of parasite-infected erythrocytes. The sera were diluted serially in phosphate buffered saline (PBS) and incubated on the slide for 30 min at room temperature. After washing, the slides were incubated with FITC conjugated goat anti-rabbit or anti-mouse IgG, washed, and then examined by fluorescence microscopy.

The sera were also analysed in an MSP-1 secondary processing assay. Analysis and quantitation of secondary processing of MSP-1 in merozoite preparations was by a modification of an assay described previously (Blackman et al., 1994). Washed *P. falciparum* 3D7 merozoites were resuspended in ice-cold 50 mM Tris-HCl pH 7.5 containing 10 mM CaCl$_2$ and 2 mM MgCl$_2$ (reaction buffer). Aliquots of about 1×10$^9$ merozoites were dispensed into 1.5 ml centrifuge tubes on ice, and the parasites pelleted in a microfuge at 13,000×g for 2 minutes at 4° C. The supernatant was removed, and individual merozoite pellets were then resuspended on ice in 25 µl of reaction buffer further supplemented with protease inhibitor or antibodies as appropriate. Merozoites were maintained on ice for 20 min to allow antibody binding, then transferred to a 37° C. water bath for one hour to allow processing to proceed. Assays always included the following controls: a "positive processing" control sample of merozoites resuspended in reaction buffer only; a "negative processing" control sample of merozoites resuspended in reaction buffer plus 1 mM PMSF; and a zero time (0h) control, in which processing was stopped before the 37° C. incubation step. The processing was assayed using the western blot-based method and by a modified processing assay. Supernatants from the assays were obtained after centrifugation for 30 min at 4° C., 13,000×g to remove the insoluble material. The amount of MSP-1$_{33}$ in the supernatants was measured using an ELISA method. Fifty microliters of diluted sample supernatants were added to the wells of an ELISA plate (NUNC F96 Cert. Maxisorp) that had been coated with 100 μl/well of 4 μg ml$^{-1}$ human mAb X509 in PBS. Plates were incubated for 4 hours at 37° C. and then washed 3 times with 0.01% PBS-Tween (PBS-T). Bound MSP-1$_{33}$ protein was detected by addition of 100 μl of 1:4000 dilution of mouse mAb G13 for 1 hour at 37° C., followed by washing and the addition of 100 μl of 1:1000 dilution of sheep anti-mouse IgG (H+L) HRP-conjugated antibody. After incubation for 1 h at 37° C., the plates were washed again and HRP was detected by the addition of 100 μl of freshly prepared substrate solution (400 mg l$^{-1}$ o-phenylenediamine dihydrochloride in 0.05 M phosphate buffer, 0.024 M citric acid and 0.012% $H_2O_2$) at room temperature for 20 min. The reaction was stopped by adding 10 μl of 1 M sulphuric acid and the absorbance of each sample was measured at 492 nm.

Results

The results are shown in FIG. 13. The two modified proteins produced antibodies that reacted with MSP-1 in the parasite-infected erythrocyte, with a serum titre of 1:10,000, which was an identical titre to that of a serum produced in the same way by immunisation with a recombinant protein containing the wildtype MSP-1 sequence. This indicates that the modified proteins can produce antibodies that react with the native protein. The antibodies induced by immunization were able to partially inhibit processing at the concentration used in a preliminary experiment, whereas in the control serum no antibodies that inhibited processing were present.

EXAMPLE 5

Design and Synthesis of a *Plasmodium Falciparum* Merozoite Surface Protein-1 Gene Fragment Optimized for *Pichia Pastoris* Heterologous Expression The coding sequence of the *Plasmodium falciparum* merozoite surface protein-1 (MSP1) 41.1 kDa processed fragment (MSP-142) has been redesigned for optimal heterologous expression in the yeast *Pichia pastoris*. The optimized DNA sequence was synthesized by PCR gene assembly, in the form of two fragments, MSP-133 and MSP-119. *P. pastoris* was transformed with an expression vector containing the optimized MSP-119 construct. Recombinant strains were shown to express high levels of non-glycosylated, properly folded MSP-119 protein.

Proteins encoded by the AT-rich genome of the human malaria parasite *Plasmodium falciparum* are generally poorly expressed in heterologous systems (Withers-Martinez et al., 1999). The methylotrophic yeast *Pichia (Komagataella) pastoris* is an appropriate system for expression of disulphide-bridged proteins such as the C-terminal fragment of the *P. falciparum* merozoite surface protein-1 (MSP1) (White et al., 1994; Morgan et al., 1999). In the *P. pastoris* expression system, it is important to avoid premature transcription termination due to AT-rich stretches (Romanos et al., 1991). Codon preferences for highly expressed genes in *P. pastoris* have been identified (Sreekrishna et al., EP 0 586 892 A1). Therefore, a synthetic MSP-142 gene fragment with codon usage optimized for *P. pastoris* expression was designed, using novel computer software (Withers-Martinez et al., 1999). It has previously been shown that the MSP-119 fragment is partially glycosylated when expressed in *P. pastoris*, and the carbohydrate must be enzymatically removed during purification (Morgan et al., 1999). Therefore, two specific point mutations were introduced into the synthetic MSP-142 protein sequence in order to prevent N-linked glycosylation at NxS/T sites (one potential site within the MSP-133 sequence, and a known site within the MSP-119 sequence at Asn1).

The optimized MSP-142 sequence was synthesized by gene assembly polymerase chain reaction (Stemmer et al., 1995, Withers-Martinez et al., 1999), in the form of separate MSP-133 and MSP-119 fragments. The optimized MSP-119 fragment was subcloned into a novel modified *Pichia* expression vector, transformed into the *P. pastoris* host strain SMD1168, and several independent transformants were isolated. There transformants were shown to efficiently express non-glycosylated, properly folded MSP-119. Strong expression of the optimized gene was observed in low copy number transformants. A multiple copy transformant with intermediate level G418 resistance gave expression of purified MSP-119 at a level equal to the high-expressing strain previously described (Morgan et al., 1999), which contains the original *P. falciparum* DNA. Thus, it should be possible to obtain even higher yields from high level G418-resistant transformants of the synthetic optimized gene.

Methods: Gene Assembly

The *P. falciparum* MSP-142 (41.1 kDa) fragment protein sequence SWISS-PROT accession number P04933: positions 1264–1621) was first altered to eliminate N-linked glycosylation signals by 2 amino acid substitutions. The sequences NYT (in the N-terminal portion; position 1445) and NIS (at the beginning of the C-terminal fragment; position 1526) were changed to QYT and NIA respectively. The protein sequence was then reverse-translated with DNA-STAR using the *S. cerevisiae* codon preferences. This sequence was used as input for the CODOP program (Withers-Martinez et al., 1999). Ten random sequences were generated with this program, using a codon weighting table (FIG. 14) derived from codon usage in highly expressed *P. pastoris* genes (Sreekrishna et al., EP 0 586 892 A1). Thus, the codon table should reflect usage in highly expressed genes, rather than average usage. The random sequence that contained the minimum number of unfavourable codons (6) was selected, and these codons were changed manually to more preferred alternatives. The sequence was then analysed with DNA-STAR to check for AT-rich sequences that may cause transcription termination, and for direct and inverted repeats. A set of 50 overlapping oligonucleotides coding for the final sequence was then generated. This consisted of 49 oligonucleotides of length 42 nt, and one of length 48 nt. Each oligonucleotide had a 21 bp overlap with its neighbours, with no gaps. Estimated $T_m$s were in the range of 60° C. to 77° C. Oligonucleotides were synthesised by Oswel (Southampton, UK) at 40 nmol scale, and supplied in deionised water without purification. Outside primers of various lengths for the amplification step were also synthesised, to give a $T_m$ of 62° C. to 64° C., and contained a 5'-terminal phosphate group for ligation following the amplification step. The reverse primers also included a translation termination codon (UAA in the complementary strand). All oligonucleotides were diluted to 10 μM in ddH$_2$O before use.

The PCR-mediated gene assembly and amplification were carried out as described (Stemmer et al., 1995; Withers- Martinez et al., 1999), using a Biometra cycler, in thin-walled 200 μL tubes, under the following conditions.

```
Gene assembly reactions (Reaction 1):
50 μL volume
    2 units Vent polymerase (New England Biolabs)
    0.4 mM dNTPs
    1 × Vent polymerase buffer
    Oligonucleotide mix containing each oligonucleotide at 200 nM
Cycles:
    32 cycles (2 h 33 m)
    denaturation 94° C. 30 s
    annealing 52° C. 30 s
    extension 72° C. 3 m
```

Three fragments of the MSP-142 (41.1 kDa) region were synthesised separately with different outside primers and subsets of the 50 oligonucleotide set:

N-terminal fragment (bp 1-423) 21 oligonucleotides
middle fragment (bp 337-786) 22 oligonucleotides
C-terminal fragment (bp 787-1074) 14 oligonucleotides The C-terminal fragment produces a 10.6 kDa fragment (MSP-119). The N-terminal and middle fragments, which overlap between positions 337 and 423, were subsequently spliced together at the BglII site (371-376) to give a 786 bp fragment that encodes the 30.5 kDa MSP-133 protein.

```
Amplification reactions (Reaction 2):
100 μL volume
    10 μL aliquot of the gene assembly reaction
    4 units Vent polymerase
    0.4 mM dNTPs
    1 × Vent polymerase buffer
    1 μM outside primers
Cycles:
    32 cycles (2 h 55 m)
    denaturation 94° C. 45 s
    annealing 52° C. 45 s
    extension 72° C. 3 m
    final extension 72° C. 5 m
```

The PCR products were then purified by filtration with Centricon-100 units (Amicon), and cloned directly into the vectors by blunt-end ligation overnight at 16° C. with T4 DNA ligase. The synthetic MSP-119 gene was cloned directly into a P. pastoris expression vector. The modified pPIC9KHXa vector, containing a $His_6$ tag and factor Xa cleavage site (see FIG. 15) inserted in the pPIC9K SnaBI site, had been digested with PmlI and treated with calf alkaline phosphatase. The HXa vector had been previously created by insertion of a 36 bp synthetic oligonucleotide, containing the $His_6$ tag, factor Xa cleavage site, and PmlI restriction site into the SnaBI site of the pPIC9K vector.

The N-terminal and middle fragment PCR products were cloned into the SmaI site of the dephosphorylated pUC 118 vector. Plasmid clones containing inserts were sequenced. Clones with the correct synthetic sequence were then digested and the two fragments were gel-purified. The N-terminal fragment clones were digested with EcoRI and BglII, and the middle fragment clones were digested with HindIII and BglII. The recombinant fragments were purified on an agarose gel, and eluted with a QIAGEN extraction kit. The purified N-terminal and middle fragments were then spliced together by ligation into a pUC118 vector that had been digested with HindIII and EcoRI and treated with calf alkaline phosphatase. This created the complete synthetic MSP-133 coding sequence. The N-terminal and middle fragment PCR products were cloned into the SmaI site of the dephosphorylated pUC118 vector. Plasmid clones containing inserts were sequenced. Clones with the correct synthetic sequence were then digested and the two fragments were gel-purified. The N-terminal fragment clones were digested with EcoRI and BglII, and the middle fragment clones were digested with HindIII and BglII. The recombinant fragments were purified on an agarose gel, and eluted with a QIAGEN extraction kit. The purified N-terminal and middle fragments were then spliced together by ligation into a pUC118 vector that had been digested with HindIII and EcoRI and treated with calf alkaline phosphatase. This created the complete synthetic MSP-133 coding sequence.

Methods: Expression and Purification

The methylotrophic yeast Pichia (Komagataella) pastoris strain SMD 1168 was transformed by electroporation as described previously (Morgan et al., 1999). In addition, some G418-resistant clones were isolated using Hybond-N+ membranes (Fairlie et al., 1999).

Expression screening of transformants was performed by growing 10 ml cultures in buffered minimal glucose medium. Cells were harvested and resuspended in 10 ml buffered minimal methanol medium at 1.0 $OD_{600}$ and grown overnight to a final $OD_{600}$ of 2.5 to 3.0. Cells were removed by centrifugation, and 1.2 ml of the supernatant medium was precipitated 30 min on ice with 15% trichloroacetic acid. The samples were centrifuged for 30 min at 14000 rpm at 4° C. in a microfuge, and the protein pellets were washed twice with cold acetone. Samples were resuspended in 12 μl $ddH_2O$, and 5 μl was electrophoresed, after reduction with DTT, on NOVEX pre-poured acrylamide gels according to manufacturer's instructions. NOVEX 4-12% acrylamide gradient, or 10% acrylamide, Bis/Tris gels in MES buffer were used. Protein gels were stained with Coomassie colloidal Brilliant Blue stain (Sigma).

Homogeneously purified MSP-119 was obtained as described previously (Morgan et al., 1999), except that enzymatic deglycosylation was omitted for the synthetic gene products.

Methods: NMR

One-dimensional $^1H$- and 2-dimensional $\{^1H/^{15}N\}$-HSQC spectra were acquired as described previously (Morgan et al., 1999), at 25° C., at sample concentrations of 1.1–2.5 mM.

Results

The sequences of the synthetic DNA fragments, and the resulting predicted protein products, are shown in FIG. 15. A summary of the resulting improvements to the sequence is given in Table 3.

TABLE 3

| | Codon usage | | | |
|---|---|---|---|---|
| | Total codons | P. pastoris preferred codons | Unfavourable codons | % AT content |
| P. falciparum MSP1 41.1 kDa fragment | 358 | 140 | 28 | 74 |
| Synthetic 41.1 kDa fragment | 358 | 276 | 0 | 58 |

PCR-gene assembly reactions for the MSP-133 (two sections) and MSP-119 synthetic fragments are shown on agarose gels in FIG. 16. This demonstrated that a single, correct size major product was observed in each case. The PCR products were subcloned, screened, and sequenced as described in the Methods section.

*P. pastoris* was transformed with the synthetic MSP-119 construct in the modified pPIC9K expression vector (pPIC9K-HXa; FIG. 15). Expression of the synthetic MSP-119 product in three independent transformants is shown on a protein gel in FIG. 17. The protein samples were prepared by trichloroacetic acid precipitation from culture supernatants as described in the Methods section. This demonstrated that a single, major product was present in each sample, corresponding to the expected migration of the synthetic MSP-119 protein. This migrated slightly more slowly than the control sample, which as described previously (Morgan et al., 1999) has a shorter N-terminal tag sequence. There was no trace of heterogeneous, slowly migrating recombinant protein that would result from glycosylation. Therefore, non-glycosylated, synthetic MSP-119 is efficiently expressed by the transformed yeast. The yield (measured by UV absorbance) of purified MSP-119 was 16 mg/L for low copy number transformants (resistant to 0.25 mg/ml G418), and increased to 24 mg/L for intermediate G418 resistance (resistant to 1.0 mg/ml G418). This can be compared with yields of 1–2 mg/L for low copy number transformants of *P. pastoris* with the original *Plasmodium falciparum* coding sequence, before isolation of a highly G418-resistant strain (Morgan et al., 1999). This indicated that the synthetic MSP-119 construct is advantageous for recombinant protein expression, and that further improvement would result from isolation of higher copy number transformants.

One-dimensional proton NMR experiments demonstrated that the synthetic MSP-119 protein spectrum was very similar to the previously studied protein (Morgan et al., 1999), and represented a correctly folded protein (data not shown). This was further confirmed by a 2D-$\{^1H/^{15}N\}$-HSQC spectra (FIG. 18), which also shows that the structure of the synthetic product is identical to the previously studied protein, except for slight differences at the N-terminus which are consistent with the presence of a distinct N-terminal tag sequence, and S3->A mutation at the glycosylation site. Backbone NH proton and $^{15}N$ chemical shifts for the original *P. falciparum* sequence product have been previously presented (Morgan et al., 1999). The similarity between the two spectra, outside of the N-terminal region, is strong evidence that both protein forms are in a structurally similar, correctly folded state.

REFERENCES

Abseher, R., Horstink, L., Hilbers, C. W. & Nilges, M. (1998). Essential spaces defined by NMR structure ensembles and molecular dynamics simulation show significant overlap. *Proteins: Structure, Function and Genetics*, 31, 370–382.

Barbato, G., Ikura, M., Kay, L. E., Pastor, R. W. & Bax, A. (1992). Backbone dynamics of calmodulin studied by N-15 relaxation using inverse detected 2-dimensional nmr-spectroscopy—the central helix is flexible. *Biochemistry*, 31, 5269–5278.

Bersch, B., Hernandez, J-F., Marion, D. & Arland, G. A. (1998). Solution structure of the epidermal growth factor (EGF)-like module of human complement C1r, an atypical member of the EGF family. *Biochemistry*, 37, 1204–1214.

Blackman, M. J. & Holder, A. A. (1992). Secondary processing of the *Plasmodium falciparum* merozoite surface protein-1 (MSP-1) by a calcium-dependent membrane-bound serine protease: shedding of MSP-1$_{33}$ as a noncovalently associated complex with other fragments of the MSP-1. *Mol. Biochem. Parasitol.* 50, 307–316.

Blackman, M. J., Heidrich, H.-G. Donachie, S., McBride, J. S. & Holder, A. A. (1990). A single fragment of a malaria merozoite surface protein remains on the parasite surface during red cell invasion and is the target of invasion-inhibiting antibodies. *J. Exp. Med.* 172, 379–382.

Blackman, M. J., J. A. Chappel, S. Shai and A. A. Holder, A. A. (1993). A conserved parasite serine protease processes the *Plasmodium falciparum* merozoite surface protein-1 (MSP-1). *Mol. Biochem. Parasitol.* 62, 103–114.

Blackman, M. J., Scott-Finnigan, T. J., Shai, S. & Holder, A. A. (1994). Antibodies inhibit the protease-mediated processing of a malaria merozoite surface protein. *J. Exp. Med.* 180, 389–393.

Blackman, M. J., Ling, I. T., Nicholls, S. C. & Holder, A. A. (1991). Proteolytic processing of the *Plasmodium falciparum* merozoite surface protein-1 produces a membrane-bound fragment containing two epidermal growth factor-like domains. *Mol. Biochem. Parasitol.* 49, 29–34.

Brandstetter, H., Bauer, M., Huber, R., Lollar, P. & Bode, W. (1995). X-ray structure of clotting factor IXa: active site and module structure related to Xase activity and hemophilia B. *Proc. Nat. Acad. Sci. USA*, 92, 9796–9800.

Burghaus, P. A. & Holder, A. A. (1994). Expression of the 19-kilodalton carboxy-terminal fragment of the *Plasmodium falciparum* merozoite surface protein-1 in *Escherichia coli* as a correctly folded protein. *Mol. Biochem. Parasitol.* 64, 165–169.

Campbell, I. D. & Downing, A. K. (1998). NMR of modular proteins. *Nat. Struct. Biol.* 5, Suppl 496–499.

Clare, J. J. & Romanos, M. A. (1995). Expression of Cloned Genes in the Yeasts *Saccharomyces cerevisiae* and *Pichia pastoris*. *Methods in Molec. Cell Biol.* 5, 319–329.

Clore, G. M. & Gronenborn, A. M. (1998). Determining the structures of large proteins and protein complexes by NMR. *Trends in Biotechnology*, 16, 22–34.

Daly, T. M., Burns, J. M. & Long, C. A. (1992). Comparison of the carboxyl terminal, cysteine-rich domain of the merozoite surface protein-1 from several strains of *Plasmodium yoelii*. *Mol. Biochem. Parasitol.* 52, 279–282.

Del Portillo, H. A., Longacre, S., Khouri, E. & David, P. H. (1991). Primary structure of the merozoite surface antigen-1 of *Plasmodium vivax* reveals sequences conserved between different *Plasmodium* species. *Proc. Natl. Acad. Sci. USA* 88, 4030–4034.

Diggs, C. L., Ballou, W. R. & Miller, L. H. (1993). The major merozoite surface protein as a malaria vaccine target. *Parasitol Today*, 9, 300–302.

Doreleijers, J. F., Rullman, J. A. C. & Kaptein, R. (1998). Quality assessment of NMR structures: a statistical approach. *J. Mol. Biol.* 281, 149–164.

Downing, A. K., Knott, V., Werner, J. M., Cardy, C. M., Campbell, I. D. & Handford, P. A. (1996). Solution structure of a pair of calcium binding epidermal growth factor-like domains: implications for the Marfan syndrome and other genetic disorders. *Cell*, 86, 597–605.

Egan, A., Waterfall, M., Pinder, M., Holder, A. & Riley, E. (1997) Characterization of human T- and B- cell epitopes in the C-terminus of *Plasmodium falciparum* merozoite surface protein 1: evidence for poor T-cell recognition of polypeptides with numerous disulfide bonds. *Infect. Immun.* 65, 3024–3031.

Fairlie, W. D., Russell, P. K., Zhang, H. P., and Breit, S. N. (1999) Screening Procedure for *Pichia pastoris* Clones Containing Multiple Copy Gene Inserts. *BioTechniques* 26: 1042–1044.

Gibson, H. L., Tucker, J. E., Kaslow, D. C., Krettli, A. U., Collins, W. E., Kiefer, M. C., Bathurst, I. C. & Barr, P. J. (1992). Structure and expression of the gene for Pv200, a major blood-stage surface antigen of *Plasmodium vivax*. *Mol. Biochem. Parasitol.* 50, 325–334.

Guevara Patiño, J. A., Holder, A. A., McBride, J. S. & Blackman, M. J. (1997). Antibodies that inhibit malaria merozoite surface protein-1 processing and erythrocyte invasion are blocked by naturally acquired human antibodies. *J. Exp. Med.* 186, 1689–1699.

Holder, A. A., Blackman, M. J., Burghaus, P. A., Chappel, J. A., Ling, I. T., McCallum-Deighton, N. & Shai, S. (1992). A malaria merozoite surface protein (MSP-1)—Structure, processing and function. *Mem. Inst. Oswaldo Cruz,* 87, Suppl III, 37–42.

Holder, A. A., Lockyer, M. J., Odink, K. G., Sandhu, J. S., Riveros-Moreno, V., Nicholls, S. C., Hillman, Y., Davey, L. S., Tizard, M. L. V., Schwarz, R. T. & Freeman, R. R. (1985). Primary structure of the precursor to the three major surface antigens of *Plasmodium falciparum* merozoites. *Nature* 317, 270–273.

Kay, L. E., Torchia, D. A. & Bax, A. (1989). Backbone dynamics of proteins as studied by $^{15}N$ inverse detected heteronuclear NMR spectroscopy. Application to staphylococcal nuclease. *Biochemistry,* 28, 8972–8979.

Kraulis, P. J. (1991). Molscript—a program to produce both detailed and schematic plots of protein structures. *J. Appl. Cryst.* 24, 946–950.

Laroche, Y., Storme, V., de Meutter, J., Messens, J. & Lauwereys, M. (1994). High-level secretion and very efficient isotopic labeling of tick anticoagulant peptide (TAP) expressed in the methylotrophic yeast, *Pichia pastoris*. *Bio/Technology,* 12, 1119–1124.

Laskowski, R. A., Rullmann, J. A. C., MacArthur, M. W., Kaptein, R. & Thornton, J. M. (1996). AQUA and PROCHECK-NMR: Programs for checking the quality of protein structures solved by NMR. *J. Biomol. NMR,* 8, 477–486.

McBride, J. S. & Heidrich, H. -G. (1987). Fragments of the polymorphic Mr 185,000 glycoprotein from the surface of isolated *Plasmodium falciparum* merozoites form an antigenic complex. *Mol. Biochem. Parasitol.* 23, 71–84.

McDonald, I. K. & Thornton, J. M. (1994). Satisfying hydrogen bonding potential in proteins. *J. Biol. Chem.* 238, 777–793.

Morgan, W. D., Birdsall, B., Frenkiel, T. A., Gradwell, M. G., Burghaus, P. A., Syed, S. E. H., Uthaipibull, C., Holder, A. A., and Feeney, J. (1999) Solution structure of an EGF module pair from the *Plasmodium falciparum* Merozoite Surface Protein 1, *J. Mol. Biol.,* 289, 113–122.

Mrema, J. E. K., S. G. Langreth, R. C. Jost, K. H. Rieckmann and H.-G. Heidrich (1982). *Plasmodium falciparum*: isolation and purification of spontaneously released merozoites by nylon sieve membranes. *Exp. Parasitol.* 54, 285.

Nicholls, A., Sharp, K. A. & Honig, B. (1991). Protein folding and association: insights from the interfacial and thermodynamic properties of hydrocarbons. *Proteins,* 11, 281–296.

Nilges, M., Kuszewski, J. & Briinger, A. T. (1991). Sampling properties of simulated annealing and distance geometry in *Computational Aspects of the Study of Biological Macromolecules by NMR.* (J. C. Hoch, ed.) NY, Plenum Press.451–455.

Perrin, S & Gilliland, G. (1990). Site specific mutagenesis using asymmetric polymerase chain reaction and a single mutant primer. *Nucl. Acids Res.* 18, 7433–7438

Pirson, P. J. & Perkins, M. E. (1985). Characterization with monoclonal antibodies of a surface antigen of *Plasmodium falciparum* merozoites. *J. Immunol.* 134, 1946–1951.

Polshakov, V. I., Frenkiel, T. A., Birdsall, B., Soteriou, A. & Feeney, J. (1995). Determination of stereospecific assignments torsion-angle constraints and rotamer populations in proteins using the program AngleSearch. *J. Magn. Reson. Series B,* 108, 31–43.

Polshakov, V. I., Williams, M., Gargaro, A., Frenkiel, T. A., Westley, B. R., Chadwick, M. P., May, F. E. B. & Feeney, J. (1997). High resolution solution structure of the human breast cancer oestrogen-inducible pNR-2/pS2: a single trefoil domain. *J. Mol. Biol.* 267, 418–432.

Qari, S. H., Shi, Y. P., Goldman, I. F., Nahlen, B. L., Tibayrenc, M., Lal, A. A. (1998). Predicted and observed alleles of *Plasmodium falciparum* merozoite surface protein 1 (MSP-1), a potential malaria vaccine antigen. *Mol. Biochem. Parasitol.* 92(2), 241–252.

Richardson, J. S. (1981). The Anatomy and Taxonomy of Protein structure. *Adv. Prot. Chem.* 34, 167–339.

Romanos, M. A., Makoff, A., Fairweather, N. F., Beesley, K. M., Slater, D. E., Rayment, F. B., Payne, M. M., and Clare, J. J. (1991) Expression of Tetanus Toxin Fragment-C in YEAST-Gene Synthesis is Required to Eliminate Fortuitous Polyadenylation Sites in AT-Rich DNA. *Nucleic Acids Res.,* 19: 1461–1467.

Ryckaert, J-P., Ciccutti, G. & Berendsen, H. J. C. (1977). Numerical-integration of Cartesian equations of motion of a system with constraints—molecular dynamics of N-alkanes. *J. Comput. Phys.* 23, 327–351.

Stemmer, W. P. C., Crameri, A., Ha, K. D., Brennan, T. M., and Heyneker, H. L. (1995) Single-step assembly of a gene and entire plasmid from large numbers of oligodeoxyribonucleotides. *Gene,* 164: 49–53.

Stoute, J. A. & Ballou, W. R. (1998). The current status of malaria vaccines. *BIODRUGS* 10,123–136.

White, C. E., Kempi, N. M., and Komives, E. A., (1994), Expression of highly disulfide-bonded proteins in *Pichia pastoris*, Structure, 2: 1003–1005.

Withers-Martinez, C., Carpenter, E. P., Hackett, F., Ely, B., Sajid, M., Grainger, M., and Blackman, M. J. (1999) PCR-based gene synthesis as an efficient approach for expression of the A+T-rich malaria genome. *Protein Engineering,* 12: 1113–1120.

SEQ I.D. No. 1 - *P. falciparum* MSP-1$_{19}$ (From SwissProt accession no. P04933)

NISQHQCVKK QCPQNSGCFR HLDEREECKC LLNYKQEGDK CVENPNPTCN 50

-continued

ENNGGCDADA KCTEEDSGSN GKKITCECTK PDSYPLFDGI FCSSSN    96

SEQ I.D. No. 2 - *P. falciparum* MSP-1$_{42}$ (Type 1, from SwissProt
accession no. P04933)

```
    AVTPSVI DNILSKIENE YEVLYLKPLA GVYRSLKKQL ENNVMTFNVN VKDILNSRFN    57
KRENFKNVLE SDLIPYKDLT SSNYVVKDPY KFLNKEKRDK FLSSYNYIKD SIDTDINFAN   117
DVLGYYKILS EKYKSDLSI KKYINDKQGE NEKYLPFLNN IETLYKTVND KIDLFVIHLE   177
AKVLNYTYEK SNVEVKIKEL NYLKTIQDKL ADFKKNNNFV GIADLSTDYN HNNLLTKFLS   237
TGMVFENLAK TVLSNLLDGN LQGMLNISQH QCVKKQCPQN SGCFRHLDER EECKCLLNYK   297
QEGDKCVENP NPTCNENNGG CDADAKCTEE DSGSNGKKIT CECTKPDSYP LFDGIFCSSS   357
NFLGISFLLI LMLILYSFI                                                376
```

SEQ I.D. No. 3 - *P. falciparum* MSP-1$_{42}$ (Type 2, from SwissProt
accession no. P04933)

```
AISVTMDNIL SGFENEYDVI YLKPLAGVYR SLKKQIEKNI FTFNLNLNDI LNSRLKKRKY    60
FLDVLESDLM QFKHISSNEY IIEDSFKLLN SEQKNTLLKS YKYIKESVEN DIKFAQEGIS   120
YYEKVLAKYK DDLESIKKVI KEEKEKFPSS PPTTPPSPAK TDEQKKESKF LPFLTNIETL   180
YNNLVNKIDD YLINLKAKIN DCNVEKDEAH VKITKLSDLK AIDDKIDLFK NPYDFEAIKK   240
LINDDTKKDM LGKLLSTGLV QNFPNTIISK LIEGKFQDML NISQHQCVKK QCPENSGCFR   300
HLDEREECKC LLNYKQEGDK CVENPNPTCN ENNGGCDADA TCTEEDSGSS RKKITCECTK   360
PDSYPLFDGI FCSSSNFLGI SFLLILMLIL YSFI                                39
```

---

SEQUENCE LISTING

<160> NUMBER OF SEQ ID NOS: 3

<210> SEQ ID NO 1
<211> LENGTH: 96
<212> TYPE: PRT
<213> ORGANISM: Plasmodium falciparum

<400> SEQUENCE: 1

```
Asn Ile Ser Gln His Gln Cys Val Lys Lys Gln Cys Pro Gln Asn Ser
1               5                   10                  15

Gly Cys Phe Arg His Leu Asp Glu Arg Glu Glu Cys Lys Cys Leu Leu
            20                  25                  30

Asn Tyr Lys Gln Glu Gly Asp Lys Cys Val Glu Asn Pro Asn Pro Thr
        35                  40                  45

Cys Asn Glu Asn Gly Gly Cys Asp Ala Asp Ala Lys Cys Thr Glu
    50                  55                  60

Glu Asp Ser Gly Ser Asn Gly Lys Lys Ile Thr Cys Glu Cys Thr Lys
65                  70                  75                  80

Pro Asp Ser Tyr Pro Leu Phe Asp Gly Ile Phe Cys Ser Ser Asn
                85                  90                  95
```

<210> SEQ ID NO 2
<211> LENGTH: 376
<212> TYPE: PRT
<213> ORGANISM: Plasmodium falciparum

<400> SEQUENCE: 2

```
Ala Val Thr Pro Ser Val Ile Asp Asn Ile Leu Ser Lys Ile Glu Asn
1               5                   10                  15
```

Glu Tyr Glu Val Leu Tyr Leu Lys Pro Leu Ala Gly Val Tyr Arg Ser
           20                  25                  30

Leu Lys Lys Gln Leu Glu Asn Asn Val Met Thr Phe Asn Val Asn Val
           35                  40                  45

Lys Asp Ile Leu Asn Ser Arg Phe Asn Lys Arg Glu Asn Phe Lys Asn
         50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Lys Phe Leu Asn Lys Glu Lys Arg Asp
                    85                  90                  95

Lys Phe Leu Ser Ser Tyr Asn Tyr Ile Lys Asp Ser Ile Asp Thr Asp
                100                 105                 110

Ile Asn Phe Ala Asn Asp Val Leu Gly Tyr Tyr Lys Ile Leu Ser Glu
            115                 120                 125

Lys Tyr Lys Ser Asp Leu Asp Ser Ile Lys Lys Tyr Ile Asn Asp Lys
        130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Val
                180                 185                 190

Lys Ile Lys Glu Leu Asn Tyr Leu Lys Thr Ile Gln Asp Lys Leu Ala
            195                 200                 205

Asp Phe Lys Lys Asn Asn Asn Phe Val Gly Ile Ala Asp Leu Ser Thr
        210                 215                 220

Asp Tyr Asn His Asn Asn Leu Leu Thr Lys Phe Leu Ser Thr Gly Met
225                 230                 235                 240

Val Phe Glu Asn Leu Ala Lys Thr Val Leu Ser Asn Leu Leu Asp Gly
                245                 250                 255

Asn Leu Gln Gly Met Leu Asn Ile Ser Gln His Gln Cys Val Lys Lys
                260                 265                 270

Gln Cys Pro Gln Asn Ser Gly Cys Phe Arg His Leu Asp Glu Arg Glu
            275                 280                 285

Glu Cys Lys Cys Leu Leu Asn Tyr Lys Gln Glu Gly Asp Lys Cys Val
        290                 295                 300

Glu Asn Pro Asn Pro Thr Cys Asn Glu Asn Asn Gly Gly Cys Asp Ala
305                 310                 315                 320

Asp Ala Lys Cys Thr Glu Glu Asp Ser Gly Ser Asn Gly Lys Lys Ile
                325                 330                 335

Thr Cys Glu Cys Thr Lys Pro Asp Ser Tyr Pro Leu Phe Asp Gly Ile
            340                 345                 350

Phe Cys Ser Ser Ser Asn Phe Leu Gly Ile Ser Phe Leu Leu Ile Leu
        355                 360                 365

Met Leu Ile Leu Tyr Ser Phe Ile
    370                 375

<210> SEQ ID NO 3
<211> LENGTH: 394
<212> TYPE: PRT
<213> ORGANISM: Plasmodium falciparum

<400> SEQUENCE: 3

Ala Ile Ser Val Thr Met Asp Asn Ile Leu Ser Gly Phe Glu Asn Glu

-continued

```
1               5                   10                  15
Tyr Asp Val Ile Tyr Leu Lys Pro Leu Ala Gly Val Tyr Arg Ser Leu
                20                  25                  30
Lys Lys Gln Ile Glu Lys Asn Ile Phe Thr Phe Asn Leu Asn Leu Asn
                35                  40                  45
Asp Ile Leu Asn Ser Arg Leu Lys Lys Arg Lys Tyr Phe Leu Asp Val
                50                  55                  60
Leu Glu Ser Asp Leu Met Gln Phe Lys His Ile Ser Ser Asn Glu Tyr
 65                 70                  75                  80
Ile Ile Glu Asp Ser Phe Lys Leu Leu Asn Ser Glu Gln Lys Asn Thr
                85                  90                  95
Leu Leu Lys Ser Tyr Lys Tyr Ile Lys Glu Ser Val Glu Asn Asp Ile
                100                 105                 110
Lys Phe Ala Gln Glu Gly Ile Ser Tyr Tyr Glu Lys Val Leu Ala Lys
                115                 120                 125
Tyr Lys Asp Asp Leu Glu Ser Ile Lys Lys Val Ile Lys Glu Glu Lys
                130                 135                 140
Glu Lys Phe Pro Ser Ser Pro Thr Pro Pro Ser Pro Ala Lys
145                 150                 155                 160
Thr Asp Glu Gln Lys Lys Glu Ser Lys Phe Leu Pro Phe Leu Thr Asn
                165                 170                 175
Ile Glu Thr Leu Tyr Asn Asn Leu Val Asn Lys Ile Asp Asp Tyr Leu
                180                 185                 190
Ile Asn Leu Lys Ala Lys Ile Asn Asp Cys Asn Val Glu Lys Asp Glu
                195                 200                 205
Ala His Val Lys Ile Thr Lys Leu Ser Asp Leu Lys Ala Ile Asp Asp
                210                 215                 220
Lys Ile Asp Leu Phe Lys Asn Pro Tyr Asp Phe Glu Ala Ile Lys Lys
225                 230                 235                 240
Leu Ile Asn Asp Asp Thr Lys Lys Asp Met Leu Gly Lys Leu Leu Ser
                245                 250                 255
Thr Gly Leu Val Gln Asn Phe Pro Asn Thr Ile Ile Ser Lys Leu Ile
                260                 265                 270
Glu Gly Lys Phe Gln Asp Met Leu Asn Ile Ser Gln His Gln Cys Val
                275                 280                 285
Lys Lys Gln Cys Pro Glu Asn Ser Gly Cys Phe Arg His Leu Asp Glu
                290                 295                 300
Arg Glu Glu Cys Lys Cys Leu Leu Asn Tyr Lys Gln Glu Gly Asp Lys
305                 310                 315                 320
Cys Val Glu Asn Pro Asn Pro Thr Cys Asn Glu Asn Asn Gly Gly Cys
                325                 330                 335
Asp Ala Asp Ala Thr Cys Thr Glu Glu Asp Ser Gly Ser Ser Arg Lys
                340                 345                 350
Lys Ile Thr Cys Glu Cys Thr Lys Pro Asp Ser Tyr Pro Leu Phe Asp
                355                 360                 365
Gly Ile Phe Cys Ser Ser Ser Asn Phe Leu Gly Ile Ser Phe Leu Leu
                370                 375                 380
Ile Leu Met Leu Ile Leu Tyr Ser Phe Ile
385                 390
```

The invention claimed is:

1. An isolated variant of a 19 kd fragment of a *Plasmodium falciparum* merozoite surface protein-1 (MSP-$1_{19}$), wherein:
   (i) said variant has a reduced affinity for at least one blocking antibody to a naturally occurring MSP-$1_{19}$ and which has affinity for at least one neutralizing antibody; and
   (ii) comprising amino acid modifications at Cys12 and Cys28 of a *Plasmodium falciparum* MSP-$1_{19}$ amino acid sequence shown as SEQ ID NO: 1 or their equivalent positions in other *Plasmodium falciparum* MSP-$1_{19}$ polypeptides.

2. The variant according to claim 1 further comprising an amino acid modification at any one of amino acid residues 14, 15, 27, 31, 34, 43, 48 of the *Plasmodium falciparum* MSP-$1_{19}$ amino acid sequence shown as SEQ ID NO 1 or their equivalent positions in other *Plasmodium falciparum* MSP-$1_{19}$ polypeptides.

3. The variant according to claim 2, in which the polypeptide comprises the substitutions selected from Cys12→Ile and Cys28→Trp, and Cys→Ala and Cys28→Phe.

4. A variant according to claim 2 in which the mutation is the deletion of Cys12 and Cys28 of the *Plasmodium falciparum* MSP-$1_{19}$ amino acid sequence shown as SEQ ID No.1.

5. A method for producing the *Plasmodium falciparum* MSP-$1_{19}$ variant of claim 1, comprising:
   (i) providing a polynucleotide encoding a *Plasmodium falciparum* MSP-$1_{19}$;
   (ii) modifying the codons encoding the amino acids Cys12 and Cys28 in said polynucleotide; and
   (iii) expressing said modified polynucleotide in a host cell.

6. A pharmaceutical composition comprising a variant according to claim 1 together with a pharmaceutically acceptable carrier to diluent.

7. A method for producing anti-MSP-1 antibodies which method comprises administering a polypeptide according to claim 1 to a mammal.

8. A method for producing polyclonal anti-MSP-1 antibodies which method comprises administering a polypeptide according to claim 1 to a mammal and extracting the serum from said mammal.

9. A method of inducing immunity against malaria induced by *Plasmodium falciparum* which comprises administering to a person in need of such immunity an effective amount of the variant of claim 1.

10. A method of immunizing a mammal, said method comprising administering an effective amount the polypeptide of claim 1.

11. A method of treating a malaria infection in a human patient which comprises administering to the patient an effective amount of the pharmaceutical composition of claim 6.

12. The variant according to claim 2 wherein said further modification is one selected from Gln14→Arg, Gln14→Gly, Asn15→Arg, Glu27→Tyr, Leu31→Arg, Tyr34→Ser, Tyr34→Ile, Glu43→Leu, Thr48→Lys and Asn53→Arg.

13. The variant according to claim 2, wherein said further modifications are substitutions selected from either Gln14→Arg or Gln14→Gly, Asn15→Arg, Glu27→Tyr, Leu31→Arg, either Tyr34→Ser or Tyr34→Ile, Glu43→Leu, Thr48→Lys and Asn53→Arg and their equivalents in other *Plasmodium falciparum* MSP-$1_{19}$ polypeptides.

14. The variant according to claim 2, wherein said further modifications are combinations of substitutions selected from [Glu27→Tyr, Leu31→Arg and Glu43→Leu], [Glu27→Tyr, Leu31→Arg, Tyr34→Ser and Glu43→Leu], and [Asn15→Arg, Glu27→Tyr, Leu31→Arg and Glu43→Leu] and their equivalents in other *Plasmodium falciparum* MSP-$1_{19}$ polypeptides.

15. The variant according to claim 2, wherein said modifications are substitutions selected from [Cys12→Ile, Asn15→Arg, Glu27→Tyr, Cys28→Trp, Leu31→Arg and Glu43→Leu], [Cys12→Ile, Asn15→Arg, Glu27→Tyr, Cys28→Trp, Leu31→Arg, Glu43→Leu and Asn53→Arg], and [Cys12→Ile, Asn15→Arg, Glu27→Tyr, Cys28→Trp, Leu31→Arg, Tyr34→Ser, Glu43→Leu and Asn53→Arg], and their equivalents in other *Plasmodium falciparum* MSP-$1_{19}$ polypeptides.

* * * * *